(12) United States Patent
Vora et al.

(10) Patent No.: US 11,674,138 B2
(45) Date of Patent: Jun. 13, 2023

(54) METHODS OF MODULATING EXPRESSION OF TARGET NUCLEIC ACID SEQUENCES IN A CELL

(71) Applicant: President and Fellows of Harvard College, Cambridge, MA (US)

(72) Inventors: Suhani D. Vora, Cambridge, MA (US); Alejandro Chavez, New York, NY (US); Jing Cheng, Mountain View, CA (US); Benjamin W. Pruitt, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 781 days.

(21) Appl. No.: 16/486,586

(22) PCT Filed: Mar. 13, 2018

(86) PCT No.: PCT/US2018/022220
§ 371 (c)(1),
(2) Date: Aug. 16, 2019

(87) PCT Pub. No.: WO2018/169983
PCT Pub. Date: Sep. 20, 2018

(65) Prior Publication Data
US 2019/0376060 A1   Dec. 12, 2019

Related U.S. Application Data

(60) Provisional application No. 62/470,538, filed on Mar. 13, 2017.

(51) Int. Cl.
| | | |
|---|---|---|
| *C07H 21/04* | (2006.01) |
| *C12N 15/11* | (2006.01) |
| *C07K 14/31* | (2006.01) |
| *C07K 14/315* | (2006.01) |
| *C12N 9/22* | (2006.01) |
| *C12N 15/86* | (2006.01) |

(52) U.S. Cl.
CPC ............ *C12N 15/111* (2013.01); *C07K 14/31* (2013.01); *C07K 14/315* (2013.01); *C12N 9/22* (2013.01); *C12N 15/86* (2013.01); *C07K 2319/33* (2013.01); *C12N 2310/20* (2017.05); *C12N 2750/14143* (2013.01)

(58) Field of Classification Search
None
See application file for complete search history.

(56) References Cited

U.S. PATENT DOCUMENTS

| | | |
|---|---|---|
| 2005/0175591 A1 | 8/2005 | Stout et al. |
| 2011/0212528 A1 | 9/2011 | Palli et al. |
| 2016/0201089 A1 | 7/2016 | Gersbach et al. |
| 2016/0362705 A1 | 12/2016 | Abraham et al. |
| 2017/0049909 A1 | 2/2017 | Cullen et al. |

FOREIGN PATENT DOCUMENTS

| | | |
|---|---|---|
| CN | 102703502 A | 10/2012 |
| WO | 2015/188065 A1 | 12/2015 |
| WO | 2017/123559 A2 | 7/2017 |
| WO | 2017/197238 A1 | 11/2017 |

OTHER PUBLICATIONS

Chavez, Alejandro, et al. "Highly efficient Cas9-mediated transcriptional programming." Nature methods 12.4 (2015): 326-328.*
Chavez, Alejandro, et al. Supplemental Data "Highly efficient Cas9-mediated transcriptional programming." Nature methods 12.4 (2015): 326-328.*
Dominguez et al. "Beyond editing: repurposing CRISPR-Cas9 for precision genome regulation and interrogation." Nature reviews Molecular cell biology 17.1 (2016): 5-15).*
International Search Report and Written Opinion based on PCT/US2018/022220 dated Jun. 15, 2018.
Chen, Lee-Wen et al., "Two phenylalanines in the C-terminus of Epstein-Barr virus Rta protein reciprocally modulate its DNA binding and transactivation function," Virology, Apr. 10, 2009 (Apr. 10, 2009), vol. 386, No. 2, pp. 448-461. entire document.

* cited by examiner

*Primary Examiner* — Kimberly Chong
(74) *Attorney, Agent, or Firm* — Banner & Witcoff, Ltd.

(57) ABSTRACT

The present disclosure provides methods and compositions of modulating expression of a target nucleic acid sequence in a cell. The method comprises introducing into the cell a nucleic acid sequence encoding a Cas9 fusion protein and a guide RNA, wherein the Cas9 fusion protein and the guide RNA are expressed and co-localize at a target site and modulate the expression of the target nucleic acid sequence.

28 Claims, 30 Drawing Sheets
Specification includes a Sequence Listing.

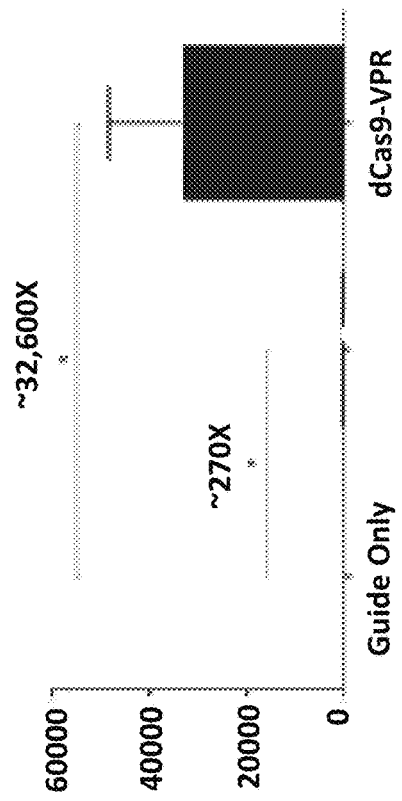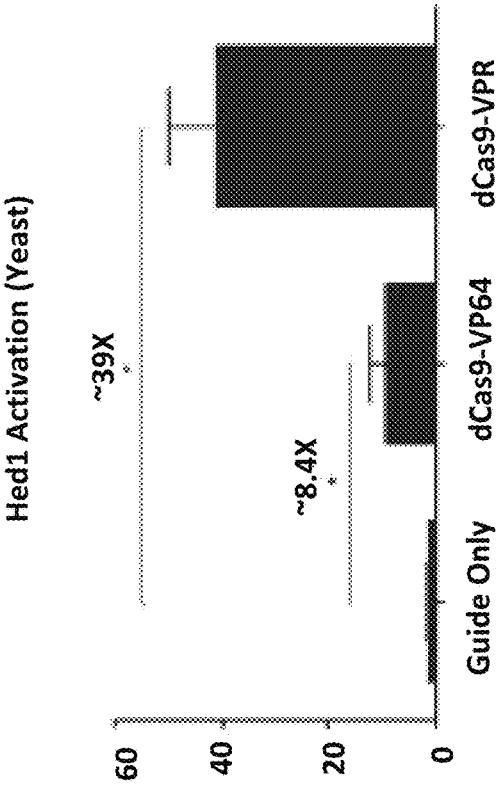
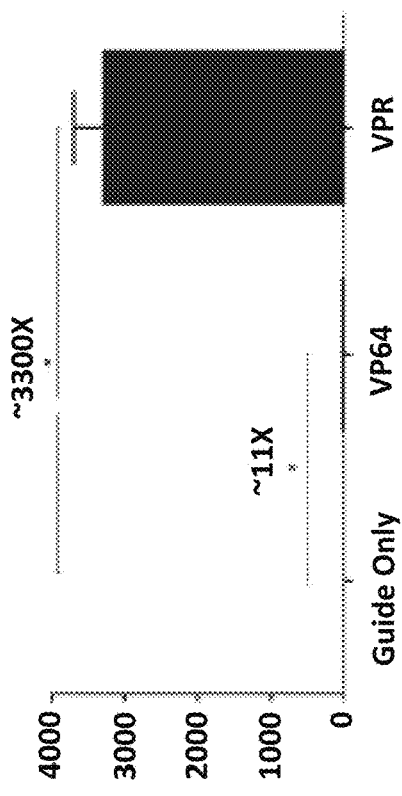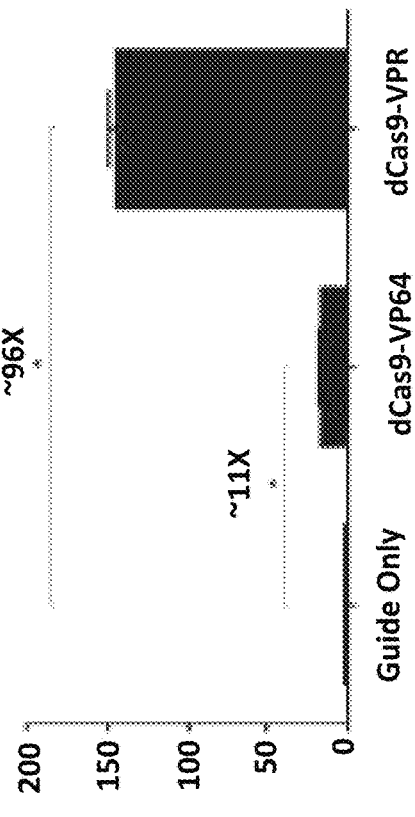
FIG. 5A
FIG. 5B

FIG. 5C  mActc1

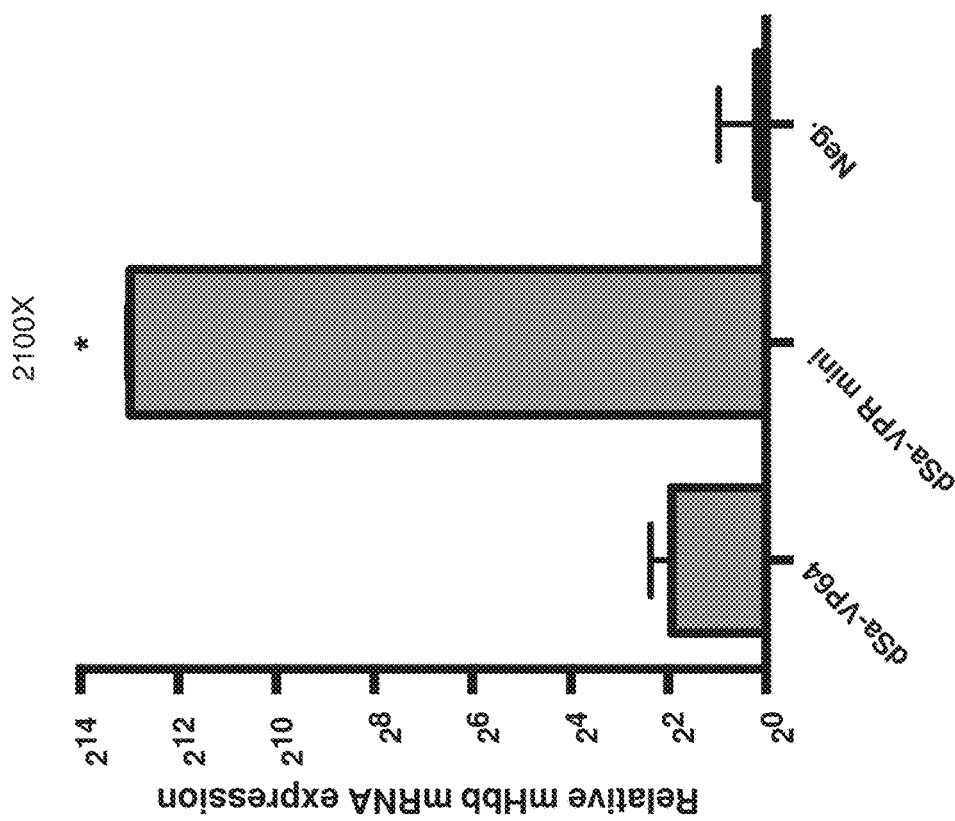
FIG. 9C dSa-VP64 vs dSa-VPR mini. (mActc1)
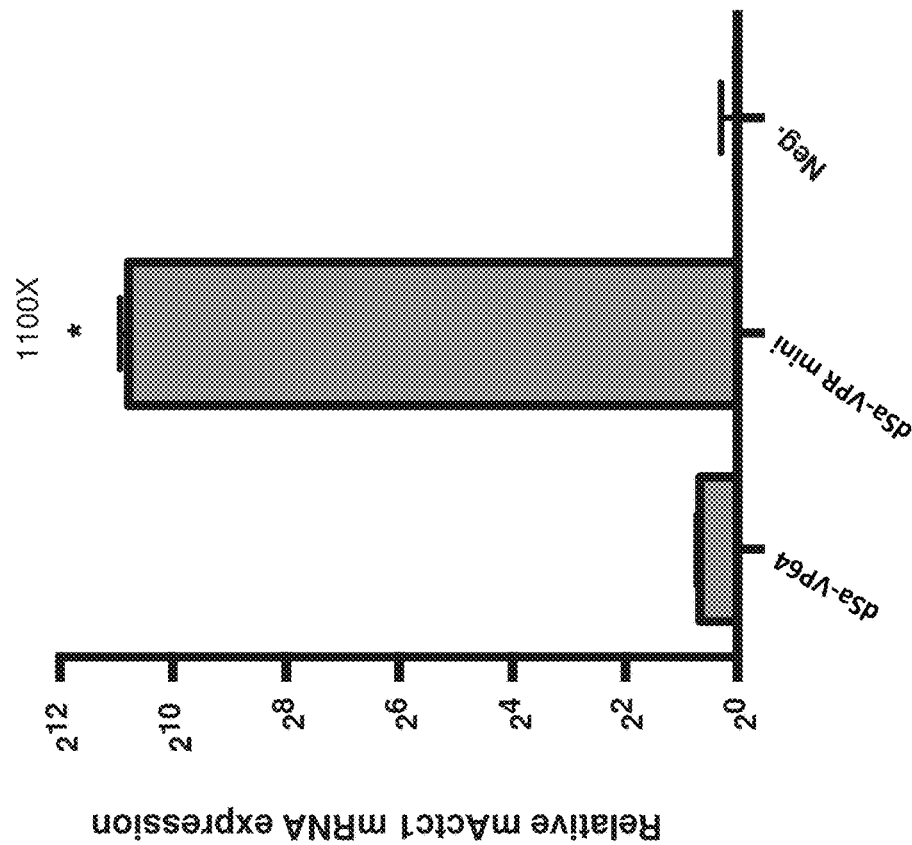
FIG. 9D dSa-VP64 vs dSa-VPR mini. (mHbb)

SEQUENCE LISTING

```
<160> NUMBER OF SEQ ID NOS: 37

<210> SEQ ID NO 1
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaggccagcg gttccggacg ggctgacgca ttggacgatt ttgatctgga tatgctggga      60
agtgacgccc tcgatgattt tgaccttgac atgcttggtt cggatgccct tgatgacttt     120
gacctcgaca tgctcggcag tgacgccctt gatgatttcg acctggacat gctgattaac     180
tctagaagtt ccggatctcc gaaaaagaaa cgcaaagttg gt                        222

<210> SEQ ID NO 2
<211> LENGTH: 783
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
agccagtacc tgcccgacac cgacgaccgg caccggatcg aggaaaagcg gaagcggacc       60
tacgagacat tcaagagcat catgaagaag tcccccttca gcggcccac cgaccctaga      120 cctccaccta gaagaatcgc cgtgcccagc agatccagcg ccagcgtgcc aaaacctgcc     180
ccccagcctt accccttcac cagcagcctg agcaccatca actacgacga gttccctacc     240
atggtgttcc ccagcggcca gatctctcag gcctctgctc tggctccagc ccctcctcag     300
gtgctgcctc aggctcctgc tcctgcacca gctccagcca tggtgtctgc actggctcag     360
gcaccagcac ccgtgcctgt gctggctcct ggacctccac aggctgtggc tccaccagcc     420
cctaaaccta cacaggccgg cgagggcaca ctgtctgaag ctctgctgca gctgcagttc     480
```

```
gacgacgagg atctgggagc cctgctggga aacagcaccg atcctgccgt gttcaccgac      540
ctggccagcg tggacaacag cgagttccag cagctgctga accagggcat ccctgtggcc      600
cctcacacca ccgagcccat gctgatggaa taccccgagg ccatcacccg gctcgtgaca      660
ggcgctcaga ggcctcctga tccagctcct gcccctctgg gagcaccagg cctgcctaat      720
ggactgctgt ctggcgacga ggacttcagc tctatcgccg atatggattt ctcagccttg      780
ctg                                                                    783

<210> SEQ ID NO 3
<211> LENGTH: 570
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
cgggattcca gggaagggat gttttgccg aagcctgagg ccggctccgc tattagtgac        60
gtgtttgagg gccgcgaggt gtgccagcca aaacgaatcc ggccatttca tcctccagga     120
agtccatggg ccaaccgccc actccccgcc agcctcgcac caacaccaac cggtccagta     180
catgagccag tcgggtcact gaccccggca ccagtccctc agccactgga tccagcgccc     240
gcagtgactc ccgaggccag tcacctgttg gaggatcccg atgaagagac gagccaggct     300
gtcaaagccc ttcgggagat ggccgatact gtgattcccc agaaggaaga ggctgcaatc     360
tgtggccaaa tggacctttc ccatccgccc caaggggcc atctggatga gctgacaacc       420
acacttgagt ccatgaccga ggatctgaac ctggactcac ccctgacccc ggaattgaac     480
gagattctgg ataccttcct gaacgacgag tgcctcttgc atgccatgca tatcagcaca     540
ggactgtcca tcttcgacac atctctgttt                                       570

<210> SEQ ID NO 4
<211> LENGTH: 483
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gtgctgcctc aggctcctgc tcctgcacca gctccagcca tggtgtctgc actggctcag       60
gcaccagcac ccgtgcctgt gctggctcct ggacctccac aggctgtggc tccaccagcc     120
cctaaaccta cacaggccgg cgagggcaca ctgtctgaag ctctgctgca gctgcagttc     180
gacgacgagg atctgggagc cctgctggga aacagcaccg atcctgccgt gttcaccgac     240
ctggccagcg tggacaacag cgagttccag cagctgctga accagggcat ccctgtggcc     300
cctcacacca ccgagcccat gctgatggaa taccccgagg ccatcacccg gctcgtgaca     360
ggcgctcaga ggcctcctga tccagctcct gcccctctgg gagcaccagg cctgcctaat     420
ggactgctgt ctggcgacga ggacttcagc tctatcgccg atatggattt ctcagccttg     480
ctg                                                                    483

<210> SEQ ID NO 5
<211> LENGTH: 333
<212> TYPE: DNA
<213> ORGANISM: Artificial Sequence
<220> FEATURE:
<223> OTHER INFORMATION: Description of Artificial Sequence: Synthetic
```

```
polynucleotide

<400> SEQUENCE: 5
ctgtctgaag ctctgctgca gctgcagttc gacgacgagg atctgggagc cctgctggga      60
aacagcaccg atcctgccgt gttcaccgac ctggccagcg tggacaacag cgagttccag     120
cagctgctga accagggcat ccctgtggcc cctcacacca ccgagcccat gctgatggaa     180
taccccgagg ccatcacccg gctcgtgaca ggcgctcaga ggcctcctga tccagctcct     240 gccctctgg gagcaccagg cctgcctaat ggactgctgt ctggcgacga ggacttcagc     300
tctatcgccg atatggattt ctcagccttg ctg                                  333

<210> SEQ ID NO 6
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6 gccctcaca ccaccgagcc catgctgatg gaatacccg aggccatcac ccggctcgtg        60
acaggcgctc agaggcctcc tgatccagct cctgccctc tgggagcacc aggcctgcct     120
aatggactgc tgtctggcga cgaggacttc agctctatcg ccgatatgga tttctcagcc    180
ttgctg                                                                186

<210> SEQ ID NO 7
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
agccagtacc tgcccgacac cgacgaccgg caccggatcg aggaaaagcg gaagcggacc      60
tacgagacat tcaagagcat catgaagaag tccccttca gcggccccac cgaccctaga     120
cctccaccta gaagaatcgc cgtgcccagc agatccagcg ccagcgtgcc aaaacctgcc    180
ccccagcctt acccttcac cagcagcctg agcaccatca actacgacga gttccctacc     240
atggtgttcc ccagcggcca gatctctcag gcctctgctc tggctccagc ccctcctcag    300
gtgctgcctc aggctcctgc tcctgcacca gctccagcca tggtgtctgc actggctcag    360
gcaccagcac ccgtgcctgt gctggctcct ggacctccac aggctgtggc tccaccagcc    420
cctaaaccta cacaggccgg cgagggcaca ctgtctgaag ctctgctgca gctgcagttc    480
gacgacgagg atctgggagc cctgctggga aacagcaccg atcctgccgt gttcaccgac    540
ctggccagcg tggacaacag cgagttccag cagctgctga accagggcat ccctgtggcc    600

<210> SEQ ID NO 8
<211> LENGTH: 450
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
agccagtacc tgcccgacac cgacgaccgg caccggatcg aggaaaagcg gaagcggacc      60
```

```
tacgagacat tcaagagcat catgaagaag tccccttca gcggcccac cgaccctaga    120 cctccaccta gaagaatcgc cgtgcccagc agatccagcg ccagcgtgcc aaaacctgcc    180
ccccagcctt acccctcac cagcagcctg agcaccatca actacgacga gttccctacc    240
atggtgttcc ccagcggcca gatctctcag gcctctgctc tggctccagc ccctcctcag    300
gtgctgcctc aggctcctgc tcctgcacca gctccagcca tggtgtctgc actggctcag    360
gcaccagcac ccgtgcctgt gctggctcct ggacctccac aggctgtggc tccaccagcc    420
cctaaaccta cacaggccgg cgagggcaca    450
```

```
<210> SEQ ID NO 9
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
agccagtacc tgcccgacac cgacgaccgg caccggatcg aggaaaagcg gaagcggacc    60
tacgagacat tcaagagcat catgaagaag tccccttca gcggcccac cgaccctaga    120 cctccaccta gaagaatcgc cgtgcccagc agatccagcg ccagcgtgcc aaaacctgcc    180
ccccagcctt acccctcac cagcagcctg agcaccatca actacgacga gttccctacc    240
atggtgttcc ccagcggcca gatctctcag gcctctgctc tggctccagc ccctcctcag    300
```

```
<210> SEQ ID NO 10
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
agatccagcg ccagcgtgcc aaaacctgcc ccccagcctt acccctcac cagcagcctg    60 agcaccatca actacgacga gttccctacc atggtgttcc ccagcggcca gatctctcag    120
gcctctgctc tggctccagc ccctcctcag gtgctgcctc aggctcctgc tcctgcacca    180
gctccagcca tggtgtctgc actggctcag gcaccagcac ccgtgcctgt gctggctcct    240
ggacctccac aggctgtggc tccaccagcc cctaaaccta cacaggccgg cgagggcaca    300
```

```
<210> SEQ ID NO 11
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
ccactggatc cagcgcccgc agtgactccc gaggccagtc acctgttgga ggatcccgat    60
gaagagacga gccaggctgt caaagcccct cgggagatgg ccgatactgt gattccccag    120
aaggaagagg ctgcaatctg tggccaaatg gacctttccc atccgccccc aaggggccat    180
ctggatgagc tgacaaccac acttgagtcc atgaccgagg atctgaacct ggactcaccc    240 ctgacccccgg aattgaacga gattctggat accttcctga acgacgagtg cctcttgcat    300
gccatgcata tcagcacagg actgtccatc ttcgacacat ctctgtttt                 348
```

<210> SEQ ID NO 12
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gacctttccc atccgccccc aagggggccat ctggatgagc tgacaaccac acttgagtcc    60
atgaccgagg atctgaacct ggactcaccc ctgaccccgg aattgaacga gattctggat   120
accttcctga cgacgagtg cctcttgcat gccatgcata tcagcacagg actgtccatc    180
ttcgacacat ctctgttt                                                 198

<210> SEQ ID NO 13
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
agcctcgcac caacaccaac cggtccagta catgagccag tcgggtcact gaccccggca    60
ccagtccctc agccactgga tccagcgccc gcagtgactc ccgaggccag tcacctgttg   120
gaggatcccg atgaagagac gagccaggct gtcaaagccc ttcgggagat ggccgatact   180
gtgattcccc agaaggaaga ggctgcaatc tgtggccaaa tggacctttc ccatccgccc   240
ccaaggggcc atctggatga gctgacaacc acacttgagt ccatgaccga ggatctgaac   300
ctggactcac ccctgacccc ggaattgaac gagattctgg ataccttcct gaacgacgag   360
tgcctcttgc atgcc                                                    375

<210> SEQ ID NO 14
<211> LENGTH: 303
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
ccactggatc cagcgcccgc agtgactccc gaggccagtc acctgttgga ggatcccgat    60
gaagagacga gccaggctgt caaagccctt cgggagatgg ccgatactgt gattccccag   120
aaggaagagg ctgcaatctg tggccaaatg gacctttccc atccgccccc aaggggccat   180
ctggatgagc tgacaaccac acttgagtcc atgaccgagg atctgaacct ggactcaccc   240
ctgaccccgg aattgaacga gattctggat accttcctga cgacgagtg cctcttgcat    300 gcc                                                                 303

<210> SEQ ID NO 15
<211> LENGTH: 228
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gctgtcaaag cccttcggga gatggccgat actgtgattc cccagaagga agaggctgca    60

```
atctgtggcc aaatggacct ttcccatccg cccccaaggg gccatctgga tgagctgaca    120
accacacttg agtccatgac cgaggatctg aacctggact caccctgac cccggaattg     180 aacgagattc tggataccct cctgaacgac gagtgcctct tgcatgcc                 228
```

<210> SEQ ID NO 16
<211> LENGTH: 153
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
gacctttccc atccgccccc aagggcat ctggatgagc tgacaaccac acttgagtcc       60
atgaccgagg atctgaacct ggactcaccc ctgaccccgg aattgaacga gattctggat    120
accttcctga acgacgagtg cctcttgcat gcc                                 153
```

<210> SEQ ID NO 17
<211> LENGTH: 74
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Glu Ala Ser Gly Ser Gly Arg Ala Asp Ala Leu Asp Asp Phe Asp Leu
1               5                   10                  15

Asp Met Leu Gly Ser Asp Ala Leu Asp Asp Phe Asp Leu Asp Met Leu
            20                  25                  30

Gly Ser Asp Ala Leu Asp Asp Phe Asp Leu Asp Met Leu Gly Ser Asp
        35                  40                  45

Ala Leu Asp Asp Phe Asp Leu Asp Met Leu Ile Asn Ser Arg Ser Ser
    50                  55                  60

Gly Ser Pro Lys Lys Lys Arg Lys Val Gly
65                  70
```

<210> SEQ ID NO 18
<211> LENGTH: 261
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Ser Gln Tyr Leu Pro Asp Thr Asp Asp Arg His Arg Ile Glu Glu Lys
1               5                   10                  15

Arg Lys Arg Thr Tyr Glu Thr Phe Lys Ser Ile Met Lys Lys Ser Pro
            20                  25                  30

Phe Ser Gly Pro Thr Asp Pro Arg Pro Pro Arg Ile Ala Val
        35                  40                  45

Pro Ser Arg Ser Ser Ala Ser Val Pro Lys Pro Ala Pro Gln Pro Tyr
    50                  55                  60

Pro Phe Thr Ser Ser Leu Ser Thr Ile Asn Tyr Asp Glu Phe Pro Thr
65                  70                  75                  80

Met Val Phe Pro Ser Gly Gln Ile Ser Gln Ala Ser Ala Leu Ala Pro
            85                  90                  95
```

```
Ala Pro Pro Gln Val Leu Pro Gln Ala Pro Ala Pro Ala Pro
            100                 105                 110

Ala Met Val Ser Ala Leu Ala Gln Ala Pro Ala Pro Val Pro Val Leu
            115                 120                 125

Ala Pro Gly Pro Pro Gln Ala Val Ala Pro Pro Ala Pro Lys Pro Thr
        130                 135                 140

Gln Ala Gly Glu Gly Thr Leu Ser Glu Ala Leu Leu Gln Leu Gln Phe
145                 150                 155                 160

Asp Asp Glu Asp Leu Gly Ala Leu Leu Gly Asn Ser Thr Asp Pro Ala
                165                 170                 175

Val Phe Thr Asp Leu Ala Ser Val Asp Asn Ser Glu Phe Gln Gln Leu
            180                 185                 190

Leu Asn Gln Gly Ile Pro Val Ala Pro His Thr Thr Glu Pro Met Leu
        195                 200                 205

Met Glu Tyr Pro Glu Ala Ile Thr Arg Leu Val Thr Gly Ala Gln Arg
210                 215                 220

Pro Pro Asp Pro Ala Pro Ala Pro Leu Gly Ala Pro Gly Leu Pro Asn
225                 230                 235                 240

Gly Leu Leu Ser Gly Asp Glu Asp Phe Ser Ser Ile Ala Asp Met Asp
                245                 250                 255

Phe Ser Ala Leu Leu
            260

<210> SEQ ID NO 19
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Arg Asp Ser Arg Glu Gly Met Phe Leu Pro Lys Pro Glu Ala Gly Ser
1               5                   10                  15

Ala Ile Ser Asp Val Phe Glu Gly Arg Glu Val Cys Gln Pro Lys Arg
            20                  25                  30

Ile Arg Pro Phe His Pro Pro Gly Ser Pro Trp Ala Asn Arg Pro Leu
        35                  40                  45

Pro Ala Ser Leu Ala Pro Thr Pro Thr Gly Pro Val His Glu Pro Val
    50                  55                  60

Gly Ser Leu Thr Pro Ala Pro Val Pro Gln Pro Leu Asp Pro Ala Pro
65                  70                  75                  80

Ala Val Thr Pro Glu Ala Ser His Leu Leu Glu Asp Pro Asp Glu Glu
                85                  90                  95

Thr Ser Gln Ala Val Lys Ala Leu Arg Glu Met Ala Asp Thr Val Ile
            100                 105                 110

Pro Gln Lys Glu Glu Ala Ala Ile Cys Gly Gln Met Asp Leu Ser His
        115                 120                 125

Pro Pro Pro Arg Gly His Leu Asp Glu Leu Thr Thr Thr Leu Glu Ser
    130                 135                 140

Met Thr Glu Asp Leu Asn Leu Asp Ser Pro Leu Thr Pro Glu Leu Asn
145                 150                 155                 160

Glu Ile Leu Asp Thr Phe Leu Asn Asp Glu Cys Leu Leu His Ala Met
                165                 170                 175

His Ile Ser Thr Gly Leu Ser Ile Phe Asp Thr Ser Leu Phe
            180                 185                 190
```

<210> SEQ ID NO 20
<211> LENGTH: 161
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 20

Val Leu Pro Gln Ala Pro Ala Pro Ala Pro Ala Met Val Ser
1               5                   10                  15

Ala Leu Ala Gln Ala Pro Ala Pro Val Pro Val Leu Ala Pro Gly Pro
            20                  25                  30

Pro Gln Ala Val Ala Pro Pro Ala Pro Lys Pro Thr Gln Ala Gly Glu
        35                  40                  45

Gly Thr Leu Ser Glu Ala Leu Leu Gln Leu Gln Phe Asp Asp Glu Asp
    50                  55                  60

Leu Gly Ala Leu Leu Gly Asn Ser Thr Asp Pro Ala Val Phe Thr Asp
65                  70                  75                  80

Leu Ala Ser Val Asp Asn Ser Glu Phe Gln Gln Leu Leu Asn Gln Gly
                85                  90                  95

Ile Pro Val Ala Pro His Thr Thr Glu Pro Met Leu Met Glu Tyr Pro
            100                 105                 110

Glu Ala Ile Thr Arg Leu Val Thr Gly Ala Gln Arg Pro Pro Asp Pro
        115                 120                 125

Ala Pro Ala Pro Leu Gly Ala Pro Gly Leu Pro Asn Gly Leu Leu Ser
    130                 135                 140

Gly Asp Glu Asp Phe Ser Ser Ile Ala Asp Met Asp Phe Ser Ala Leu
145                 150                 155                 160

Leu

<210> SEQ ID NO 21
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 21

Met Ser Glu Ala Leu Leu Gln Leu Gln Phe Asp Asp Glu Asp Leu Gly
1               5                   10                  15

Ala Leu Leu Gly Asn Ser Thr Asp Pro Ala Val Phe Thr Asp Leu Ala
            20                  25                  30

Ser Val Asp Asn Ser Glu Phe Gln Gln Leu Leu Asn Gln Gly Ile Pro
        35                  40                  45

Val Ala Pro His Thr Thr Glu Pro Met Leu Met Glu Tyr Pro Glu Ala
    50                  55                  60

Ile Thr Arg Leu Val Thr Gly Ala Gln Arg Pro Pro Asp Pro Ala Pro
65                  70                  75                  80

Ala Pro Leu Gly Ala Pro Gly Leu Pro Asn Gly Leu Leu Ser Gly Asp
                85                  90                  95

Glu Asp Phe Ser Ser Ile Ala Asp Met Asp Phe Ser Ala Leu Leu
            100                 105                 110

<210> SEQ ID NO 22
<211> LENGTH: 62

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Pro His Thr Thr Glu Pro Met Leu Met Glu Tyr Pro Glu Ala Ile
1               5                   10                  15

Thr Arg Leu Val Thr Gly Ala Gln Arg Pro Pro Asp Pro Ala Pro Ala
            20                  25                  30

Pro Leu Gly Ala Pro Gly Leu Pro Asn Gly Leu Leu Ser Gly Asp Glu
        35                  40                  45

Asp Phe Ser Ser Ile Ala Asp Met Asp Phe Ser Ala Leu Leu
    50                  55                  60

<210> SEQ ID NO 23
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser Gln Tyr Leu Pro Asp Thr Asp Asp Arg His Arg Ile Glu Glu Lys
1               5                   10                  15

Arg Lys Arg Thr Tyr Glu Thr Phe Lys Ser Ile Met Lys Lys Ser Pro
            20                  25                  30

Phe Ser Gly Pro Thr Asp Pro Arg Pro Pro Arg Arg Ile Ala Val
        35                  40                  45

Pro Ser Arg Ser Ser Ala Ser Val Pro Lys Pro Ala Pro Gln Pro Tyr
    50                  55                  60

Pro Phe Thr Ser Ser Leu Ser Thr Ile Asn Tyr Asp Glu Phe Pro Thr
65                  70                  75                  80

Met Val Phe Pro Ser Gly Gln Ile Ser Gln Ala Ser Ala Leu Ala Pro
                85                  90                  95

Ala Pro Pro Gln Val Leu Pro Gln Ala Pro Ala Pro Ala Pro Ala Pro
            100                 105                 110

Ala Met Val Ser Ala Leu Ala Gln Ala Pro Ala Pro Val Pro Val Leu
        115                 120                 125

Ala Pro Gly Pro Pro Gln Ala Val Ala Pro Pro Ala Pro Lys Pro Thr
    130                 135                 140

Gln Ala Gly Glu Gly Thr Leu Ser Glu Ala Leu Leu Gln Leu Gln Phe
145                 150                 155                 160

Asp Asp Glu Asp Leu Gly Ala Leu Leu Gly Asn Ser Thr Asp Pro Ala
                165                 170                 175

Val Phe Thr Asp Leu Ala Ser Val Asp Asn Ser Glu Phe Gln Gln Leu
            180                 185                 190

Leu Asn Gln Gly Ile Pro Val Ala
        195                 200

<210> SEQ ID NO 24
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 24

Ser Gln Tyr Leu Pro Asp Thr Asp Arg His Arg Ile Glu Glu Lys
1               5                   10                  15

Arg Lys Arg Thr Tyr Glu Thr Phe Lys Ser Ile Met Lys Lys Ser Pro
            20                  25                  30

Phe Ser Gly Pro Thr Asp Pro Pro Pro Arg Arg Ile Ala Val
        35                  40                  45

Pro Ser Arg Ser Ser Ala Ser Val Pro Lys Pro Ala Pro Gln Pro Tyr
    50                  55                  60

Pro Phe Thr Ser Ser Leu Ser Thr Ile Asn Tyr Asp Glu Phe Pro Thr
65                  70                  75                  80

Met Val Phe Pro Ser Gly Gln Ile Ser Gln Ala Ser Ala Leu Ala Pro
                85                  90                  95

Ala Pro Pro Gln Val Leu Pro Gln Ala Pro Ala Pro Ala Pro Ala Pro
            100                 105                 110

Ala Met Val Ser Ala Leu Ala Gln Ala Pro Ala Pro Val Pro Val Leu
        115                 120                 125

Ala Pro Gly Pro Pro Gln Ala Val Ala Pro Pro Ala Pro Lys Pro Thr
    130                 135                 140

Gln Ala Gly Glu Gly Thr
145                 150

<210> SEQ ID NO 25
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser Gln Tyr Leu Pro Asp Thr Asp Arg His Arg Ile Glu Glu Lys
1               5                   10                  15

Arg Lys Arg Thr Tyr Glu Thr Phe Lys Ser Ile Met Lys Lys Ser Pro
            20                  25                  30

Phe Ser Gly Pro Thr Asp Pro Arg Pro Pro Arg Arg Ile Ala Val
        35                  40                  45

Pro Ser Arg Ser Ser Ala Ser Val Pro Lys Pro Ala Pro Gln Pro Tyr
    50                  55                  60

Pro Phe Thr Ser Ser Leu Ser Thr Ile Asn Tyr Asp Glu Phe Pro Thr
65                  70                  75                  80

Met Val Phe Pro Ser Gly Gln Ile Ser Gln Ala Ser Ala Leu Ala Pro
                85                  90                  95

Ala Pro Pro Gln
            100

<210> SEQ ID NO 26
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Arg Ser Ser Ala Ser Val Pro Lys Pro Ala Pro Gln Pro Tyr Pro Phe
1               5                   10                  15

Thr Ser Ser Leu Ser Thr Ile Asn Tyr Asp Glu Phe Pro Thr Met Val

```
            20                  25                  30

Phe Pro Ser Gly Gln Ile Ser Gln Ala Ser Ala Leu Ala Pro Ala Pro
        35                  40                  45

Pro Gln Val Leu Pro Gln Ala Pro Ala Pro Ala Pro Ala Pro Ala Met
    50                  55                  60

Val Ser Ala Leu Ala Gln Ala Pro Ala Pro Val Pro Val Leu Ala Pro
65                  70                  75                  80

Gly Pro Pro Gln Ala Val Ala Pro Pro Ala Pro Lys Pro Thr Gln Ala
                85                  90                  95

Gly Glu Gly Thr
            100

<210> SEQ ID NO 27
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Pro Leu Asp Pro Ala Pro Ala Val Thr Pro Glu Ala Ser His Leu Leu
1               5                   10                  15

Glu Asp Pro Asp Glu Glu Thr Ser Gln Ala Val Lys Ala Leu Arg Glu
            20                  25                  30

Met Ala Asp Thr Val Ile Pro Gln Lys Glu Glu Ala Ala Ile Cys Gly
        35                  40                  45

Gln Met Asp Leu Ser His Pro Pro Arg Gly His Leu Asp Glu Leu
    50                  55                  60

Thr Thr Thr Leu Glu Ser Met Thr Glu Asp Leu Asn Leu Asp Ser Pro
65                  70                  75                  80

Leu Thr Pro Glu Leu Asn Glu Ile Leu Asp Thr Phe Leu Asn Asp Glu
                85                  90                  95

Cys Leu Leu His Ala Met His Ile Ser Thr Gly Leu Ser Ile Phe Asp
            100                 105                 110

Thr Ser Leu Phe
        115

<210> SEQ ID NO 28
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Leu Ser His Pro Pro Arg Gly His Leu Asp Glu Leu Thr Thr Thr
1               5                   10                  15

Thr Leu Glu Ser Met Thr Glu Asp Leu Asn Leu Asp Ser Pro Leu Thr
            20                  25                  30

Pro Glu Leu Asn Glu Ile Leu Asp Thr Phe Leu Asn Asp Glu Cys Leu
        35                  40                  45

Leu His Ala Met His Ile Ser Thr Gly Leu Ser Ile Phe Asp Thr Ser
    50                  55                  60

Leu Phe
65
```

```
<210> SEQ ID NO 29
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser Leu Ala Pro Thr Pro Thr Gly Pro Val His Glu Pro Val Gly Ser
1               5                   10                  15

Leu Thr Pro Ala Pro Val Pro Gln Pro Leu Asp Pro Ala Pro Ala Val
                20                  25                  30

Thr Pro Glu Ala Ser His Leu Leu Glu Asp Pro Asp Glu Glu Thr Ser
            35                  40                  45

Gln Ala Val Lys Ala Leu Arg Glu Met Ala Asp Thr Val Ile Pro Gln
50                  55                  60

Lys Glu Glu Ala Ala Ile Cys Gly Gln Met Asp Leu Ser His Pro Pro
65                  70                  75                  80

Pro Arg Gly His Leu Asp Glu Leu Thr Thr Thr Leu Glu Ser Met Thr
                85                  90                  95

Glu Asp Leu Asn Leu Asp Ser Pro Leu Thr Pro Glu Leu Asn Glu Ile
            100                 105                 110

Leu Asp Thr Phe Leu Asn Asp Glu Cys Leu Leu His Ala
        115                 120                 125

<210> SEQ ID NO 30
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Pro Leu Asp Pro Ala Pro Ala Val Thr Pro Glu Ala Ser His Leu Leu
1               5                   10                  15

Glu Asp Pro Asp Glu Glu Thr Ser Gln Ala Val Lys Ala Leu Arg Glu
                20                  25                  30

Met Ala Asp Thr Val Ile Pro Gln Lys Glu Glu Ala Ala Ile Cys Gly
            35                  40                  45

Gln Met Asp Leu Ser His Pro Pro Arg Gly His Leu Asp Glu Leu
50                  55                  60

Thr Thr Thr Leu Glu Ser Met Thr Glu Asp Leu Asn Leu Asp Ser Pro
65                  70                  75                  80

Leu Thr Pro Glu Leu Asn Glu Ile Leu Asp Thr Phe Leu Asn Asp Glu
                85                  90                  95

Cys Leu Leu His Ala
            100

<210> SEQ ID NO 31
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Val Lys Ala Leu Arg Glu Met Ala Asp Thr Val Ile Pro Gln Lys
1               5                   10                  15
```

Glu Glu Ala Ala Ile Cys Gly Gln Met Asp Leu Ser His Pro Pro
                20                  25                  30
Pro Arg Gly His Leu Asp Glu Leu Thr Thr Thr Leu Glu Ser Met Thr Glu
        35                  40                  45
Asp Leu Asn Leu Asp Ser Pro Leu Thr Pro Glu Leu Asn Glu Ile Leu
    50                  55                  60
Asp Thr Phe Leu Asn Asp Glu Cys Leu Leu His Ala
65                  70                  75

<210> SEQ ID NO 32
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Leu Ser His Pro Pro Arg Gly His Leu Asp Glu Leu Thr Thr
1               5                   10                  15
Thr Leu Glu Ser Met Thr Glu Asp Leu Asn Leu Asp Ser Pro Leu Thr
            20                  25                  30
Pro Glu Leu Asn Glu Ile Leu Asp Thr Phe Leu Asn Asp Glu Cys Leu
        35                  40                  45
Leu His Ala
    50

<210> SEQ ID NO 33
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tacttatata aggggtggg ggcgcgttcg tcctcagtcg cgatcgaaca ctcgagccga    60
gcagacgtgc ctacggaccg                                              80

<210> SEQ ID NO 34
<211> LENGTH: 256
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
taggtcttga aaggagtggg aattggctcc ggtgcccgtc agtgggcaga gcgcacatcg    60
cccacagtcc ccgagaagtt gggggagggg gtcggcaatt gatccggtgc ctagagaagg   120
tggcgcgggg taaactggga aagtgatgtc gtgtactggc tccgcctttt tcccgagggt   180
gggggagaac cgtatataag tgcagtagtc gccgtgaacg ttcttttttcg caacgggttt   240 gccgccagaa cacagg                                                   256

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic -continued

```
          oligonucleotide

<400> SEQUENCE: 35
aaataaaata cgaaatg                                                 17

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aaataaaata cgaaatgaaa taaaatacga aatg                              34

<210> SEQ ID NO 37
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aataaaatat ctttattttc attacatctg tgtgttggtt ttttgtgtg              49
```

METHODS OF MODULATING EXPRESSION OF TARGET NUCLEIC ACID SEQUENCES IN A CELL

RELATED APPLICATION DATA

This application claims priority to U.S. Provisional Application No. 62/470,538 filed on Mar. 13, 2017, which is hereby incorporated herein by reference in its entirety for all purposes.

STATEMENT OF GOVERNMENT INTERESTS

This invention was made with government support under Grant No. 2012143331 awarded by the National Science Foundation and under Grant Nos. HG005550 and HG008525 awarded by the National Institutes of Health. The government has certain rights in the invention.

FIELD

The present invention relates in general to methods of modulating expression of a target nucleic acid sequence in a cell such as by using a compact AAV CRISPR system.

BACKGROUND

Methods of modulating expression of a target nucleic acid sequence in a cell are known. The CRISPR-Cas system has recently been developed as a flexible tool for modulating expression of target nucleic acid sequences in a cell. In one regard, the RNA-guided bacterial nuclease Cas9 can be reengineered as a programmable transcription factor by a series of modifications to the Cas9 protein including the direct fusion of modified Cas9 protein to a synthetic transcriptional activation domain (AD).[1-5] However, the modest levels of gene activation achieved by the first generation Cas9 activators have limited their potential applications.[6,7] A versatile, improved transcriptional regulator through the rational design of a tripartite activator, VP64-p65-RTA (VPR), fused to Cas9 was developed.[8] This Cas9-tripartite activator has been demonstrated in activating expression of endogenous coding and non-coding genes, such as in stimulating neuronal differentiation of induced pluripotent stem cells (iPSCs), and having the ability to target several genes simultaneously.

Numerous zinc fingers (ZFs) and transcriptional activator like effectors (TALEs) have been fused to effector domains in order to programmably target and activate, repress, or epigenetically modify endogenous genes, laying the foundation for precision regulation of epigenetic state[9-16]. Unfortunately, inefficient production pipelines prevent widespread use of these tools. For example, ZFs engineered to target an arbitrary sequence must be constructed in large oligonucleotide pool arrays that are expensive, labor-intensive to generate, and are not guaranteed to be specific to the intended sequence[17,18]. Similarly, TALEs, while a powerful platform, pose a significant challenge for assembly, sequence verification, and genetic stability due to their highly repetitive nature. Modern methods have managed to automate labor-intensive steps of construction[19]. Yet, even with an automated approach, the construction of a TALE library designed to target every protein coding locus in the human genome would require over 1 million dollars and 200 days[19].

Recently discovered, CRISPR-Cas systems have provided a quantum leap forward for programmable DNA-binding tools. In nature, CRISPR-Cas systems serve as archaeal and bacterial immune systems[20-25]. Although five different types of CRISPR-Cas systems have been discovered to date, the type II system has almost exclusively been used due to the small number of components required for DNA-targeting[26]. Programmable DNA-targeting by the type II CRISPR-Cas system only requires three components: Cas9 nuclease, CRISPR RNA (crRNA), and trans-activating crRNA (tracrRNA)[27-30].

To initiate programmed DNA targeting, Cas9 binds both crRNA and tracrRNA in an RNA-duplex. The first 20 nucleotides of the crRNA guide Cas9 to cleave any complementary genomic sequence located next to a short protospacer adjacent motif (PAM)[31,32]. A convenient fusion of the crRNA and tracrRNA produces a chimeric single guide RNA (sgRNA) that is sufficient to target Cas9 as well.[27]

Sequence specific sgRNAs are quick and easy to construct[33], and scaling up to produce tens of thousands of sgRNAs is a straightforward process. Today, a library of sgRNAs targeting every protein coding locus in the human genome can be constructed via chip-based oligonucleotide synthesis for roughly 5 thousand dollars, within a few weeks[33-35]. As such, the two component Cas9 and sgRNA system has been adopted as the standard genome editing tool for a wide range of organisms[27,36,37].

Following the widespread adoption of Cas9 as a programmable tool for genome editing, mutated Cas9 involving residues in DNA cleavage located within each of two nuclease domains of Cas9 have been developed[2,27]. Mutation of these catalytic residues generated a nuclease-null 'dead' Cas9 (dCas9) variant, disabling its ability to cleave DNA, while retaining the ability to bind DNA in a sequence specific manner. Fusion of the dCas9 protein to effector domains, such as transcription enhancing factors, repressors, and epigenetic modulators, has enabled unprecedented ease of eukaryotic transcriptome and epigenome manipulation.

Beyond applications to cellular programming, Cas9 transcriptional and epigenetic activators hold tremendous promise for in vivo gain of function studies as well as therapeutics. However, the most convenient and only approved vector for human delivery is the Adeno-associated Virus (AAV). This convenient virus allows for targeting of various tissue types with high efficiency and little risk of integration or immunogenicity. Unfortunately, the virus is limited to a genomic payload of 4.7 kb, which can be pushed to 5 kb but not much further. The most commonly used Cas9 ortholog from S. pyogenes is 4.2 kb alone, leaving very little room for an additional promoter let alone an sgRNA expression cassette or accessory activation domains. Therefore, there is a continuing need for efficient methods and effective vector systems that allow precise manipulation of transcriptional and epigenetic state of a target nucleic acid sequence in a cell.

SUMMARY

According to one aspect, the present disclosure provides a method of modulating expression of a target nucleic acid sequence in a cell. In one embodiment, the method includes introducing into the cell a nucleic acid sequence encoding a Cas9 protein and a guide RNA, wherein the Cas9 protein and the guide RNA are expressed and co-localize at a target site and modulate the expression of the target nucleic acid sequence. According to another aspect, a method of modulating expression of a target nucleic acid sequence in a cell is provided. In one embodiment, the method comprises introducing into the cell a nucleic acid sequence encoding a Cas9 fusion protein and a guide RNA, wherein the Cas9 fusion protein comprises Cas9 fused with at least one modified activation domain of VP64, p65 or RTA, or Cas9 fused with a combination of at least two modified activation domains of VP64, p65 and RTA, wherein the Cas9 fusion protein and the guide RNA are expressed and co-localize at a target site and modulate the expression of the target nucleic acid sequence.

In some embodiments, the Cas9 protein comprises Cas9 orthologs from *Streptococcus pyogenes* (Sp), *Streptococcus thermophiles* (St1), and *Staphylococcus aureus* (Sa). In one embodiment, the guide RNA is a chimeric single guide RNA (sgRNA). In an exemplary embodiment, the Cas9 protein is further fused with a transcriptional regulator. In some embodiments, the transcriptional regulator comprises a transcriptional activator, a transcriptional repressor or an epigenetic modifier. In other embodiments, the transcriptional activator comprises functional domains of multiple activators fused together. In some embodiments, the transcriptional activator comprises functional domains of VP64, p65, RTA or their various fusion combinations. In an exemplary embodiment, the transcriptional activator is a tripartite VP64-p65-RTA (VPR) activator. In some embodiments, the Cas9 is a Cas9 nickase or a nuclease null Cas9 (dCas9). In one embodiment, expression of Cas9 protein is inducible. In one embodiment, the Cas9 coding sequence is flanked by a promoter sequence at its 5' end and a terminator sequence at its 3' end. In an exemplary embodiment, the nucleic acid sequence encoding the Cas9 protein and the guide RNA are included on a single vector. In one embodiment, the single vector is packaged in a recombinant AAV (rAAV). In some embodiments, expression of a plurality of target nucleic acid sequences can be modulated. In one embodiment, the promoter sequence is truncated to reduce its length. In some embodiments, the promoter sequence comprises SCP1 (Super Core Promoter 1) promoter, EFS (Elongation Factor Short) promoter, or a CMV (Cytomegalovirus) promoter. In other embodiments, the terminator sequence is truncated to reduce its length. In some embodiments, the terminator sequence comprises a short 17nt sNRP-1, a 34nt dual sNRP-1, a 50nt synthetic, or a 250 nt bGHR terminator. In some embodiments, the rAAV is tissue specific. In one embodiment, the cell is from an embryo. In other embodiments, the cell is a stem cell, zygote, or a germ line cell. In some embodiments, the stem cell is an embryonic stem cell or pluripotent stem cell. In one embodiment, the cell is a somatic cell. In another embodiment, the somatic cell is a eukaryotic cell. In one embodiment, the eukaryotic cell is an animal cell.

In certain embodiments, the nucleic acid sequence encoding the Cas9 fusion protein and the guide RNA are included on a single vector that is capable of being packaged into a recombinant AAV (rAAV). In other embodiments, the activation domain of VP64, p65 or RTA is modified by truncation to reduce length while retaining activity as a transcriptional activator. In certain other embodiments, the combination of modified activation domains of VP64, p65 and RTA comprises a tripartite VP64-p65-RTA (VPR) fusion wherein each of the activation domains of VP64, p65 and RTA is truncated. In one embodiment, the Cas9 is a nuclease null Cas9 (dCas9). In another embodiment, expression of the Cas9 fusion protein is inducible. In one embodiment, the Cas9 fusion protein coding sequence is flanked by a promoter sequence at its 5' end and a terminator sequence at its 3' end. In another embodiment, expression of a plurality of target nucleic acid sequences can be modulated. In one embodiment, the promoter sequence is truncated to reduce its length suitable for packaging into an rAAV. In exemplary embodiments, the promoter sequence comprises SCP1 (Super Core Promoter 1) promoter (SEQ ID NO: 33), EFS (Elongation Factor Short) promoter (SEQ ID NO: 34), or a CMV (Cytomegalovirus) promoter. In certain embodiments, the terminator sequence is truncated to reduce its length suitable for packaging into an rAAV. In other embodiments, the terminator sequence comprises a short 17nt sNRP-1 (SEQ ID NO: 35), a 34nt dual sNRP-1 (SEQ ID NO: 36), a 50nt synthetic (SEQ ID NO: 37), or a 250 nt bGHR terminator.

According to another aspect, the present disclosure provides a nucleic acid construct comprises nucleic acid sequences encoding a Cas9 protein and a guide RNA. In one embodiment, the guide RNA is a chimeric single guide RNA (sgRNA). In some embodiments, the Cas9 protein is further fused with a transcriptional regulator. In other embodiments, the transcriptional regulator comprises a transcriptional activator, a transcriptional repressor or an epigenetic modifier. In some embodiments, the transcriptional activator comprises functional domains of multiple activators fused together. In other embodiments, the transcriptional activator comprises functional domains of VP64, p65, RTA or their various fusion combinations. In an exemplary embodiment, the transcriptional activator is a tripartite VP64-p65-RTA (VPR) activator. In one embodiment, the Cas9 is a Cas9 nickase or a nuclease null Cas9 (dCas9). In exemplary embodiment, the Cas9 coding sequence is flanked by a promoter sequence at its 5' end and a terminator sequence at its 3' end. In certain embodiments, the promotor sequence is truncated to reduce its length. In other embodiments, the promoter sequence comprises SCP1 (Super Core Promoter 1) promoter, EFS (Elongation Factor Short) promoter, or a CMV (Cytomegalovirus) promoter. In some embodiments, the terminator sequence is truncated to reduce its length. In other embodiments, the terminator sequence comprises a short 17nt sNRP-1, a 34nt dual sNRP-1, a 50nt synthetic, or a 250 nt bGHR terminator. In one embodiment, the guide RNA and/or the Cas9 fusion protein is introduced into the cell.

According to still another aspect, the present disclosure provides a recombinant AAV (rAAV) comprising a nucleic acid construct comprising the nucleic acid sequences encoding the Cas9 protein and the guide RNA according to the embodiments of the disclosure. In some embodiments, the rAAV is tissue specific.

According to one aspect, the target nucleic acid sequence of the present disclosure includes genomic DNA, mitochondrial DNA, viral DNA, or exogenous DNA.

According to another aspect, the present disclosure provides a method of treating a disease of a subject comprising administering a therapeutically effective amount of a recombinant AAV(rAAV) in the subject in need thereof. In one embodiment, the rAAV comprises a nucleic acid sequence encoding a Cas9 protein or a Cas9 fusion protein and a guide RNA. In another embodiment, the Cas9 protein is fused with a transcriptional regulator and the guide RNA comprises complementary sequences to a target site. In one embodiment, the Cas9 fusion protein and the guide RNA are expressed and co-localize at a target site and modulate the expression of a target gene. In another embodiment, the transcriptional regulator comprises a transcriptional activator, a transcriptional repressor or an epigenetic modifier. In an exemplary embodiment, the transcriptional activator is a tripartite VP64-p65-RTA (VPR) activator. In one embodiment, the Cas9 is a nuclease null Cas9 (dCas9). In one embodiment, the disease is a monogenetic disease. In some embodiments, the monogenetic disease includes monogenetic muscle wasting diseases. In other embodiments, the monogenetic muscle wasting diseases comprise Nemaline Myopathy, Duchenne Muscular Dystrophy, and McArdle's Disease. In some embodiments, the target gene comprises the cardiac actin gene, the utrophin gene, and the brain glycogen phosphorylase gene. In other embodiments, expression of cardiac actin gene, utrophin gene, or brain glycogen phosphorylase gene of the subject is modulated.

According to one aspect, a nucleic acid construct is provided. In one embodiment, the nucleic acid construct comprises nucleic acid sequences encoding a Cas9 fusion protein and a guide RNA. In another embodiment, the guide RNA is a chimeric single guide RNA (sgRNA). In certain embodiments, the Cas9 fusion protein comprises Cas9 fused with at least one modified activation domain of VP64, p65 or RTA, or Cas9 fused with a combination of at least two modified activation domains of VP64, p65 and RTA. In some embodiments, the activation domain of VP64, p65 or RTA is modified by truncation to reduce length while retaining activity as a transcriptional activator. In certain embodiments, the combination of modified activation domains of VP64, p65 and RTA comprises a tripartite VP64-p65-RTA (VPR) fusion wherein each of the activation domains of VP64, p65 and RTA is truncated. In one embodiment, the Cas9 is a nuclease null Cas9 (dCas9). In other embodiment, the Cas9 fusion protein coding sequence is flanked by a promoter sequence at its 5' end and a terminator sequence at its 3' end. In certain embodiments, the promotor sequence is truncated to reduce its length suitable for packaging into an rAAV. In exemplary embodiments, the promoter sequence comprises a Super Core Promoter 1 (SCP1) (SEQ ID NO: 33), an Elongation Factor Short (EFS) promoter (SEQ ID NO: 34), or a Cytomegalovirus (CMV) promoter. In other embodiments, the terminator sequence is truncated to reduce its length suitable for packaging into an rAAV. In exemplary embodiments, the terminator sequence comprises a short 17nt sNRP-1 (SEQ ID NO: 35), a 34nt dual sNRP-1 (SEQ ID NO: 36), a 50nt synthetic (SEQ ID NO: 37), or a 250 nt bGHR terminator. In one embodiment, the modified activation domain of VP64 is encoded by nucleic acid sequence of SEQ ID NO: 1. In certain embodiments, the modified activation domain of p65 is encoded by nucleic acid sequence of SEQ ID NO: 2, SEQ ID NO: 4, SEQ ID NO: 5, SEQ ID NO: 6, SEQ ID NO: 7, SEQ ID NO: 8, SEQ ID NO: 9, or SEQ ID NO: 10, respectively. In other embodiments, the modified activation domain of RTA is encoded by nucleic acid sequence of SEQ ID NO: 3, SEQ ID NO: 11, SEQ ID NO: 12, SEQ ID NO: 13, SEQ ID NO: 14, SEQ ID NO: 15, or SEQ ID NO: 16, respectively.

According to one other aspect, a recombinant AAV comprising a nucleic acid comprising nucleic acid sequences encoding a Cas9 fusion protein and a guide RNA according to the various embodiments as disclosed herein is provided. In one embodiment, the AAV is tissue specific.

In one embodiment, the modified activation domain of VP64 comprises protein sequence of SEQ ID NO: 17, which is encoded by nucleic acid sequence of SEQ ID NO: 1. In another embodiment, the modified activation domain of p65 comprises p65 deletion protein. In certain embodiments, the p65 deletion protein comprises protein sequence of SEQ ID NO: 18, SEQ ID NO: 20, SEQ ID NO: 21, SEQ ID NO: 22, SEQ ID NO: 23, SEQ ID NO: 24, SEQ ID NO: 25, or SEQ ID NO: 26, which are encoded by nucleic acid sequence of SEQ ID NO: 2, SEQ ID NO: 4, SEQ ID NO: 5, SEQ ID NO: 6, SEQ ID NO: 7, SEQ ID NO: 8, SEQ ID NO: 9, or SEQ ID NO: 10, respectively. In one embodiment, the modified activation domain of RTA comprises RTA deletion protein. In certain embodiments, the RTA deletion protein comprises protein sequence of SEQ ID NO: 19, SEQ ID NO: 27, SEQ ID NO: 28, SEQ ID NO: 29, SEQ ID NO: 30, SEQ ID NO: 31, or SEQ ID NO: 32, which are encoded by nucleic acid sequence of SEQ ID NO: 3, SEQ ID NO: 11, SEQ ID NO: 12, SEQ ID NO: 13, SEQ ID NO: 14, SEQ ID NO: 15, or SEQ ID NO: 16, respectively.

In some embodiments, the Cas9 fusion protein comprises the activation domain of VP64 or its variants, the activation domain of p65 or its deletion variants, and/or the activation domain of RTA or its deletion variants.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 2A is a schematic diagram depicting that transcriptional activation via Cas9 was performed by fusing activation domains to the C-terminus of a nuclease-null dCas9 protein. The commonly used VP64 activator, along with VP64-p65, p65-Rta and the tripartite VPR activator consisting of VP64-p65-Rta activation domains fused in tandem to dCas9. FIG. 2B depicts the results of serial activation domain assemblies fused to dCas9 that were tested against a fluorescent reporter assay. Error bars median fluorescence±s.e.m. n=8 biological replicates. (*denotes significance of dCas9-VP64-p65-RTA over all constructs including reporter control P=<0.0001, dCas9-VP64 P=<0.0001, dCas9-VP64-p65 P=<0.0001, and dCas9-VP64-Rta P=0.0003.)

FIGS. 5A-5C depict that dCas9-VPR represents a highly potent cross-organismal activator: FIG. 5A. For each gene, 4 gRNAs were transfected into S2 cells, against the fly genes Cecal and Mtk. Data are shown as the mean±s.e.m (n=3 biological replicates). P values determined by two-tailed t-test (*multiplexed dCas9-VP64 or dCas9-VPR vs. mock control sample for each gene respectively Cecal $P=<1\times10^{-4}$, $P=<1\times10^{-4}$, Mtk $P=<1\times10^{-4}$, $P=<1\times10^{-4}$). FIG. 5B. For each gene, 4 sgRNAs were co-transformed into S. cerevisiae with activator against Gal7 and Hed1. (*multiplexed dCas9-VP64 or dCas9-VPR vs. mock control sample for each gene respectively Gal7 $P=<1\times10^{-4}$, $P=<1\times10^{-1}$, Hed1 $P=2\times10^{-4}$, $P=<1\times10^{-4}$.) FIG. 5C. For Actc1, 4 guides were transfected into Neuro-2A mouse cells targeting the mouse cardiac actin gene. (*multiplexed dCas9-VP64 or dCas9-VPR vs. mock control sample for each gene respectively mActc1 $P=2\times10^{-4}$, $P=<1\times10^{-4}$.)

FIG. 7A depicts results of serial truncations of the full length 261 amino acid (aa) p65 from the N terminus, C terminus, and both are fused to the C-terminus of dSpCas9. The retained aa positions of the new domain are indicated by range of numbers following the domain name. For example, p65 (100-261) indicates a truncated p65 domain with the first 99 aa removed, and the remaining domain retained. Each activator, containing full length p65 or each of the 7 truncated versions of the domain, are compared in a fluorescent reporter assay in HEK293T cells. Truncation of p65 to produce p65 (100-261) lowers activity a modest 3 fold, while allowing for a gain of 300 bp of sequence space. Error bars indicate median fluorescence±standard deviation. n=2 biological replicates. (*denotes significance of $P=<0.05$ of activator over reporter only control via one-tailed t-test.) FIG. 7B depicts results that removal of the first 125 aa of the RTA domain leads to a negligible 2 fold reduction in activity, while allowing for a gain of 375 bp of sequence space. Additional truncations retained activity while allowing for a reduction in length, including p65 (150-261) and RTA (75-190). Error bars indicate median fluorescence±standard deviation. n=2 biological replicates. (*denotes significance of $P=<0.05$ of activator over reporter only control via one-tailed t-test.) FIG. 7C depicts a schematic illustration of TADs (transcriptional activation domains) located within each protein.

FIG. 8A shows that both p65 and RTA in the synergistic VP64-p65-RTA activator are replaced with their respective truncated versions. The new set of smaller activators are targeted to the endogenous mouse Actc1 gene in Neuro-2A cells. The VP64-p65-RTA(75-190), VP64-p65 (100-261)-RTA (75-190), and VP64-p65(100-261)-RTA (125-190) show no significant loss in potency compared to the full length VP64-p65-RTA activator. The smallest activator that retains potency, VP64-p65(100-261)-RTA(125-190), affords a 675 bp gain in sequence space. FIG. 8B shows that the new set of activators are targeted to the endogenous mouse Acta1 gene in Neuro-2A cells. Both VP64-p65(75-261)-RTA(75-190) and VP64-p65(100-261)-RTA(125-190) show a surprising and significant increase in potency over the full length VP65-p65-RTA activator. FIG. 8C shows that the new set of activators are targeted to the endogenous mouse Hbb gene in Neuro-2A cells. Four of the seven novel activators show no significant loss in activity relative to the full length activator, including the smallest new tool, VP64-p65(100-261)-RTA(125-190). Error bars indicate mean expression±standard deviation. n=2 biological replicates. (*denotes significance of $P=<0.05$ of activator when compared to full length activator via one-tailed t-test, n.s. denotes no significance.)

FIGS. 9A-9D depict results of gene activation with dSa-VPR miniature vs dSa-VP64. FIG. 9A shows that both dSa-VP64 and the dSa-VPR miniature activator are targeted to the mouse Cdr1as lncRNA gene in Neuro-2A cells. The dSa-VPR miniature activator performs 36-fold better than the other small activator dSa-VP64, however the median is not significantly different from the median level of activation with dSa-VP64, due to a large variance. FIG. 9B shows that both tools are targeted to the mouse gene Neurog2 and dSa-VPR miniature performs 24× better than dSa-VP64. FIG. 9C shows that both tools are targeted to the mouse gene Actc1 and dSa-VPR miniature performs 1100× better than dSa-VP64. FIG. 9D shows that both tools are targeted to the mouse gene Hbb and dSa-VPR miniature performs 2100× better than dSa-VP64. Error bars indicate mean expression±standard deviation. n=2 biological replicates. (*denotes significance of $P=<0.05$ of dSa-VPR miniature over dSa-VP64 via one-tailed t-test.)

FIG. 10A shows that the dSa-VPR miniature activator is expressed off of a SCP1 (Super Core Promoter 1) promoter, EFS (Elongation Factor Short) promoter, or a CMV (Cytomegalovirus) promoter and targeted to the mouse gene Neurog2 in Neuro-2A cells. The targeted cells are assayed via qPCR for expression of the dSaCas. While SCP1 allows for an expression on level with CMV, the EFS promoter significantly enhances the amount of activator transcript present, compared to CMV. FIG. 10B shows the same population of cells in FIG. 10A are assayed for expression of the Neurog2 target gene, use of the SCP1 promoter reduces efficiency roughly two-fold relative to the CMV promoter, while the EFS promoter essentially maintains efficiency relative to CMV. FIG. 10C shows the set of three dSa-VPR miniature expression cassettes, driven by SCP1, EFS, or CMV, are targeted to the mouse gene Actc1. The cells are assayed for expression of the dSaCas9 via qPCR. No significant loss in expression is observed due to the use of SCP1 relative to CMV, and again, an enhancement in expression is observed due to the use of EFS to drive expression as opposed to CMV. FIG. 10D shows the same set of cells in FIG. 10C are assayed for expression of the target gene mNeurog2. Both the SCP1 and EFS driven activators show an enhancement in efficiency relative to the CMV driven cassette. Error bars indicate mean expression±standard deviation. n=2 biological replicates. (*denotes significance of P=<0.05 of a short promoter driven activator relative to the CMV driven cassette via one-tailed t-test. **denotes significance of P=<0.05, in the opposite direction, with the short promoter driven activator performing at a lower efficiency than the CMV driven cassette.)

FIG. 11A shows that each construct was targeted to the mouse Actc1 gene via transfection in to Neuro-2A cells, and compared to the commonly used bGHR signal via qPCR for presence of dSaCas9 transcript, 48 hours post transfection. Both the extremely short 1× sNRP-1 and 2× sNRP-1 terminators were able to stabilize transcript expression, albeit at a 5-fold reduction in transcript number relative to the bGHR signal. FIG. 11B shows that despite mediating a reduction in transcript number, the 1× sNRP-1 and 2× sNRP-1 poly adenylation signals enable a surprisingly 3-fold increase in target Actc1 expression, indicating that the lower transcript number does not necessarily reduce the efficiency of dSa-VPR miniature mediated activation of the target. FIG. 11C shows that similar to panel A, each construct is targeted to the mouse Hbb gene and compared for expression of the dSaCas9 transcript. Both the 1× sNRP-1 and 2× sNRP-1 terminators show a significant reduction in transcript number relative to the bGHR terminator. FIG. 11D shows that when the cells are assayed for target Hbb expression, there is no significant difference in target expression between the 3 short terminators and the bGHR signal. FIG. 11E shows that the constructs are targeted to the mouse gene Neurog2 and compared for dSaCas9 transcript expression. Again, a reduction in transcript number is observed with the 1× sNRP-1 and 2× sNRP-1 terminators, relative to the bGHR signal. FIG. 11F shows that yet when the cells are assayed for Neurog2 target expression, no significant difference is found in gene expression level between the 3 terminators compared to the bGHR signal. Error bars indicate mean expression±standard deviation. n=2 biological replicates. (*denotes significance of P=<0.05 of a short terminator mediated expression relative to bGHR via two-tailed t-test. **denotes significance of P=<0.05, in the opposite direction, with the short terminator stabilized activator expressing lower level than the bGHR stabilized tool.)

FIG. 12A shows that the new activator construct and the gold standard vector are targeted to the mouse Neurog2 gene in Neuro-2A cells. Vectors are transfected in to Neuro-2A cells, and assayed for target expression after 48 hours. The new design performs 44-fold better than the standard. FIG. 12B shows that both activators are targeted to the mouse Hbb gene, and the new design performs 645-fold better than the standard. FIG. 12C shows that the two tools are targeted to the mouse Actc1 gene, and the new design performs 380-fold better than the standard. Error bars indicate mean expression±standard deviation. n=2 biological replicates. (*denotes significance of P=<0.05 of improvement in target activation with the new design relative to the standard, via one-tailed t-test.)

FIG. 13A shows that the new single vector activator is targeted to mouse genes Actc1, Hbb, and Neurog2 via transfection in to mouse C2C12 mouse myocyte cells, and assayed for expression via qPCR after 48 hours. Additionally, one population of cells is assayed for dSaCas9 expression. The Actc1 gene is very highly expressed in C2C12s, therefore further activation is negligible. Yet, the other targets Hbb, and Neurog2 are highly induced. FIG. 13B shows that the novel tool is targeted to the three mouse genes in GC-1 spermatogonial cells. The Hbb gene is modestly up-regulated, while the other two genes Actc1, and Neurog2 are highly induced. FIG. 13C shows that the three genes are targeted in mouse Hepa 1-6 hepatocarcinoma cells; Actc1 is modestly up-regulated, Hbb is strongly induced, and Neurog2 is not detected. FIG. 13D shows that the three genes are targeted in mouse Neuro-2A cells and are all highly up-regulated, as previously observed. Preliminary data, n=1 replicates.

FIG. 14A shows qPCR of 7 different portions of the new activator tool, progressing from the 5' end to the 3' end of the packaged genome. Viral genomes are calculated via standard curves generated from standard qPCR curves produced from qPCR of cut vector standards, with known copy numbers of the new activator tool expression cassette. FIG. 14B shows electrophoresis agarose gel with SYBR Gold stain for single and double stranded DNA. Lane M is Log-2 ladder, lane 2 is 200 ng of cut vector (7 kb), lane 4 is 50 ng of cut vector (7 kb), lane 6 is 1 ng of cut vector (7 kb), lane 8 is 10^9 AAV-DJ viral particles packaged with mActc1 targeting Cas9 activator tool (5 kb, including ITRs), lane 10 is 10^9 AAV-DJ viral particles packaged with CAG-GFP expression cassette (3 kb, including ITRs.) Preliminary data, n=1 replicates.

FIG. 15A. Roughly 10^9 viral particles of the packaged activator tool in AAV-DJ are delivered to C2C12, Hepa 1-6, GC-1, and Neuro-2A cells, and assayed for target expression after 72 hours. As expected from transfection experiments, Actc1 cannot be further activated in C2C12 cells, is modestly activated in Hepa 1-6 cells, and significantly induced in GC-1 and Neuro-2A cells. FIG. 15B shows that the transduced cell populations are assayed for dSaCas9 expression, and high levels of transcript numbers were observed. FIG. 15C shows that similar levels of activator expression in transduced cells were observed, when the qPCR is targeted to the end of the activator transcript at the 3' end of RTA. Preliminary data, n=1 replicate. FIG. 15D shows that the experiment is repeated in GC-1 and N2A cells, but cells are collected at days 9 and 10 post transduction instead, respectively.

FIG. 16A shows that the apex tissue in all four samples was assayed for dSa payload gene expression, via qPCR. Samples displayed a wide range of expression, varying from 20 to 6000-fold expression above the negative control sample. FIG. 16B shows that samples were additionally assayed for target mHbb gene expression above background, and ranged from 560-21,000 fold expression above background detectable levels. Notably, target gene expression increased correlation with the respective amount of dSa gene expression detected for each sample.

DETAILED DESCRIPTION

Figure 1:
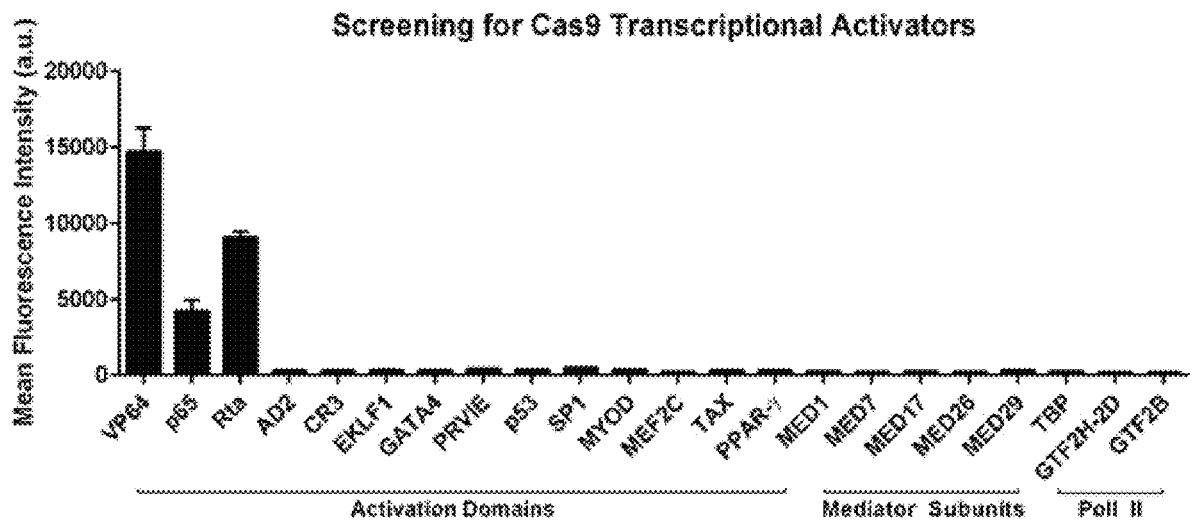
FIG. 1 depicts tripartite activator of VP64, p65 and RTA leads to the highest amounts of reporter activation when fused to dCas9. The transcriptional activation activity of the various dCas9 fusion proteins was quantified via a fluorescence reporter assay. The activation domain, mediator complex member or RNA polymerase subunit fused to the C-terminus of dCas9 is listed. The tested activation domains represent minimal activation domains. Mediator and RNA polymerase members fused to dCas9 were full length cDNAs. Data are shown as mean fluorescence+/−s.e.m. n=2 biological replicates.

Embodiments of the present disclosure provides methods and systems for modulating expression of a target nucleic acid sequence in a cell. According to one aspect, the present disclosure provides CRISPR based DNA targeting tools. In exemplary embodiments, a nucleic acid sequence encoding a Cas9 protein and a guide RNA is provided on a single vector, such as an engineered DNA plasmid vector. This vector is then packaged into a recombinant adeno-associated virus (rAAV) for delivery of the nucleic acid sequence encoding the Cas9 protein and the guide RNA into the desired cells or tissues. According to another aspect, the Cas9 is fused with transcriptional regulators or epigenetic modifiers. Once delivered into the cell, the Cas9 or Cas9 fusion protein and the guide RNA are expressed. The guide RNA comprises portion that is complementary to a sequence of a target site and guides the Cas9 or Cas9 fusion protein to the target site where expression of a target nucleic acid sequence can be modulated. Since the Cas9 will cleave the target nucleic acid sequence, a nuclease null Cas9 (dCas9) is employed to form fusion protein with a transcriptional regulator or an epigenetic modifier. In this manner, expression of the target nucleic acid sequence is modulated depending on the specific transcriptional regulator or epigenetic modifier fused with the dCas9. In one embodiments, the transcriptional regulator is a transcriptional activator. In another embodiment, the transcriptional regulator is a transcriptional repressor. In still another embodiment, the transcriptional regulator is an epigenetic modifier. In some embodiments, the transcriptional activator can be engineered to include functional domains of multiple activators fused together. In exemplary embodiments, the transcriptional activator includes functional domains of VP64, p65, RTA, or their various fusion combinations. In an exemplary embodiment, the transcriptional activator is a tripartite VP64-p65-RTA (VPR) activator.

Due to the payload size limit of the nucleic acid sequence that can be packaged into a rAAV, it is desirable to reduce the size of each of the component of the CRISPR system. In certain embodiments, the present disclosure provides that the small Cas9 orthologs are used. For example, small Cas9 orthologs from *Streptococcus thermophiles* (St1)[46] and *Staphylococcus aureus* (Sa)[49] are used in addition to the common Cas9 from *Streptococcus pyogenes* (Sp)[28]. According to one aspect, the Cas9 protein includes the sequence as set forth for naturally occurring Cas9 from *S. thermophiles* (St1), *S. aureus* (Sa) or *S. pyogenes* (Sp) and protein sequences having at least 20%, 30%, 40%, 50%, 60%, 70%, 80%, 90%, 95%, 98% or 99% homology thereto. Small Cas9 can also be engineered so that the non-essential regions of Cas9 is deleted while the functional regions of Cas9 is retained. Such engineering methods are known to a skilled in the art. According to one aspect, the engineered small Cas9 protein includes deletions or mutations of the naturally occurring Cas 9 (wild type) having protein sequences having at least 20%, 30%, 40%, 50%, 60%, 70%, 80%, 90%, 95%, 98% or 99% homology to the naturally occurring Cas9 from *S. thermophiles* (St1), *S. aureus* (Sa) or *S. pyogenes* (Sp) sequences as set forth. In other embodiments, the guide RNA can be reduced in size using engineering methods known to a skilled in the art. In an exemplary embodiment, a small sized chimeric single guide RNA (sgRNA) is employed[46, 49, 28]. According to one aspect, the guide RNA can be engineered from naturally occurring guide RNA sequence to reduce in size so that the non-essential regions of the guide RNA is deleted while the functional regions of the guide RNA is retained. The engineered small sized guide RNA include nucleic acid sequences having at least 20%, 30%, 40%, 50%, 60%, 70%, 80%, 90%, 95%, 98% or 99% homology to the naturally occurring guide RNA counterpart known in the art. The present disclosure provides engineered small guide RNAs that are used in a single vector with the nucleic acid sequence encoding the Cas9 protein for packaging into a rAAV. In some embodiments, the sizes of the promoter sequence and the terminator sequence flanking the Cas9 coding sequence are reduced for fitting into the rAAV. As used herein, a "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific or any combination thereof. A promoter drives expression or drives transcription of the nucleic acid sequence that it regulates. As used herein, a promoter is considered to be "operably linked" when it is in a correct functional location and orientation in relation to a nucleic acid sequence it regulates to control ("drive") transcriptional initiation and/or expression of that sequence. A promoter may be classified as strong or weak according to its affinity for RNA polymerase (and/or sigma factor); this is related to how closely the promoter sequence resembles the ideal consensus sequence for the polymerase. The strength of a promoter may depend on whether initiation of transcription occurs at that promoter with high or low frequency. Different promoters with different strengths may be used to engineer nucleic acids with different levels of gene/protein expression (e.g., the level of expression initiated from a weak promoter is lower than the level of expression initiated from a strong promoter). A promoter may be one naturally associated with a gene or sequence, as may be obtained by isolating the 5' non-coding sequences located upstream of the coding segment of a given gene or sequence. Such a promoter can be referred to as "endogenous." In some embodiments, "non-naturally occurring" promoter may be used. Such promoters may include promoters of other genes; promoters isolated from any other cell; and synthetic promoters or enhancers such as those that contain different elements of different transcriptional regulatory regions and/or mutations that alter expression through methods of genetic engineering that are known in the art. In some embodiments, small sized promoters may be used to fit into the packaging AAV. In other embodiments, short tissue specific promoters, either naturally occurring or engineered, may be used to optimize the delivery vectors and constructs for downstream in vivo applications. In some embodiments, the promoter sequence comprises an SCP1 (Super Core Promoter 1) promoter (SEQ ID NO: 33), an EFS (Elongation Factor Short) promoter (SEQ ID NO: 34), or a CMV (Cytomegalovirus) promoter. Other engineered or synthetic promoters of small size can also be used. According to one aspect, the engineered or synthetic promoters of small size include nucleic acid sequences having at least 20%, 30%, 40%, 50%, 60%, 70%, 80%, 90%, 95%, 98% or 99% homology to the SCP1 promoter (SEQ ID NO: 33) and EFS promoter (SEQ ID NO:

34), respectively. In other embodiments, the terminator sequence is truncated to reduce its length. In some embodiments, the terminator sequence comprises a short 17nt sNRP-1 (SEQ ID NO: 35), a 34nt dual sNRP-1 (SEQ ID NO: 36), a 50nt synthetic (SEQ ID NO: 37), or a 250 nt bGHR terminator. Other engineered or synthetic terminator sequences of small size can also be used. According to one aspect, the engineered or synthetic terminator sequences of small size include nucleic acid sequences having at least 20%, 30%, 40%, 50%, 60%, 70%, 80%, 90%, 95%, 98% or 99% homology to the short 17nt sNRP-1 (SEQ ID NO: 35), 34nt dual sNRP-1 (SEQ ID NO: 36), or 50nt synthetic (SEQ ID NO: 37), respectively.

According to another aspect, the present disclosure provides a single nucleic acid construct that includes the nucleic acid sequences encoding the Cas9 or Cas9 fusion protein and the guide RNA. In one embodiment, the single nucleic acid construct is an AAV expression plasmid vector which can be packaged into a rAAV according to methods known to a skilled in the art.

According to still another aspect, the present disclosure provides a recombinant AAV (rAAV) comprising a nucleic acid construct comprising the nucleic acid sequences encoding the Cas9 or Cas9 fusion protein and the guide RNA according to the embodiments of the disclosure. The present disclosure provides that the rAAV used is not limited to a certain type. Any type of AAV can be used based on the desired tissue or cell specificity. While AAV is able to infect many different cell or tissue types, the infection efficiency varies based upon serotype, which is determined by the sequence of the capsid protein. The present disclosure provides that native AAV serotypes 1-9 and engineered AAV systems such as AAV-DJ and AAV-DJ/8 can be used to provide tissue specific delivery of the compact CRISPR system according to the disclosure.

According to one aspect, the target nucleic acid sequence of the present disclosure includes genomic DNA, mitochondrial DNA, viral DNA, or exogenous DNA.

Cas9 Description

RNA guided DNA binding proteins are readily known to those of skill in the art to bind to DNA for various purposes. Such DNA binding proteins may be naturally occurring. DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety.

In general, bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. Science 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. *Journal of Bacteriology* 190, 1390 (February, 2008).

Three classes of CRISPR systems are generally known and are referred to as Type I, Type II or Type III). According to one aspect, a particular useful enzyme according to the present disclosure to cleave dsDNA is the single effector enzyme, Cas9, common to Type II. See K. S. Makarova et al., Evolution and classification of the CRISPR-Cas systems. *Nature reviews. Microbiology* 9, 467 (June, 2011) hereby incorporated by reference in its entirety. Within bacteria, the Type II effector system consists of a long pre-crRNA transcribed from the spacer-containing CRISPR locus, the multifunctional Cas9 protein, and a tracrRNA important for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9. TracrRNA-crRNA fusions are contemplated for use in the present methods.

According to one aspect, the enzyme of the present disclosure, such as Cas9 unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain aspects, different protospacer-adjacent motif can be utilized. For example, the *S. pyogenes* system requires an NGG sequence, where N can be any nucleotide. *S. thermophilus* Type II systems require NGGNG (see P. Horvath, R. Barrangou, CRISPR/Cas, the immune system of bacteria and archaea. Science 327, 167 (Jan. 8, 2010) hereby incorporated by reference in its entirety and NNAGAAW (see H. Deveau et al., Phage response to CRISPR-encoded resistance in *Streptococcus thermophilus*. *Journal of bacteriology* 190, 1390 (February, 2008) hereby incorporated by reference in its entirety), respectively, while different *S. mutans* systems tolerate NGG or NAAR (see J. R. van der Ploeg, Analysis of CRISPR in *Streptococcus mutans* suggests frequent occurrence of acquired immunity against infection by M102-like bacteriophages. *Microbiology* 155, 1966 (June, 2009) hereby incorporated by refernece in its entirety. Bioinformatic analyses have generated extensive databases of CRISPR loci in a variety of bacteria that may serve to identify additional useful PAMs and expand the set of CRISPR-targetable sequences (see M. Rho, Y. W. Wu, H. Tang, T. G. Doak, Y. Ye, Diverse CRISPRs evolving in human microbiomes. *PLoS genetics* 8, e1002441 (2012) and D. T. Pride et al., Analysis of streptococcal CRISPRs from human saliva reveals substantial sequence diversity within and between subjects over time. *Genome research* 21, 126 (January, 2011) each of which are hereby incorporated by reference in their entireties.

In *S. pyogenes,* Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinek et al., Science 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: *Methanococcus maripaludis* C7; *Corynebacterium diphtheriae; Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua; Lactobacillus casei; Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans; Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum; Mycoplasma mobile* 163K; *Mycoplasma penetrans; Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni doylei* 269 97; *Campylobacter jejuni* 81116; *Campylobacter jejuni; Campylobacter lari* RM2100; *Helicobacter hepaticus; Wolinella succinogenes; Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida; Francisella tularensis novicida* U112; *Francisella tularensis holarctica; Francisella tularensis* FSC 198; *Francisella tularensis tularensis; Francisella tularensis* WY96-3418; and *Treponema denticola* ATCC 35405. The Cas9 protein may be referred by one of skill in the art in the literature as Csn1. An exemplary *S. pyogenes* Cas9 protein sequence is provided in Deltcheva et al., Nature 471, 602-607 (2011) hereby incorporated by reference in its entirety.

Modification to the Cas9 protein is contemplated by the present disclosure. CRISPR systems useful in the present disclosure are described in R. Barrangou, P. Horvath, CRISPR: new horizons in phage resistance and strain identification. Annual review of food science and technology 3, 143 (2012) and B. Wiedenheft, S. H. Sternberg, J. A. Doudna, RNA-guided genetic silencing systems in bacteria and archaea. Nature 482, 331 (Feb. 16, 2012) each of which are hereby incorporated by reference in their entireties.

According to certain aspects, the DNA binding protein is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase. An exemplary DNA binding protein is an RNA guided DNA binding protein nuclease of a Type II CRISPR System, such as a Cas9 protein or modified Cas9 or homolog of Cas9. An exemplary DNA binding protein is a Cas9 protein nickase. An exemplary DNA binding protein is an RNA guided DNA binding protein of a Type II CRISPR System which lacks nuclease activity. An exemplary DNA binding protein is a nuclease-null or nuclease deficient Cas9 protein.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. See Jinek et al., *Science* 337, 816-821 (2012). According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10, H840, D839 and H863 substituted with an amino acid which reduces, substantially eliminates or eliminates nuclease activity, such as alanine, is referred to as a nuclease-null Cas9 ("Cas9Nuc") and exhibits reduced or eliminated nuclease activity, or nuclease activity is absent or substantially absent within levels of detection. According to this aspect, nuclease activity for a Cas9Nuc may be undetectable using known assays, i.e. below the level of detection of known assays.

According to one aspect, the Cas9 protein, Cas9 protein nickase or nuclease null Cas9 includes homologs and orthologs thereof which retain the ability of the protein to bind to the DNA and be guided by the RNA. According to one aspect, the Cas9 protein includes the sequence as set forth for naturally occurring Cas9 from *S. thermophiles, S. aureus* or *S. pyogenes* and protein sequences having at least 20%, 30%, 40%, 50%, 60%, 70%, 80%, 90%, 95%, 98% or 99% homology thereto and being a DNA binding protein, such as an RNA guided DNA binding protein.

An exemplary CRISPR system includes the *S. thermophiles* or *S. aureus* Cas9 nuclease (ST1 Cas9, Sa Cas9) (see Esvelt K M, et al., Orthogonal Cas9 proteins for RNA-guided gene regulation and editing, Nature Methods., (2013) hereby incorporated by reference in its entirety). An exemplary CRISPR system includes the *S. pyogenes* Cas9 nuclease (Sp. Cas9), an extremely high-affinity (see Sternberg, S. H., Redding, S., Jinek, M., Greene, E. C. & Doudna, J. A. DNA interrogation by the CRISPR RNA-guided endonuclease Cas9. *Nature* 507, 62-67 (2014) hereby incorporated by reference in its entirety), programmable DNA-binding protein isolated from a type II CRISPR-associated system (see Garneau, J. E. et al. The CRISPR/Cas bacterial immune system cleaves bacteriophage and plasmid DNA. *Nature* 468, 67-71 (2010) and Jinek, M. et al. A programmable dual-RNA-guided DNA endonuclease in adaptive bacterial immunity. *Science* 337, 816-821 (2012) each of which are hereby incorporated by reference in its entirety). According to certain aspects, a nuclease null or nuclease deficient Cas 9 can be used in the methods described herein. Such nuclease null or nuclease deficient Cas9 proteins are described in Gilbert, L. A. et al. CRISPR-mediated modular RNA-guided regulation of transcription in eukaryotes. Cell 154, 442-451 (2013); Mali, P. et al. CAS9 transcriptional activators for target specificity screening and paired nickases for cooperative genome engineering. *Nature biotechnology* 31, 833-838 (2013); Maeder, M. L. et al. CRISPR RNA-guided activation of endogenous human genes. *Nature methods* 10, 977-979 (2013); and Perez-Pinera, P. et al. RNA-guided gene activation by CRISPR-Cas9-based transcription factors. *Nature methods* 10, 973-976 (2013) each of which are hereby incorporated by reference in its entirety. The DNA locus targeted by Cas9 (and by its nuclease-deficient mutant, "dCas9" precedes a three nucleotide (nt) 5'-NGG-3' "PAM" sequence, and matches a 15-22-nt guide or spacer sequence within a Cas9-bound RNA cofactor, referred to herein and in the art as a guide RNA. Altering this guide RNA is sufficient to target Cas9 or a nuclease deficient Cas9 to a target nucleic acid. In a multitude of CRISPR-based biotechnology applications (see Mali, P., Esvelt, K. M. & Church, G. M. Cas9 as a versatile tool for engineering biology. *Nature methods* 10, 957-963 (2013); Hsu, P. D., Lander, E. S. & Zhang, F. Development and Applications of CRISPR-Cas9 for Genome Engineering. *Cell* 157, 1262-1278 (2014); Chen, B. et al. Dynamic imaging of genomic loci in living human cells by an optimized CRISPR/Cas system. *Cell* 155, 1479-1491 (2013); Shalem, O. et al. Genome-scale CRISPR-Cas9 knockout screening in human cells. *Science* 343, 84-87 (2014); Wang, T., Wei, J. J., Sabatini, D. M. & Lander, E. S. Genetic screens in human cells using the CRISPR-Cas9 system. *Science* 343, 80-84 (2014); Nissim, L., Perli, S. D., Fridkin, A., Perez-Pinera, P. & Lu, T. K. Multiplexed and Programmable Regulation of Gene Networks with an Integrated RNA and CRISPR/Cas Toolkit in Human Cells. *Molecular cell* 54, 698-710 (2014); Ryan, O. W. et al. Selection of chromosomal DNA libraries using a multiplex CRISPR system. *eLife* 3 (2014); Gilbert, L. A. et al. Genome-Scale CRISPR-Mediated Control of Gene Repression and Activation. *Cell* (2014); and Citorik, R. J., Mimee, M. & Lu, T. K. Sequence-specific antimicrobials using efficiently delivered RNA-guided nucleases. *Nature biotechnology* (2014) each of which are hereby incorporated by reference in its entirety), the guide is often presented in a so-called sgRNA (single guide RNA), wherein the two natural Cas9 RNA cofactors (gRNA and tracrRNA) are fused via an engineered loop or linker.

According to one aspect, the Cas9 protein is an enzymatically active Cas9 protein, a Cas9 protein wild-type protein, a Cas9 protein nickase or a nuclease null or nuclease deficient Cas9 protein. Additional exemplary Cas9 proteins include Cas9 proteins attached to, bound to or fused with functional proteins such as transcriptional regulators, such as transcriptional activators or repressors, a Fok-domain, such as Fok 1, an aptamer, a binding protein, PP7, MS2 or an epigenetic modifier and the like.

According to certain aspects, the Cas9 protein may be delivered directly to a cell by methods known to those of skill in the art, including injection or lipofection, or as translated from its cognate mRNA, or transcribed from its cognate DNA into mRNA (and thereafter translated into protein). Cas9 DNA and mRNA may be themselves introduced into cells through electroporation, transient and stable transfection (including lipofection) and viral transduction or other methods known to those of skill in the art. In exemplary embodiments, Cas9 coding DNA sequence is packaged into rAAV and delivered to cells in vivo or in vitro.

Guide RNA Description

Embodiments of the present disclosure are directed to the use of a CRISPR/Cas system and, in particular, a guide RNA which may include one or more of a spacer sequence, a tracr mate sequence and a tracr sequence. The term spacer sequence is understood by those of skill in the art and may include any polynucleotide having sufficient complementarity with a target nucleic acid sequence to hybridize with the target nucleic acid sequence and direct sequence-specific binding of a CRISPR complex to the target sequence. The guide RNA may be formed from a spacer sequence covalently connected to a tracr mate sequence (which may be referred to as a crRNA) and a separate tracr sequence, wherein the tracr mate sequence is hybridized to a portion of the tracr sequence. According to certain aspects, the tracr mate sequence and the tracr sequence are connected or linked such as by covalent bonds by a linker sequence, which construct may be referred to as a fusion of the tracr mate sequence and the tracr sequence. The linker sequence referred to herein is a sequence of nucleotides, referred to herein as a nucleic acid sequence, which connect the tracr mate sequence and the tracr sequence. Accordingly, a guide RNA may be a two component species (i.e., separate crRNA and tracr RNA which hybridize together) or a unimolecular species (i.e., a crRNA-tracr RNA fusion, often termed an sgRNA).

According to certain aspects, the guide RNA is between about 10 to about 500 nucleotides. According to one aspect, the guide RNA is between about 20 to about 100 nucleotides. According to certain aspects, the spacer sequence is between about 10 and about 500 nucleotides in length. According to certain aspects, the tracr mate sequence is between about 10 and about 500 nucleotides in length. According to certain aspects, the tracr sequence is between about 10 and about 100 nucleotides in length. According to certain aspects, the linker nucleic acid sequence is between about 10 and about 100 nucleotides in length.

According to one aspect, embodiments described herein include guide RNA having a length including the sum of the lengths of a spacer sequence, tracr mate sequence, tracr sequence, and linker sequence (if present). Accordingly, such a guide RNA may be described by its total length which is a sum of its spacer sequence, tracr mate sequence, tracr sequence, and linker sequence (if present). According to this aspect, all of the ranges for the spacer sequence, tracr mate sequence, tracr sequence, and linker sequence (if present) are incorporated herein by reference and need not be repeated. A guide RNA as described herein may have a total length based on summing values provided by the ranges described herein. Aspects of the present disclosure are directed to methods of making such guide RNAs as described herein by expressing constructs encoding such guide RNA using promoters and terminators and optionally other genetic elements as described herein.

According to certain aspects, the guide RNA may be delivered directly to a cell as a native species by methods known to those of skill in the art, including injection or lipofection, or as transcribed from its cognate DNA, with the cognate DNA introduced into cells through electroporation, transient and stable transfection (including lipofection) and viral transduction. In exemplary embodiments, guide RNA coding sequence is packaged into rAAV and delivered to cells in vivo or in vitro.

Transcription Regulator Description

According to one aspect, an engineered Cas9-gRNA system is provided which enables RNA-guided DNA regulation in cells by tethering transcriptional activation/repression domains to either a nuclease-null Cas9 or to guide RNAs. According to one aspect of the present disclosure, one or more transcriptional regulatory proteins or domains (such terms are used interchangeably) are joined or otherwise connected to a nuclease-deficient Cas9 or one or more guide RNA (gRNA). The transcriptional regulatory domains correspond to targeted loci. Accordingly, aspects of the present disclosure include methods and materials for localizing transcriptional regulatory domains to targeted loci by fusing, connecting or joining such domains to either Cas9N or to the gRNA.

Foreign Nucleic Acids Description

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources. Foreign nucleic acid sequence may include donor nucleic acid sequence. The term "donor nucleic acid" include a nucleic acid sequence which is to be inserted into genomic DNA according to methods described herein. The donor nucleic acid sequence may be expressed by the cell. According to one aspect, the donor nucleic acid is exogenous to the cell. According to one aspect, the donor nucleic acid is foreign to the cell.

Cells

Cells according to the present disclosure include any cell into which foreign nucleic acids can be introduced and expressed as described herein. It is to be understood that the basic concepts of the present disclosure described herein are not limited by cell type. In some embodiments, the cell is from an embryo. The cell can be a stem cell, zygote, or a germ line cell. In embodiments where the cell is a stem cell, the stem cell is an embryonic stem cell or pluripotent stem cell. In other embodiments, the cell is a somatic cell. In embodiments, where the cell is a somatic cell, the somatic cell is a eukaryotic cell or prokaryotic cell. The eukaryotic cell can be an animal cell, such as from a pig, mouse, rat, rabbit, dog, horse, cow, non-human primate, human.

Vectors

Vectors are contemplated for use with the methods and constructs described herein. The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors may be plasmids, lentiviruses or adeno-associated viruses known to those of skill in the art. Vectors include, but are not limited to, nucleic acid molecules that are single-stranded, doublestranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Methods of non-viral delivery of nucleic acids or native DNA binding protein, native guide RNA or other native species include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term native includes the protein, enzyme or guide RNA species itself and not the nucleic acid encoding the species.

Regulatory Elements and Terminators and Tags

Regulatory elements are contemplated for use with the methods and constructs described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit (3-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein.

Aspects of the methods described herein may make use of epitope tags and reporter gene sequences. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, betaglucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

Delivery Description

Embodiments of the present disclosure are directed to a method of delivering a nucleic acid sequence encoding the Cas9 protein and guide RNA to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, the nucleic acid sequence that is packaged in rAAV.

Diseases and Conditions

Diseases and detrimental conditions may be characterized by abnormal loss of expression or underexpression of a particular protein or abnormal gain or overexpression of a particular protein. Such diseases or detrimental conditions can be treated by upregulation or down regulation of the particular protein. Accordingly, methods of treating a disease or detrimental condition are provided where the co-localization complex as described herein associates or otherwise binds to target DNA including a target nucleic acid, and the transcriptional activator of the co-localization complex upregulates expression of the target nucleic acid or the transcriptional repressor of the co-localization complex downregulates expression of the target nucleic acid. One of skill in the art will readily identify such diseases and detrimental conditions associated with target DNA based on the present disclosure.

Mutations in genomic DNA are known to result in alteration and pathological development in cellular function and diseases, as well as cancer, diabetes, cardiovascular diseases, neurodegenerative disorders, aging or genetic disorders (See, Alexeyev M. et al., The Maintenance of Mitochondrial DNA Integrity—Critical Analysis and Update, Cold Spring Harb Perspect Biol, (2013); 5:a012641). Accordingly, methods of treating a disease or detrimental condition are provided where foreign DNA is integrated into a target nucleic acid sequence of a eukaryotic cell via providing to the cell a guide RNA sequence complementary to a target nucleic acid sequence, providing to the cell a donor sequence, providing to the cell a Cas9 enzyme that interacts with the guide RNA sequence and cleaves the target nucleic acid sequence in a site specific manner, wherein the guide RNA sequence binds to the complementary target nucleic acid sequence and the Cas9 enzyme cleaves the target mitochondrial nucleic acid sequence in a site specific manner; and wherein the donor sequence is integrated into the nucleic acid sequence. In this manner, the mutation can be corrected by the donor sequence.

The following examples are set forth as being representative of the present disclosure. These examples are not to be construed as limiting the scope of the present disclosure as these and other equivalent embodiments will be apparent in view of the present disclosure, figures and accompanying claims.

EXEMPLIFICATION

Example I

Highly-Efficient Cas9-Mediated Transcriptional Programming 1.1 Identify Alternate Modular Activation Domains to VP64 Gold Standard To design an enhanced activator, a small library of transcription factor ADs and members of the mediator and RNA polymerase II complexes for potential use as transcriptional effectors were screened[42]. More than 20 individual candidates were fused to the C-terminus of *Streptococcus pyogenes* (SP)-dCas9. These putative dCas9-activator constructs were transfected into mammalian cells and their potency assessed by quantifying fluorescence from a transcriptional reporter by flow cytometry[2] (FIG. 1). Of the hybrid proteins tested, three—dCas9-VP64, dCas9-p65 and dCas9-Rta—showed meaningful reporter induction[1,43]. Nonetheless, neither the p65 nor the Rta hybrid were stronger activators than the commonly used dCas9-VP64 protein.

1.2 Engineer Activator with Improved Efficiency Over dCas9-VP64

Figure 2A:
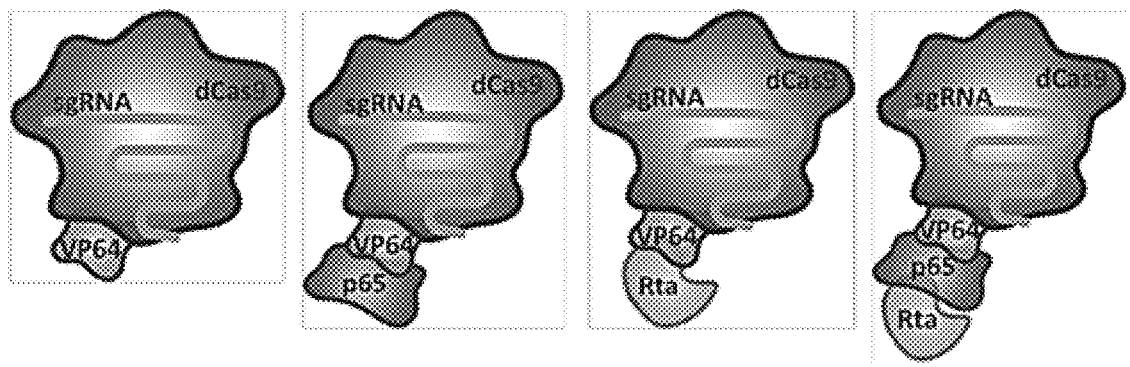
FIGS. 2A-2B depict that activation is improved by serial fusion of activation domains to dCas9.
Figure 2B:
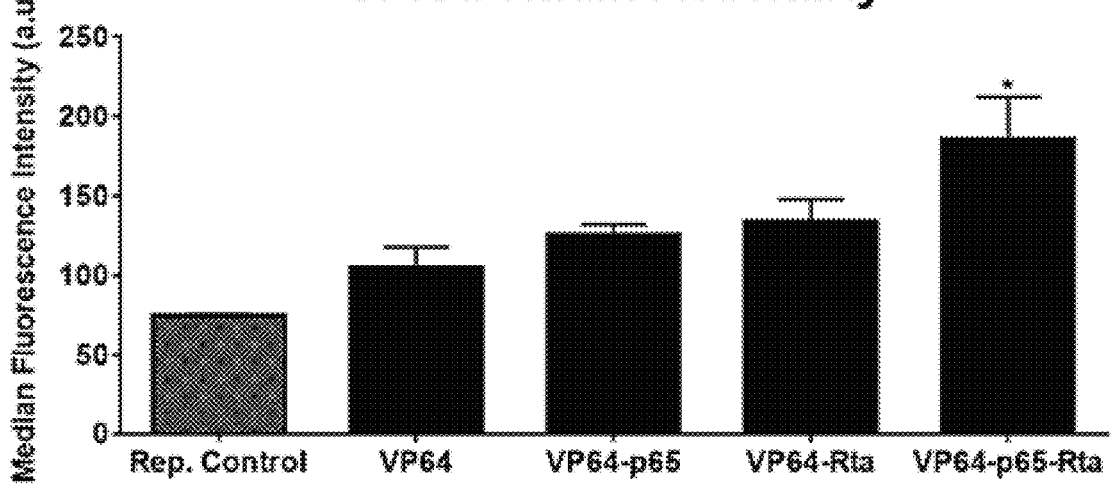

As neither of the most potent hybrid Cas9-ADs showed activity above the VP64 fusion, an alternative method could be found by taking advantage of the innately cooperative transcriptional mechanism which exists in nature. In natural systems, transcriptional initiation occurs through the coordinated recruitment of the necessary machinery by a group of locally concentrated transcription factor ADs[44]. Hence, it was hypothesized that joining multiple activation domains to a single dCas9 molecule would result in an increase in transcriptional activation by mimicking the natural cooperative recruitment process. Taking dCas9-VP64 as a starting scaffold, an additional nuclear localization signal/sequence was introduced to ensure efficient targeting. In some embodiments, the nuclear localization signal/sequence may be optimized to increase the targeting efficiency of the Cas9 and transcription activation fusion protein. The C-terminal fusion was subsequently extended with the addition of either the p65 or Rta AD. As predicted, when p65 or Rta was joined to dCas9-VP64, an increase in transcriptional output was observed. Further improvement was observed when both p65 and Rta were fused in tandem to VP64, generating a hybrid VP64-p65-Rta tripartite activator (hereinafter referred to as VPR) (FIGS. 2A & 2B).

To begin characterizing VPR, the importance of each of its constituent parts (VP64, p65, and Rta) was confirmed by replacing each member with mCherry and measuring the resulting protein's activity by reporter assay. All fusions containing mCherry showed a decrease in activity relative to VPR but exhibited higher levels of activity with respect to the VP64 activation domain alone, demonstrating the essentiality of all members of the VPR complex (data not shown). While the VPR fusion showed a clear improvement in transcriptional activation, the optimal ordering of the individual ADs remained unknown. To test the role of domain order, a set of dCas9-VPR constructs was designed in which the positions of VP64, p65, and Rta were shuffled to generate all possible non-repeating rearrangements. Evaluation of the VPR permutations confirmed that the original VP64-p65-Rta order was indeed the optimal configuration (data not shown).

Figure 3:
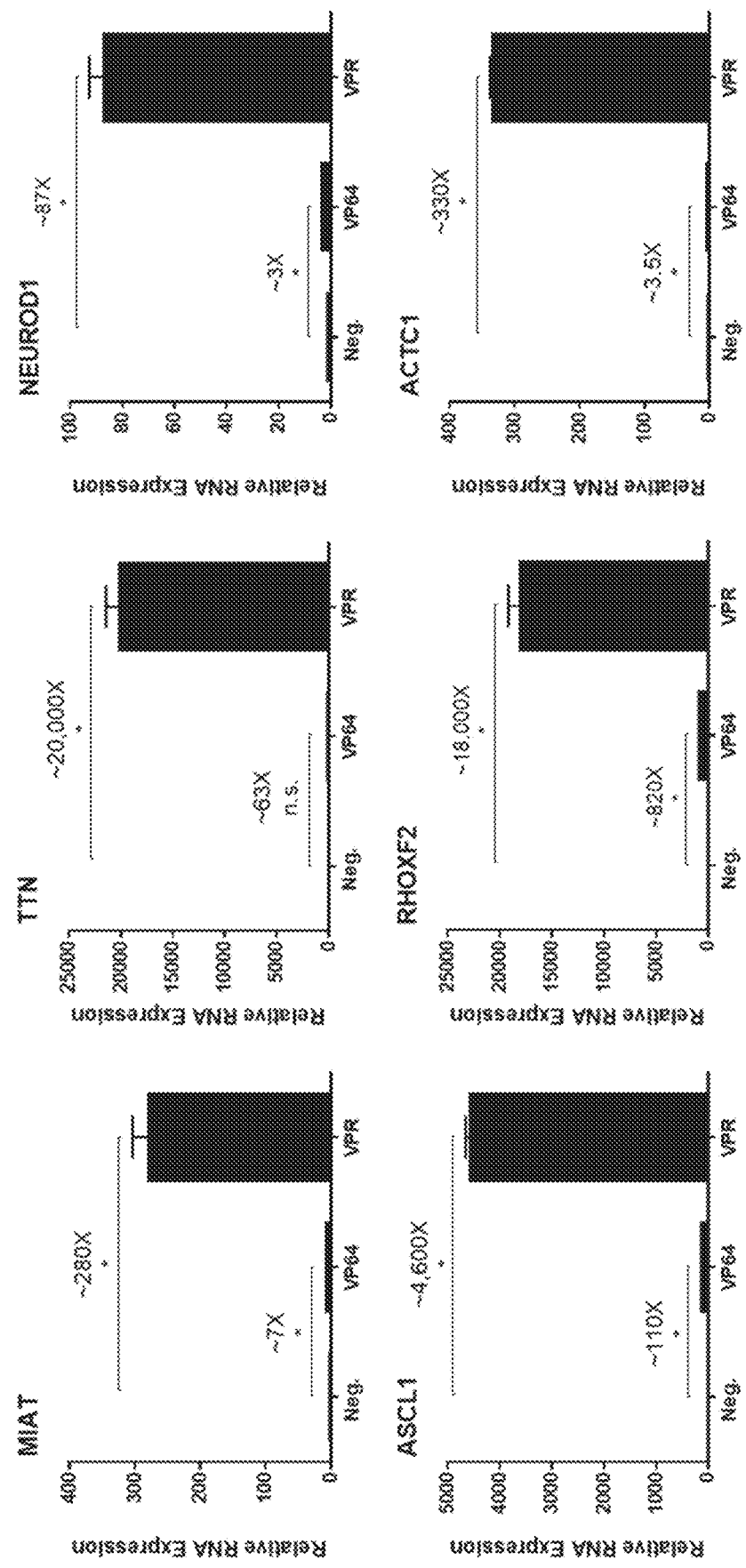
FIG. 3 depicts results demonstrating that VPR represents a robust tool for gene activation. Target gene expression, measured by qRT-PCR and normalized to Beta-actin mRNA levels, in HEK293T cells transfected with 3-4 gRNAs targeting the indicated genes along with the labeled dCas9-activator construct. Negative controls were transfected with indicated guide RNAs alone. Data are shown as the mean±s.e.m (n=3 biological replicates). Difference in activation between VPR and VP64 was 40-fold, 320-fold, 26-fold, 40-fold, 22-fold, 94-fold, and for MIAT, TTN, NEUROD1, RHOXF2, ASCL1, and ACTC1, respectively. P values determined by two-tailed t-test (*dCas9-VP64 or dCas9-VPR versus guide only control, respectively, MIAT P=0.0277, 0.001, TTN P=n.s., 0.0003, NEUROD1 P=0.0009, 0.0003, ASCL1 P=<0.0001, <0.0001, RHOXF2 P=<0.0001, 0.0002, ACTC1 P=0.0002, <0.0001. n.s.=not significant.)

1.3 Endogenous Gene Proof of Principle: ORFs, Largest Protein Coding Gene, and a Long Non-Coding RNA Having performed initial characterization of our SP-dCas9-VPR fusion, it was next sought to assess its ability to activate endogenous coding and non-coding targets relative to VP64. To this end, 3-4 gRNAs were constructed against a set of factors related to cellular reprogramming, development, and gene therapy. When compared to the dCas9-VP64 activator, dCas9-VPR showed 22-to-320 fold improved activation of endogenous targets. Induced genes include the long-noncoding RNA (lncRNA) MIAT, the largest protein-coding gene in the human genome, TTN, several transcription factors, NEUROD1, ASCL1, RHOXF2, and a structural protein, ACTC1 (FIG. 3).

1.4 Multiplex Activation

Figure 4:
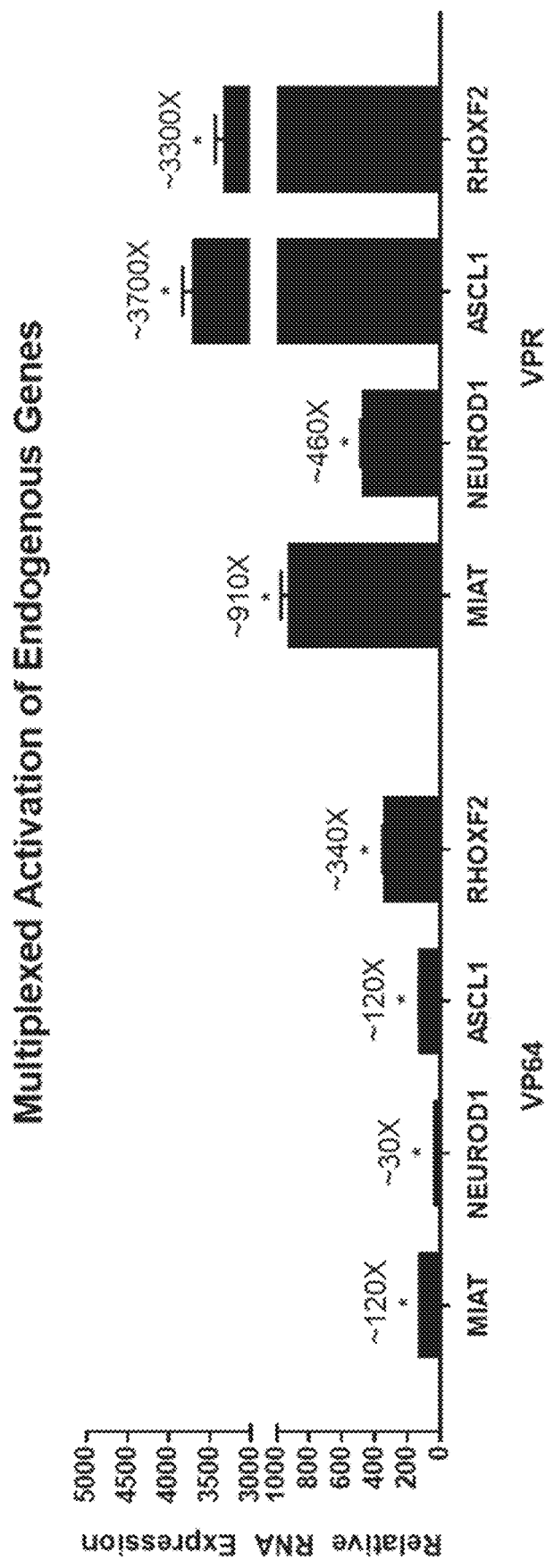
FIG. 4 depicts that VPR represents a robust tool for multiplexed gene activation. Performed as in FIG. 3, except 3-4 gRNAs against the four endogenous genes, MIAT, NEUROD1, ASCL1, and RHOXF2, were transfected in unison. Data are shown as the mean±s.e.m (n=3 biological replicates). P values determined by two-tailed t-test (*multiplexed dCas9-VP64 or dCas9-VPR vs. mock control sample for each gene respectively, MIAT $P=1.26\times10^{-5}$, $P=1.26\times10^{-4}$, NEUROD1 $P=7.28\times10^{-5}$, $P=4.72\times10^{-5}$, ASCL1 $P=5.82\times10^{-4}$, $P=1.50\times10^{-5}$, RHOXF2 $P=1.57\times10^{-5}$, $P=1.84\times10^{-5}$.)
Figure 6:
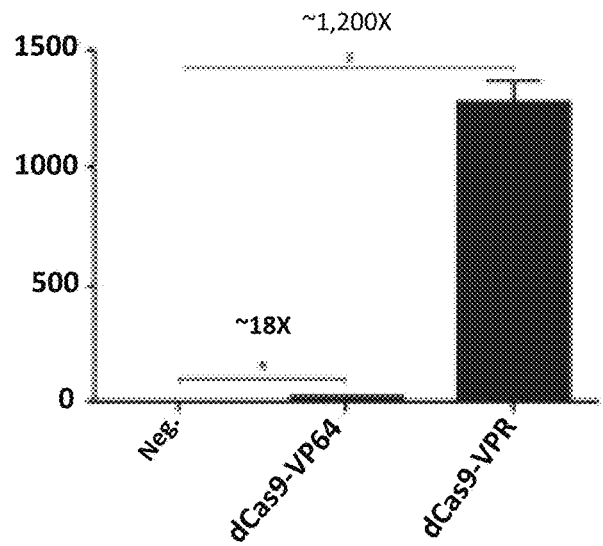
FIG. 6 depicts a comparison of VPR activity when fused to small Cas9 orthologs. Transcriptional activation via dCas9-VPR orthologs was performed by fusing a VPR activator to the C-terminus of three nuclease null dCas9 proteins, isolated from Streptococcus pyogenes (Sp), Streptococcus thermophiles (St1), and Staphylococcus aureus (Sa) respectively. Cas9 activator orthologs were compared in a fluorescent reporter assay in HEK293T cells. Replacement of dSpCas9 with dSaCas9 to create dSaCas9-VPR leads to a modest 1.8× hit in activity, with a gain of 1 kb of genomic sequence space. Error bars indicate median fluorescence±standard deviation. n=2 biological replicates. (*denotes significance of $P=<0.05$ of dCas9-VPR ortholog activation over respective reporter only control via one-tailed t-test.)
Figure 6:
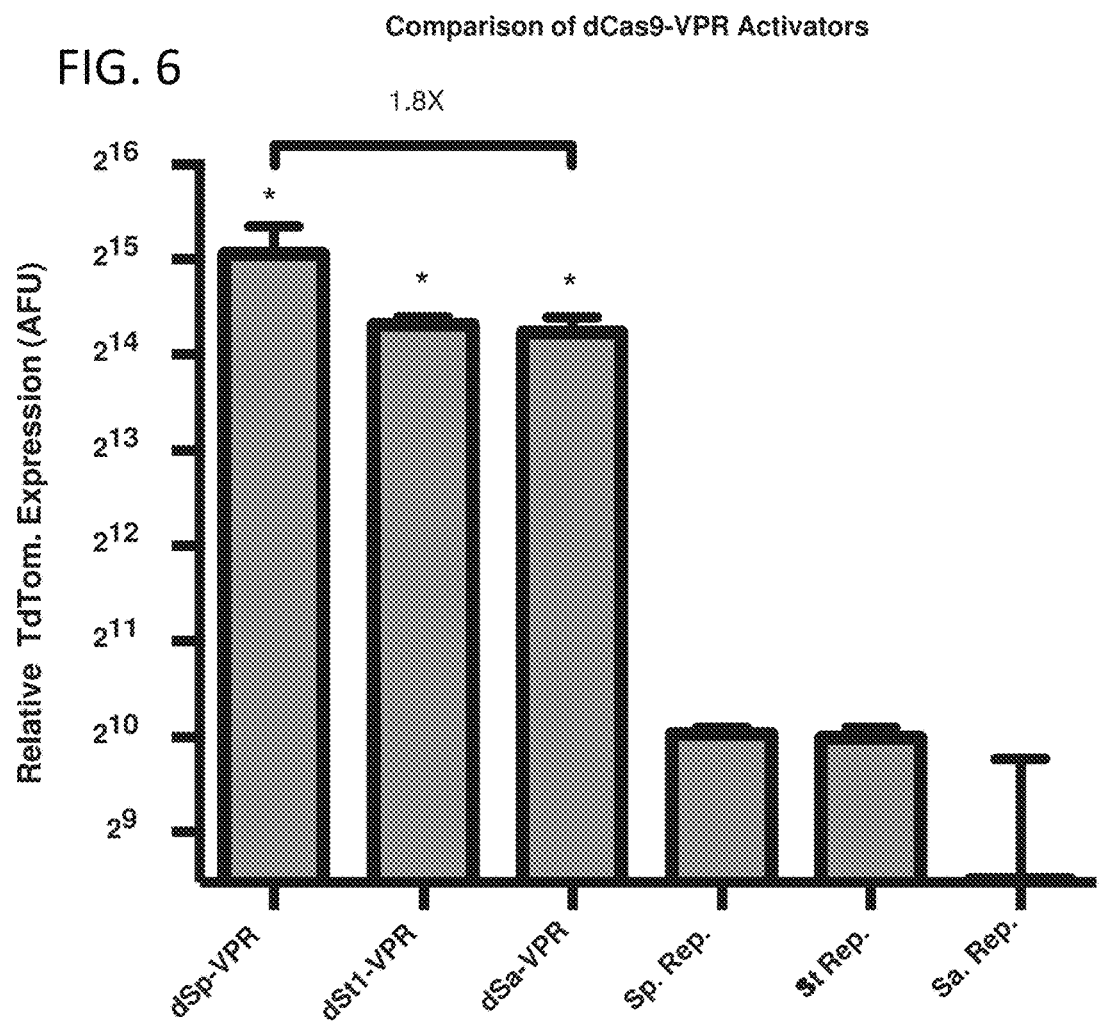
Figure 7A:
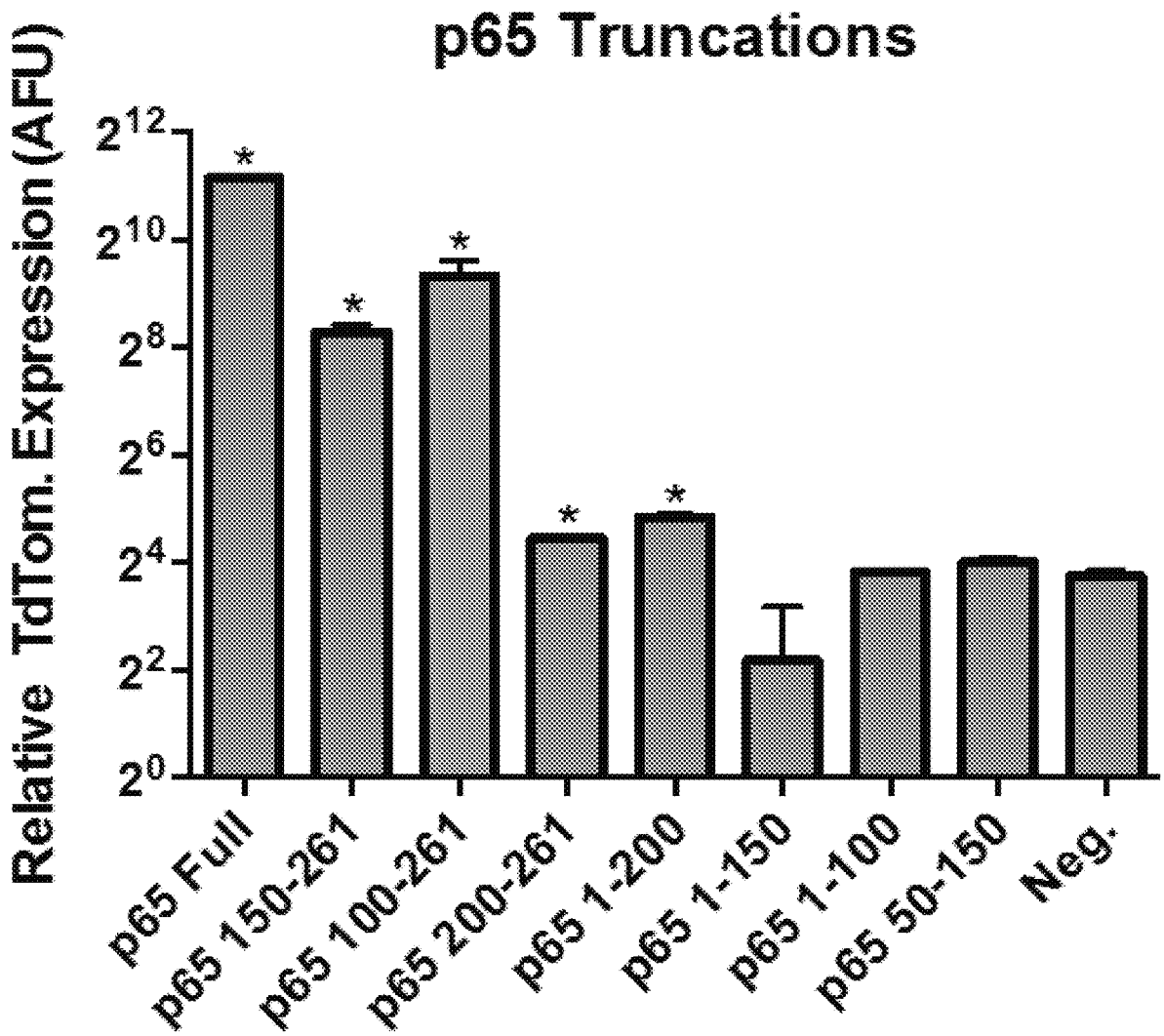
FIGS. 7A-7C depict the results of screen for truncated p65 and RTA domains that retain activity.
Figure 7B:
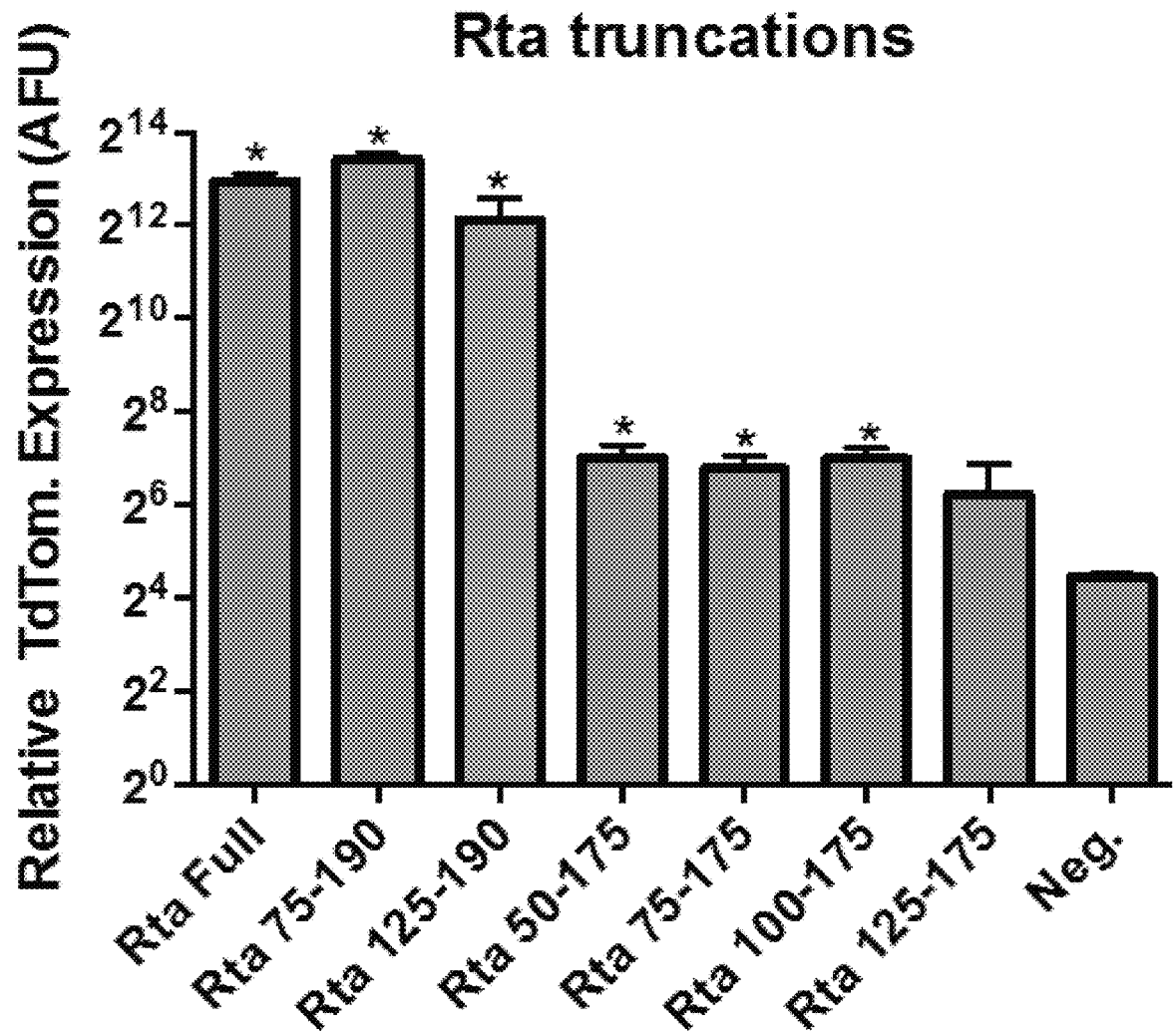
Figure 7C:
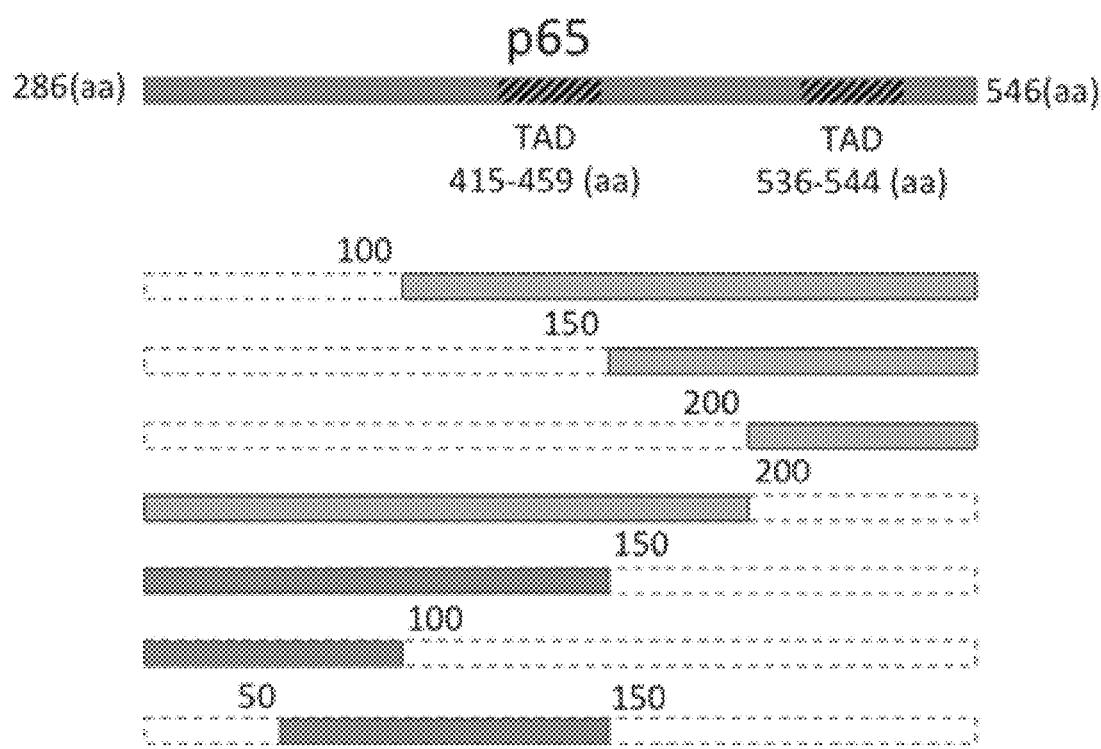
Figure 8A:
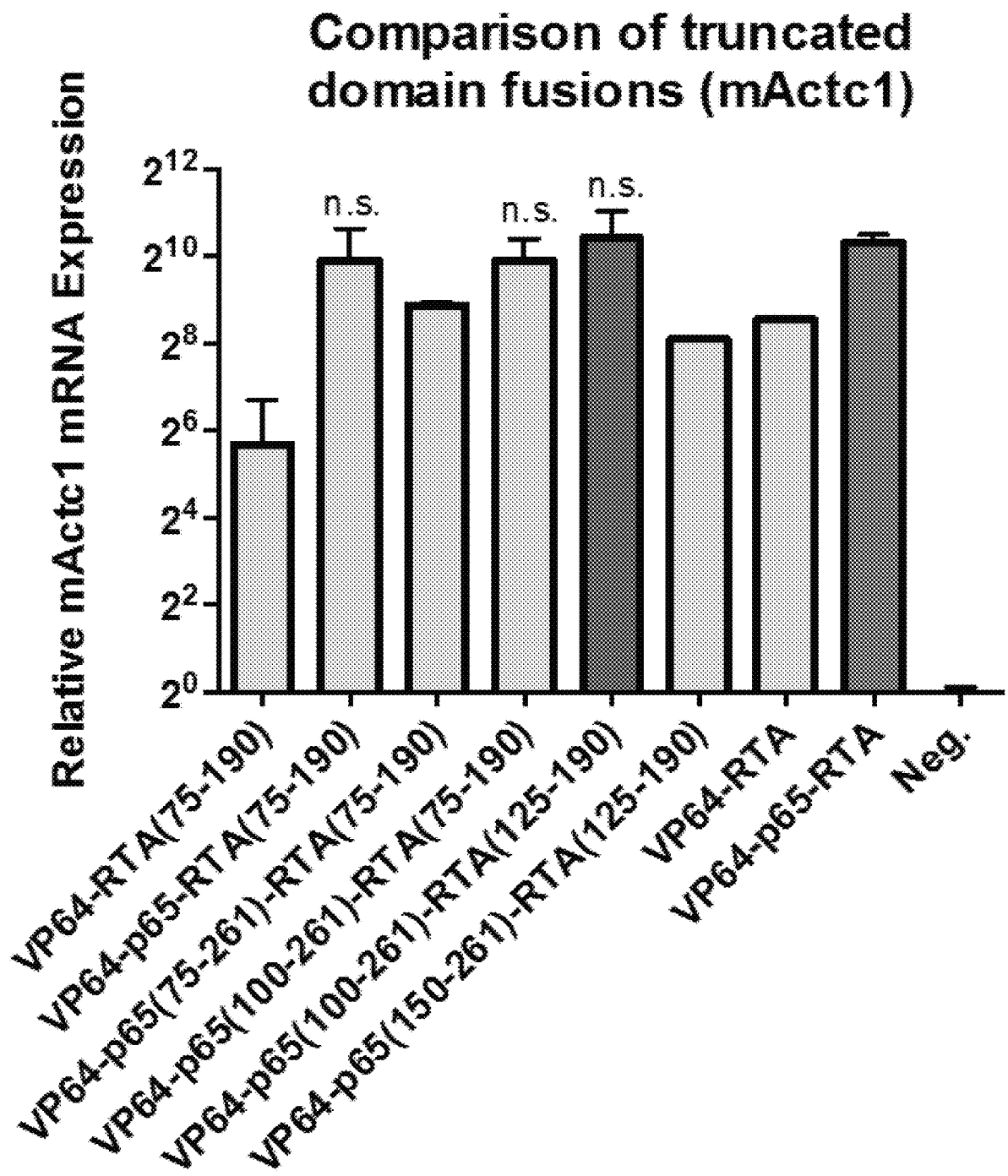
FIGS. 8A-8C depict results of a comparison of combinations of truncated activation domains fused to C terminus of nuclease null SpCas9.
Figure 8B:
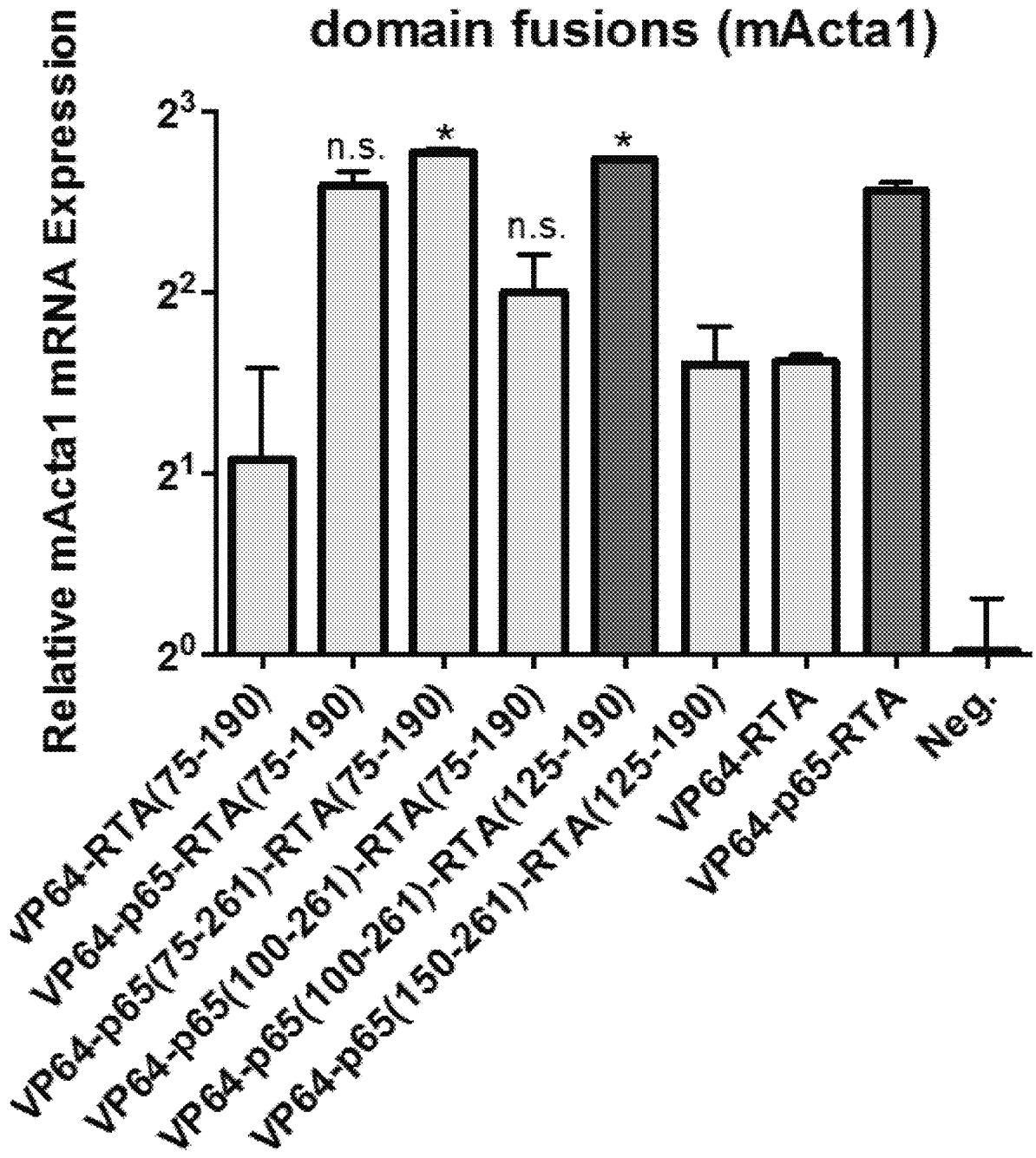
Figure 8C:
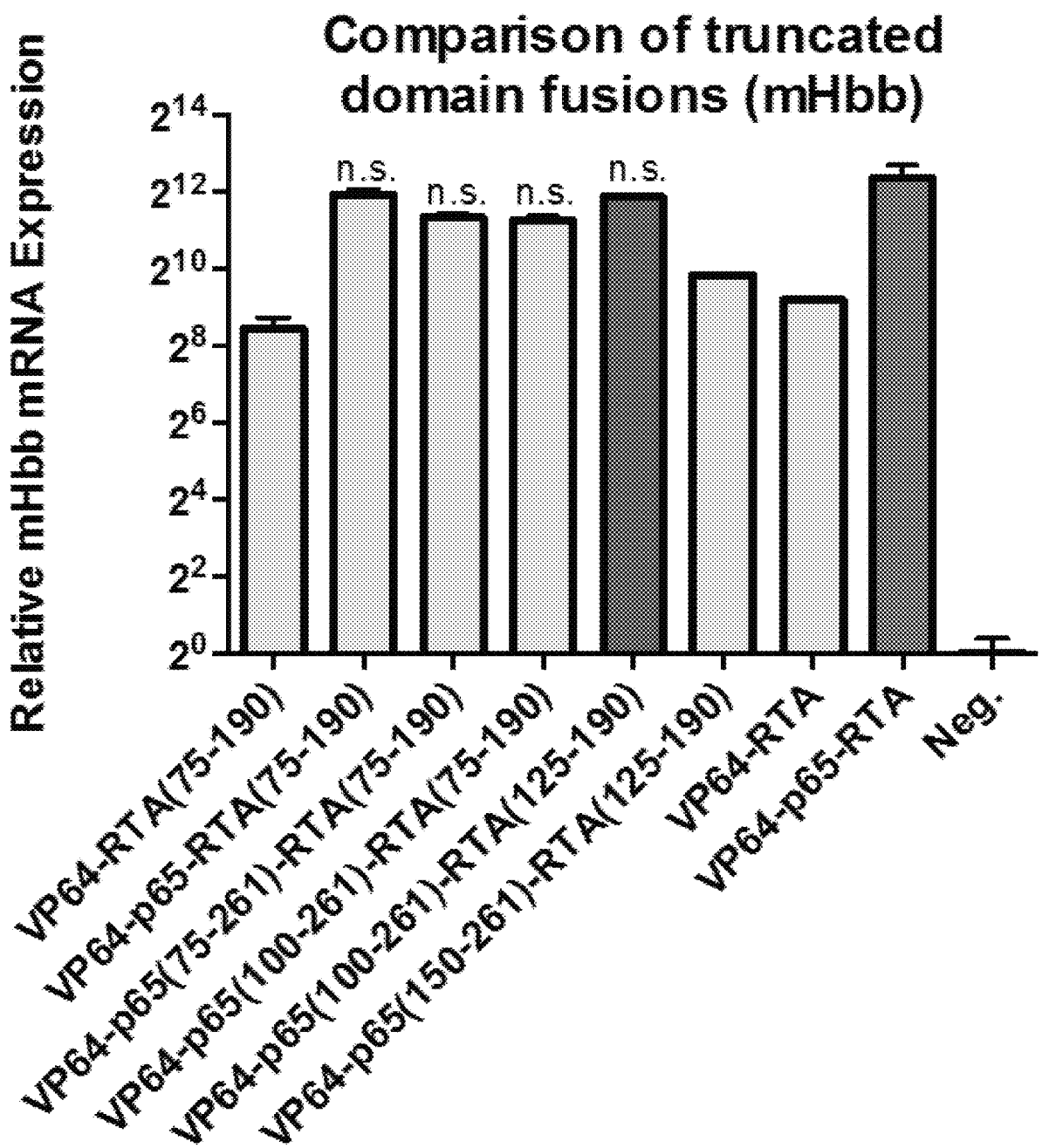
Figure 9B:
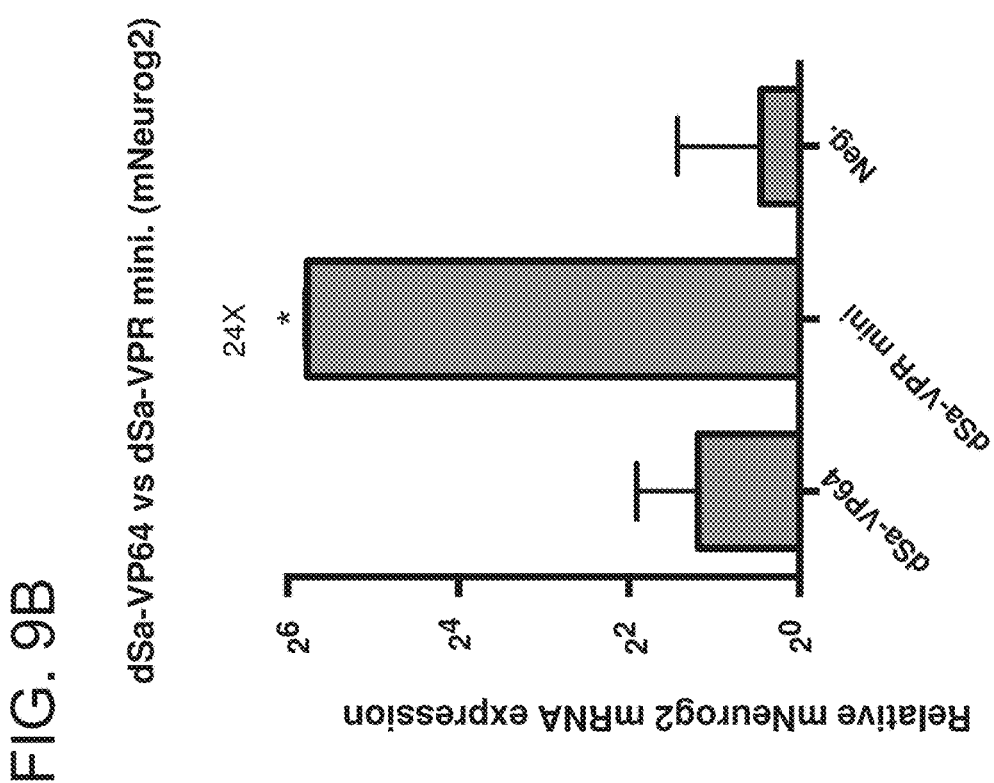
Figure 9A:
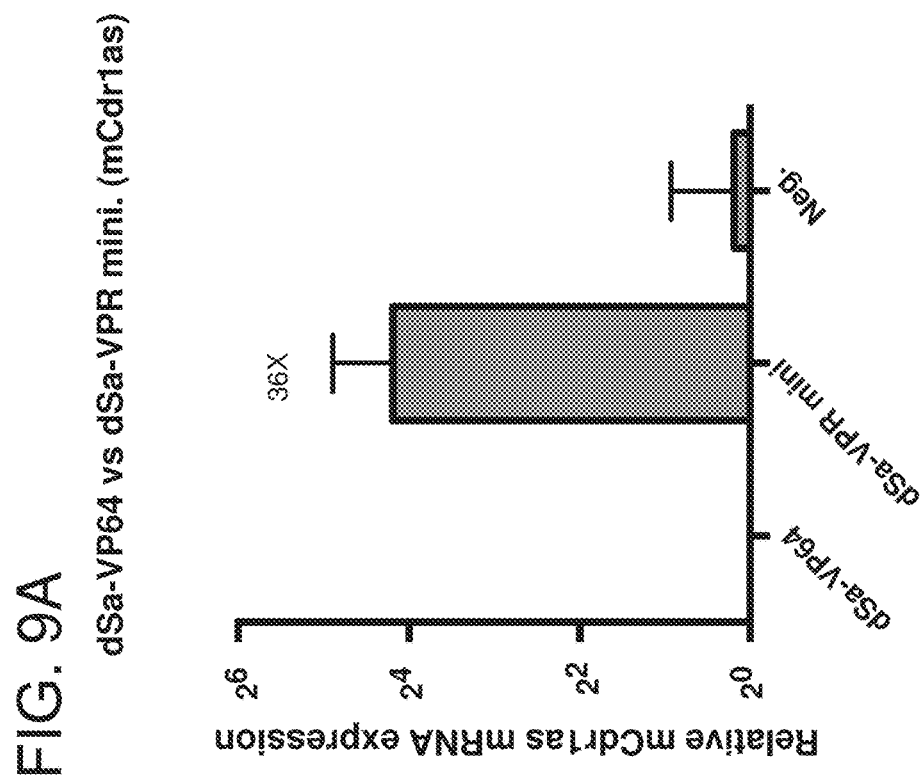
Figure 10B:
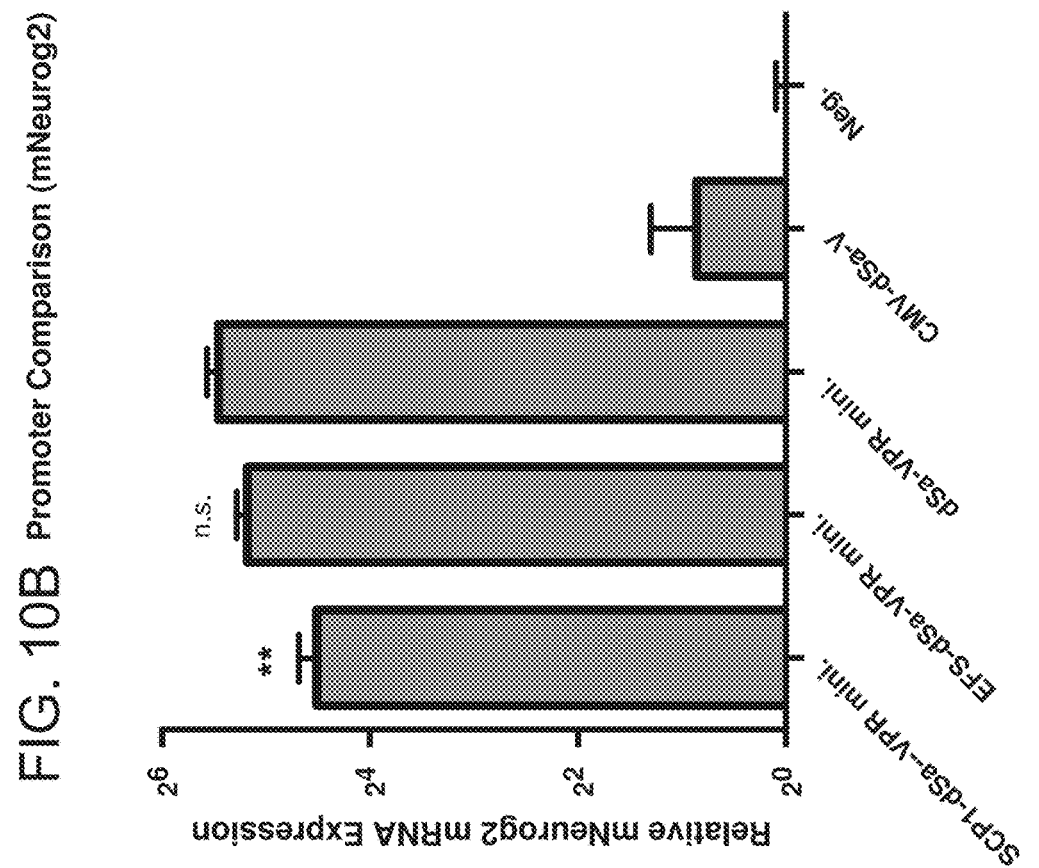
FIGS. 10A-10D depict results of comparison of novel SCP1 and EFS promoters.
Figure 10A:
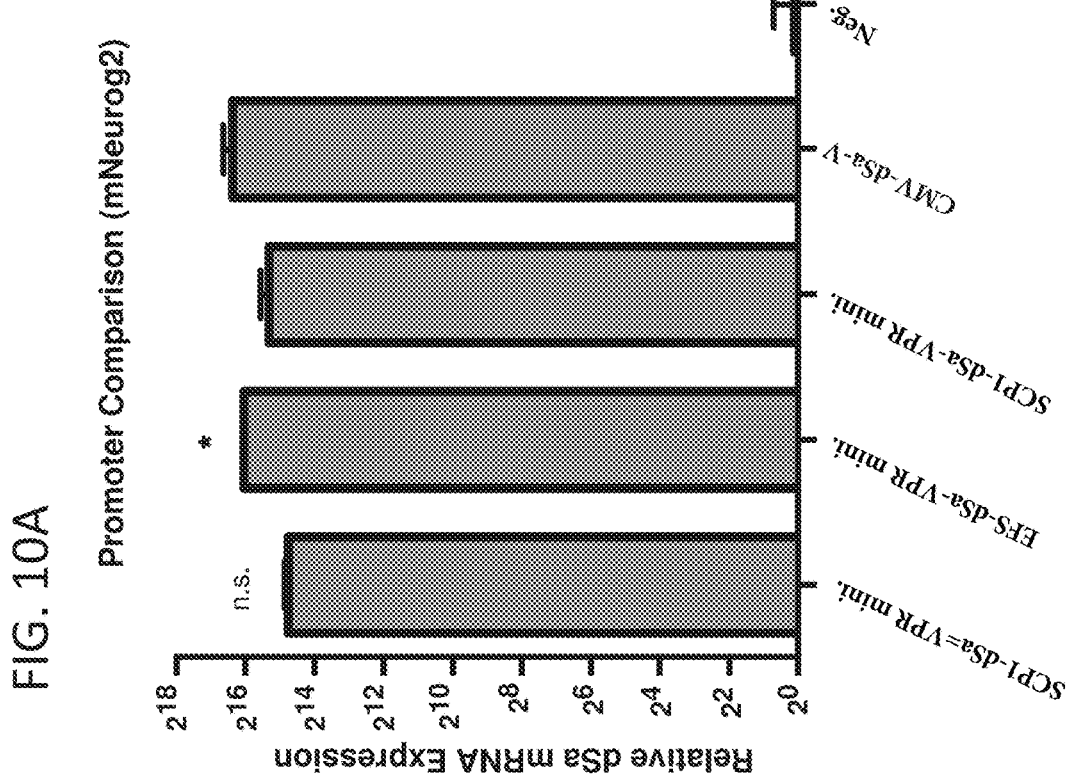
Figure 10C:
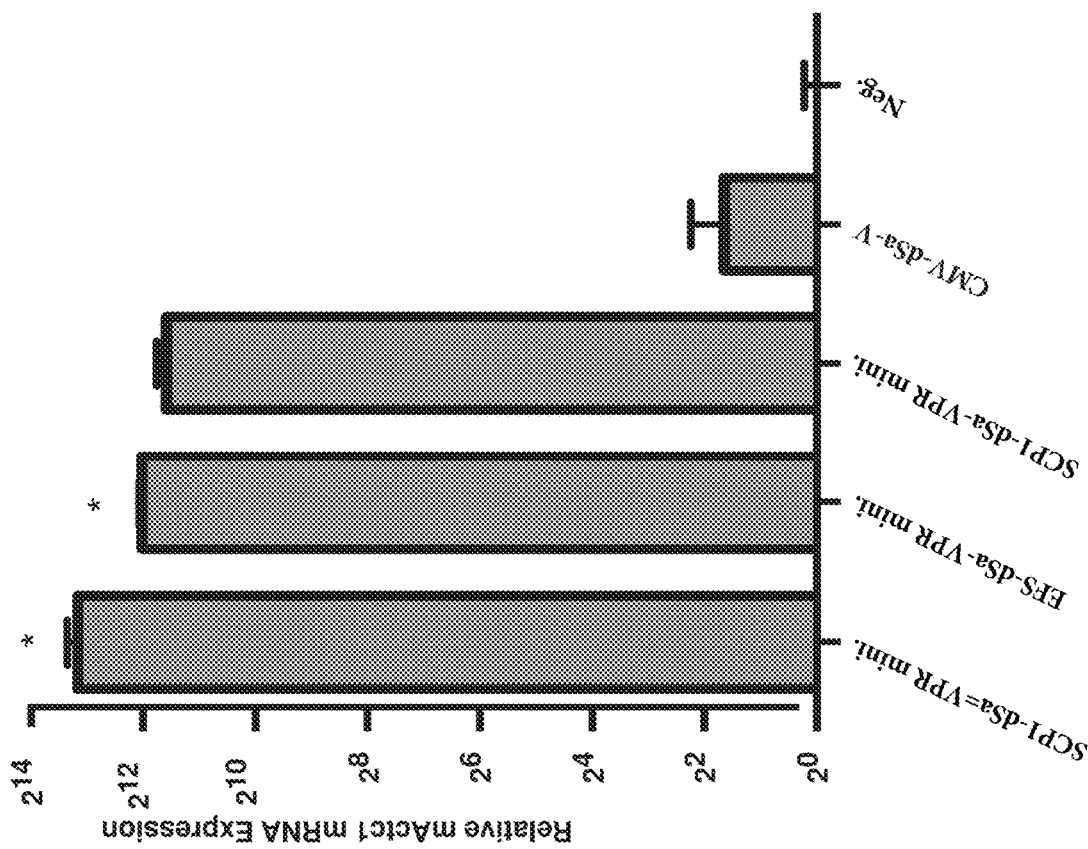
Figure 10D:
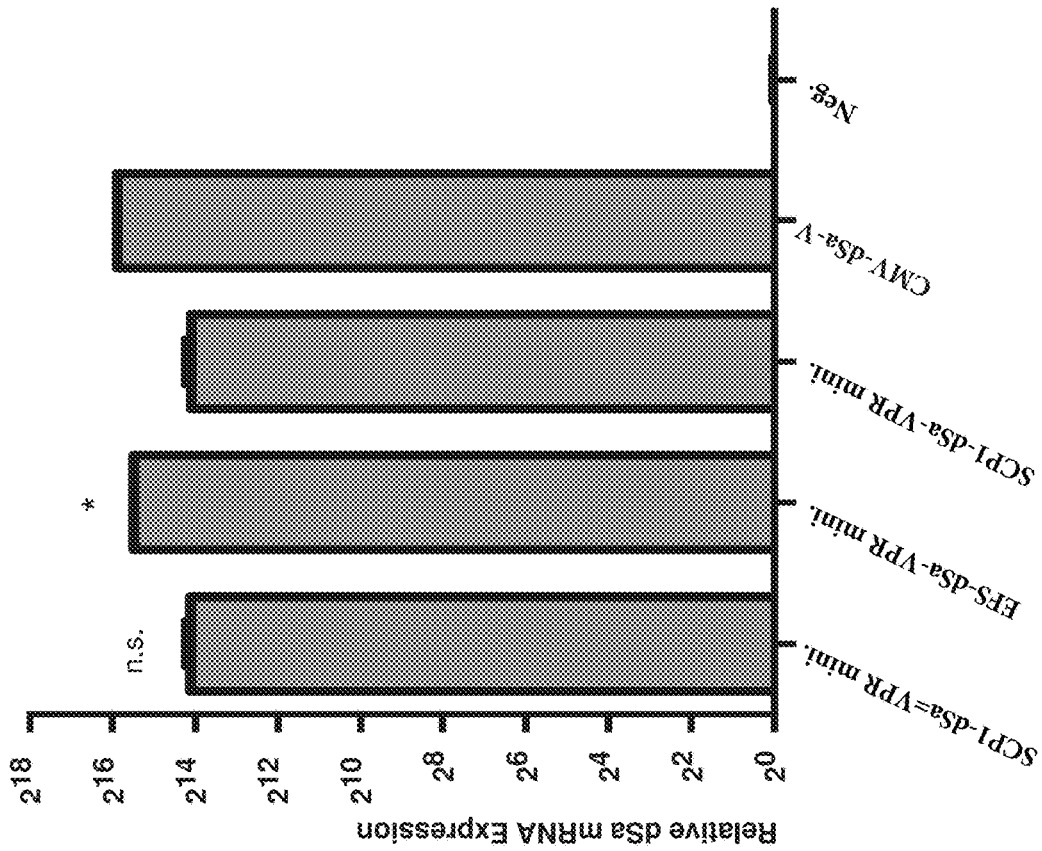
Figure 11A:
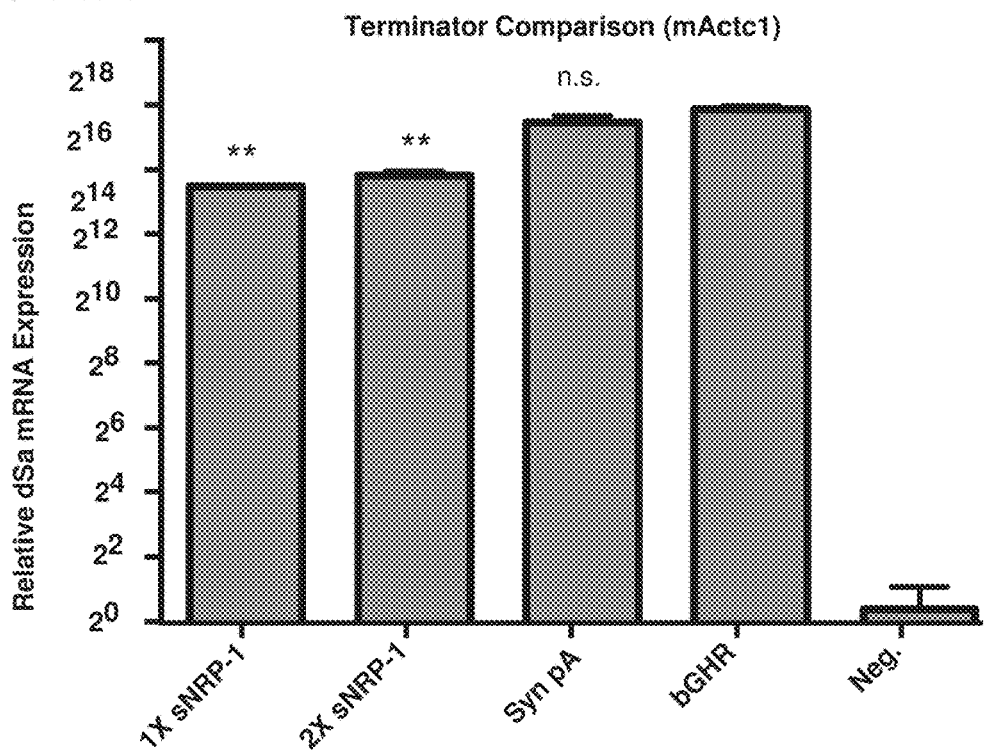
FIGS. 11A-11F depict results of comparison of extremely short poly adenylation sequences. Short 17nt sNRP-1, a 34nt dual sNRP-1, a 50nt synthetic, and a 250 nt bGHR terminators were cloned to the end of the dSa-VPR miniature expression cassette.
Figure 11B:
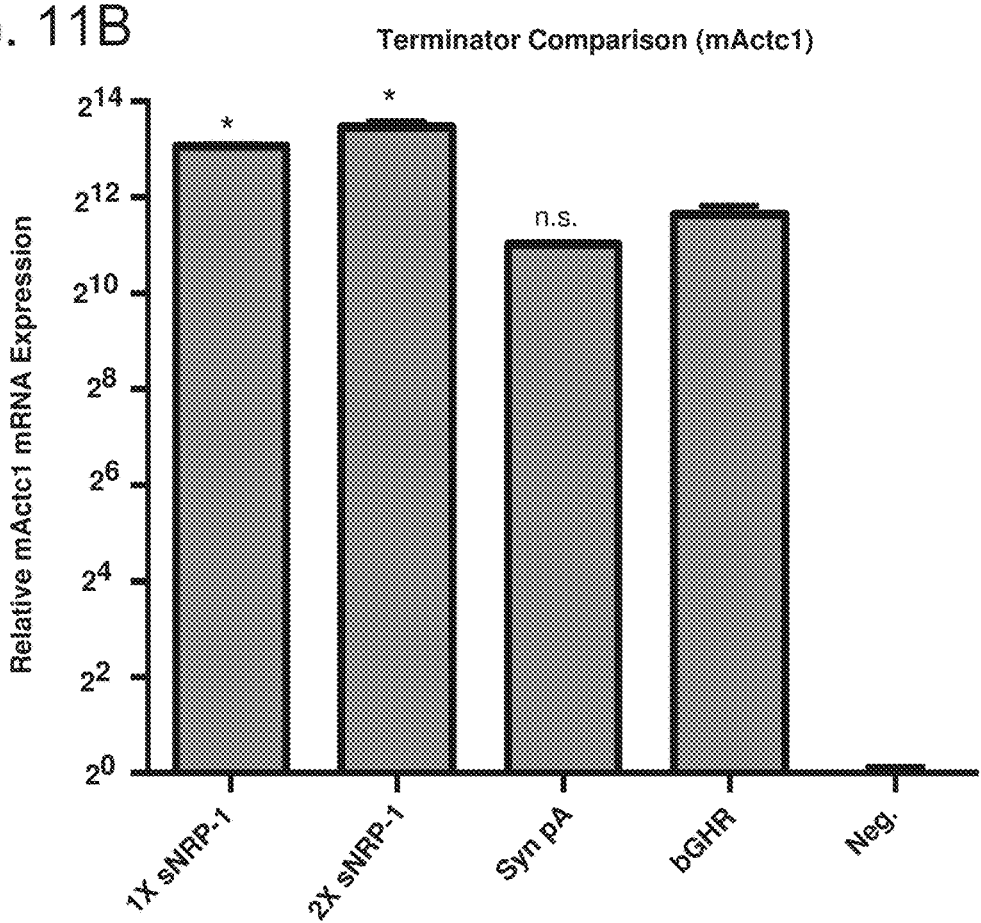
Figure 11C:
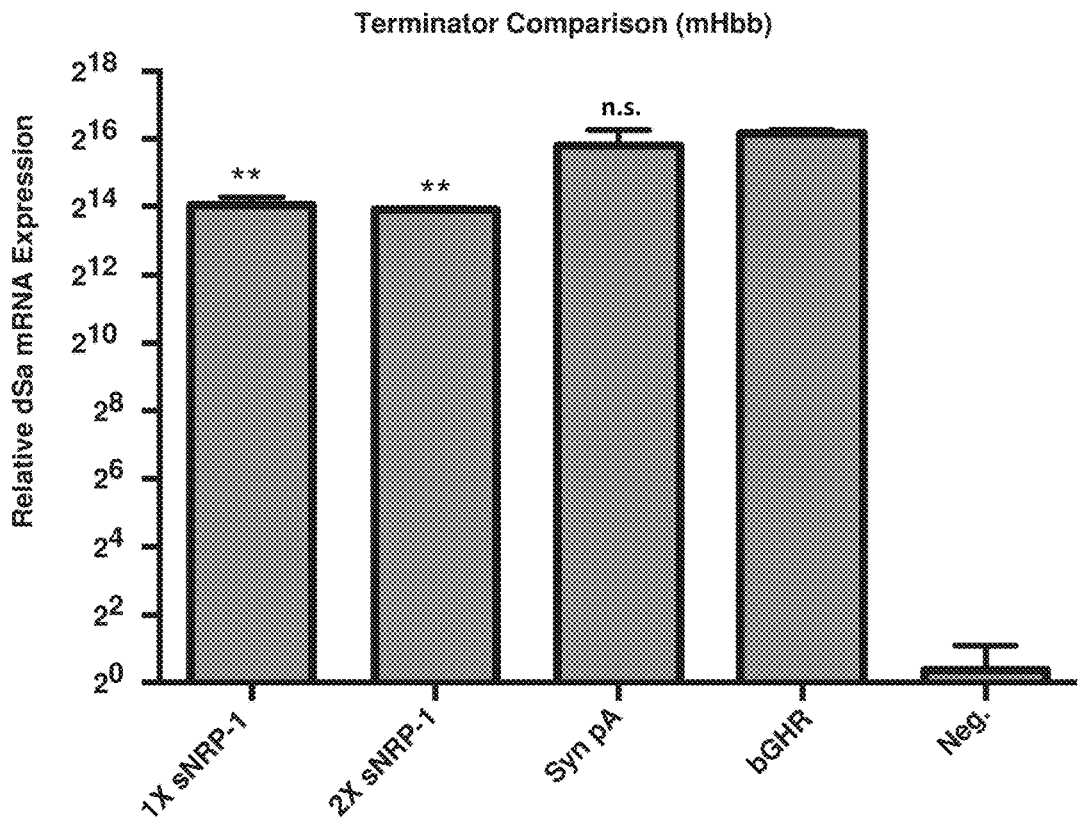
Figure 11D:
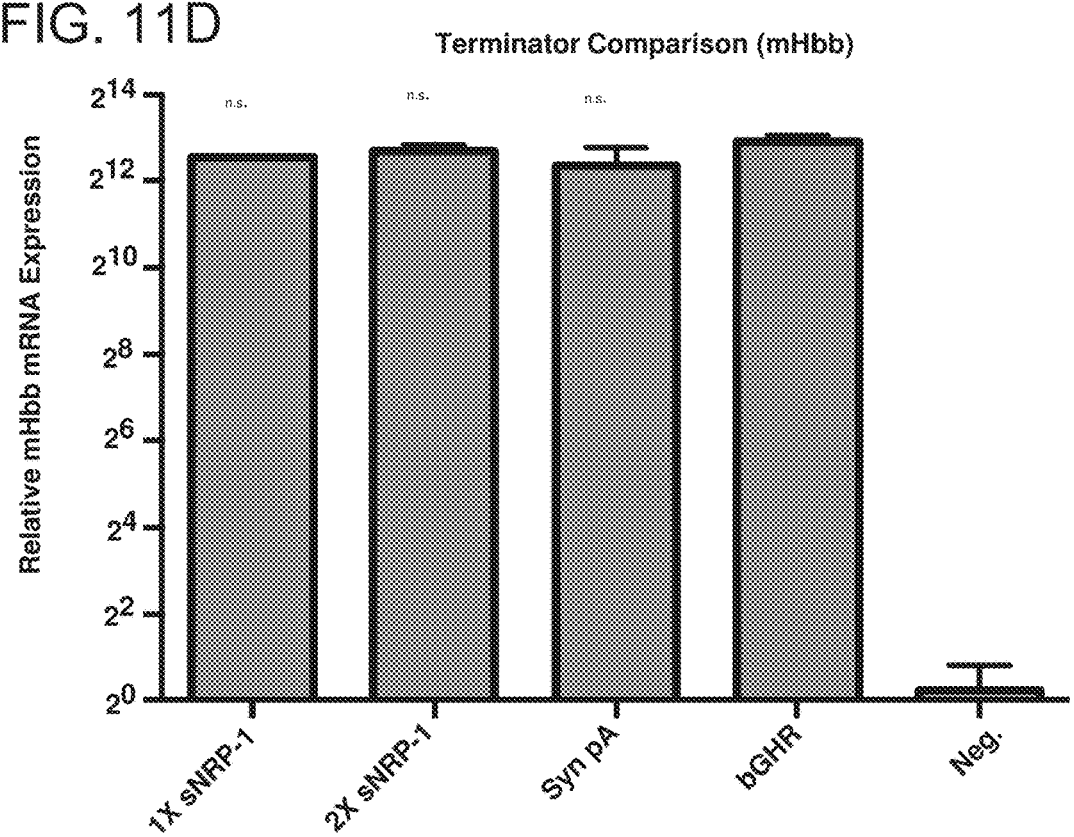
Figure 11E:
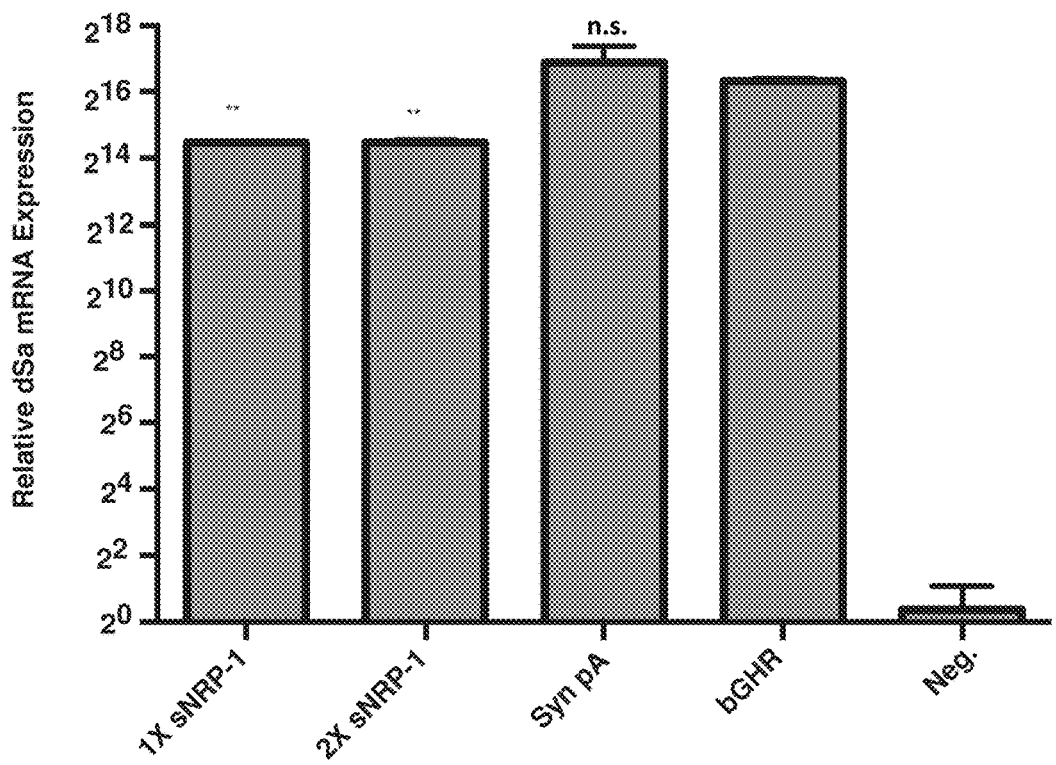
Figure 11F:
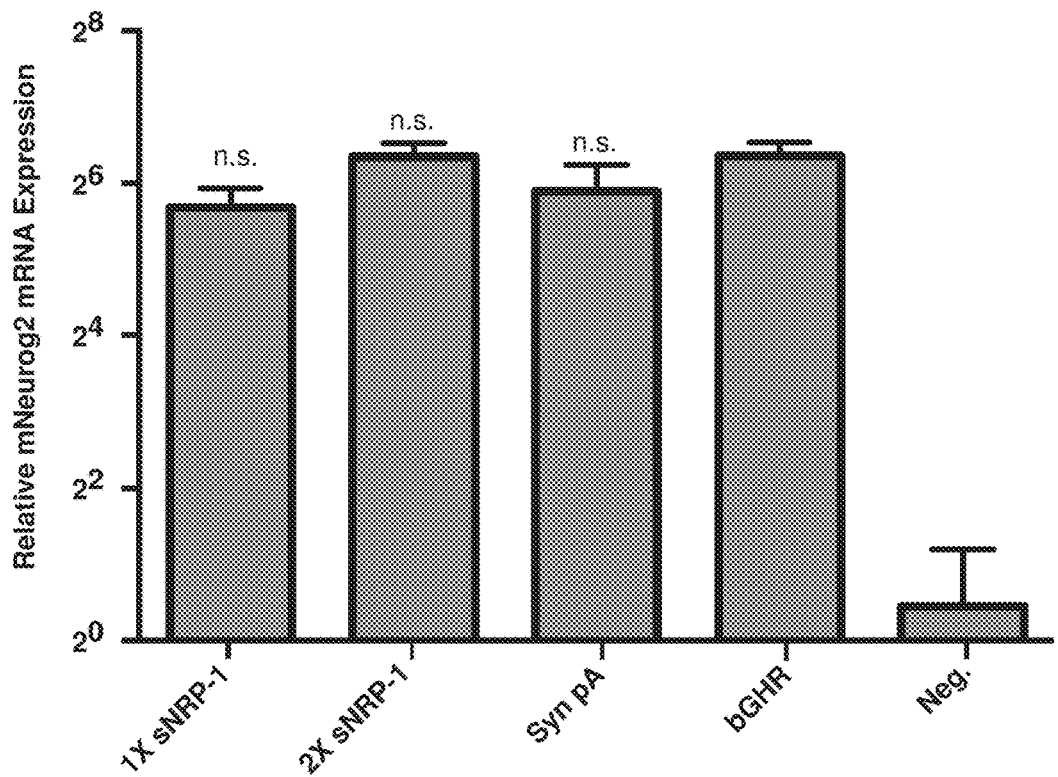
Figure 12A:
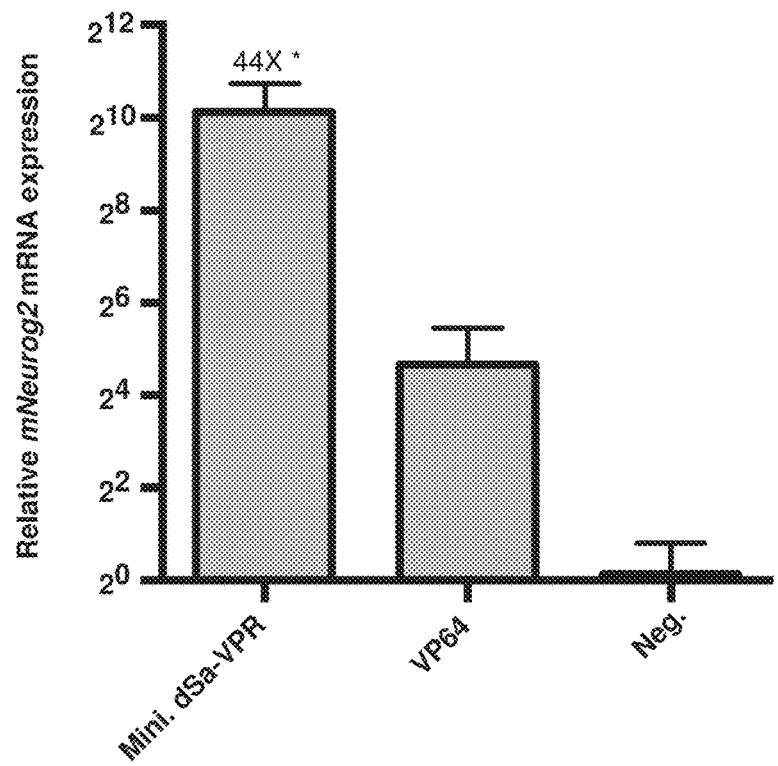
FIGS. 12A-12C depict results of comparison of single-vector activator designs.
Figure 12B:
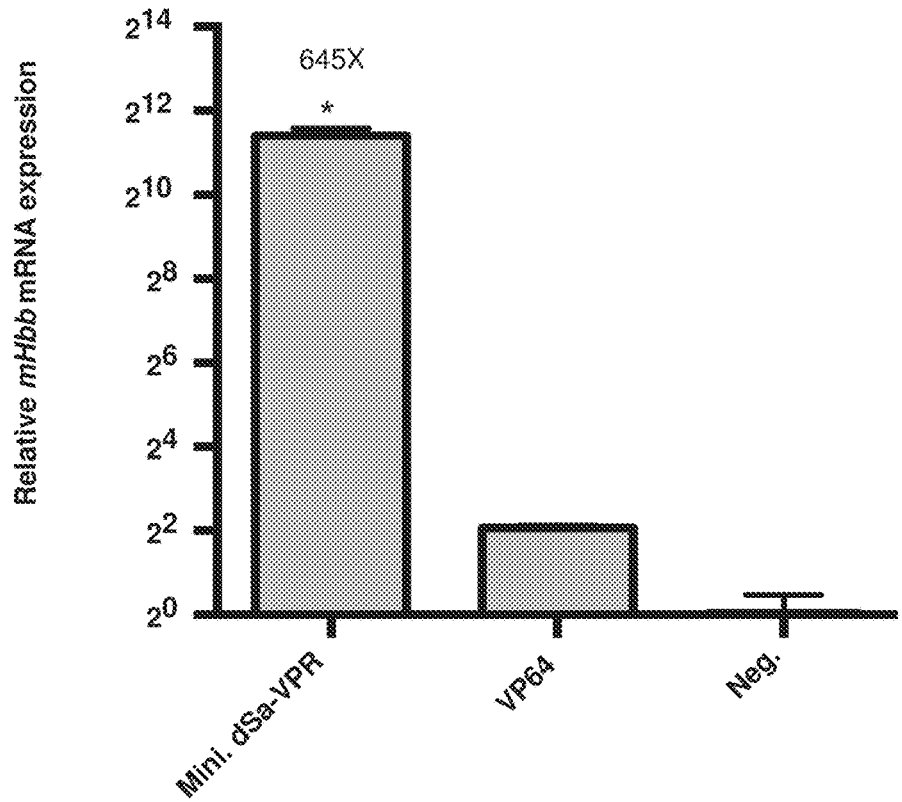
Figure 12C:
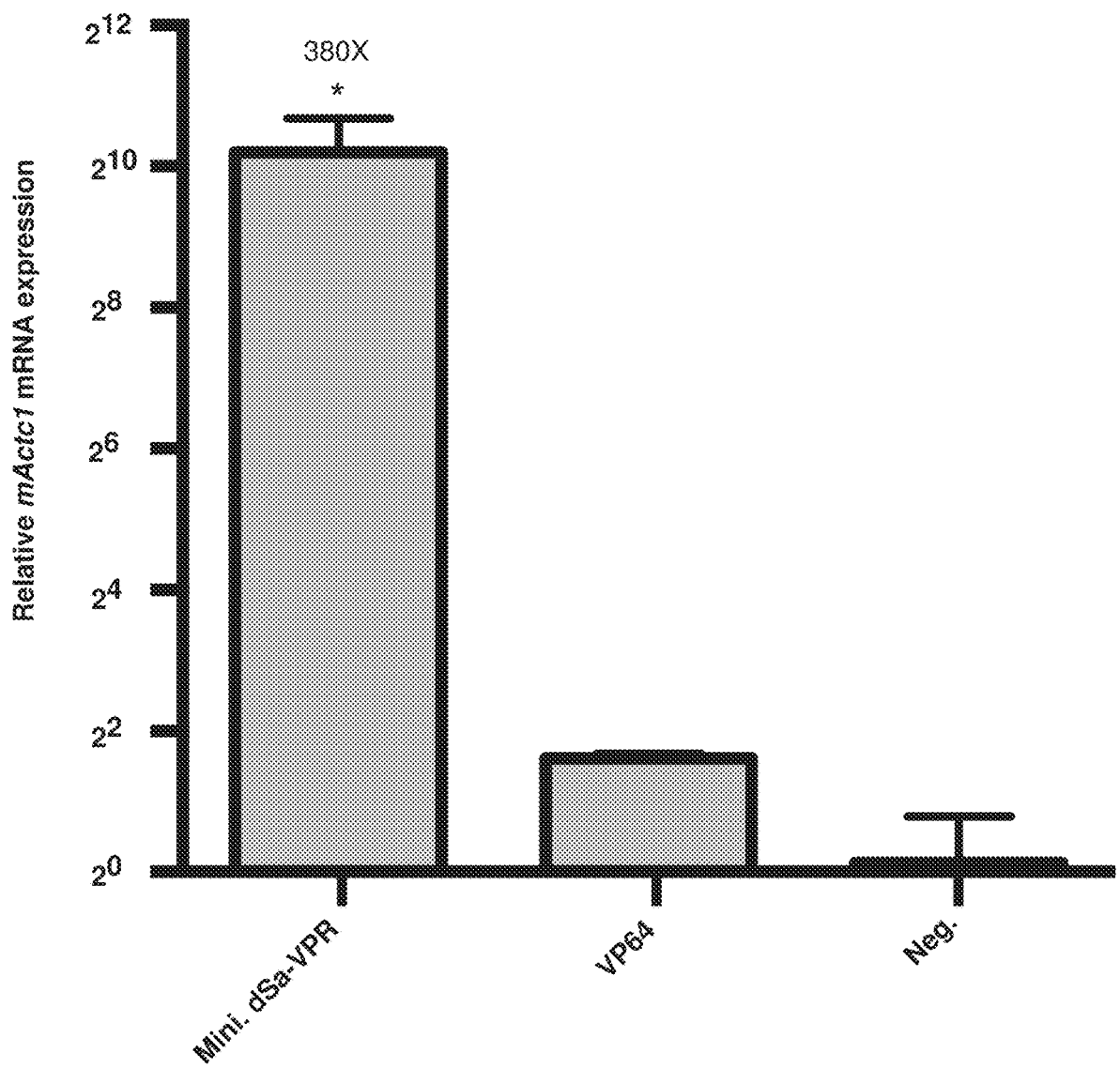
Figure 13A:
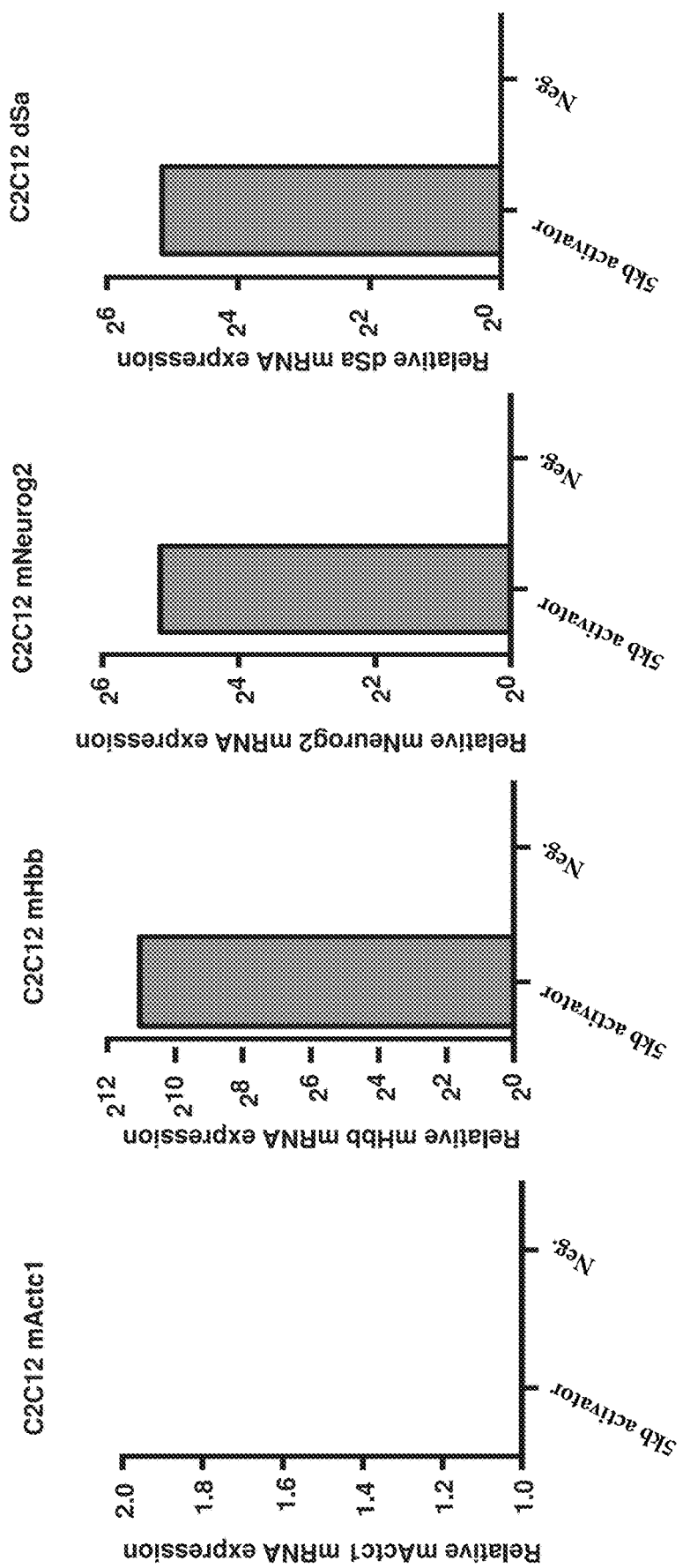
FIGS. 13A-13D depict results of validation of new activator tool in 4 cell lines.
Figure 13B:
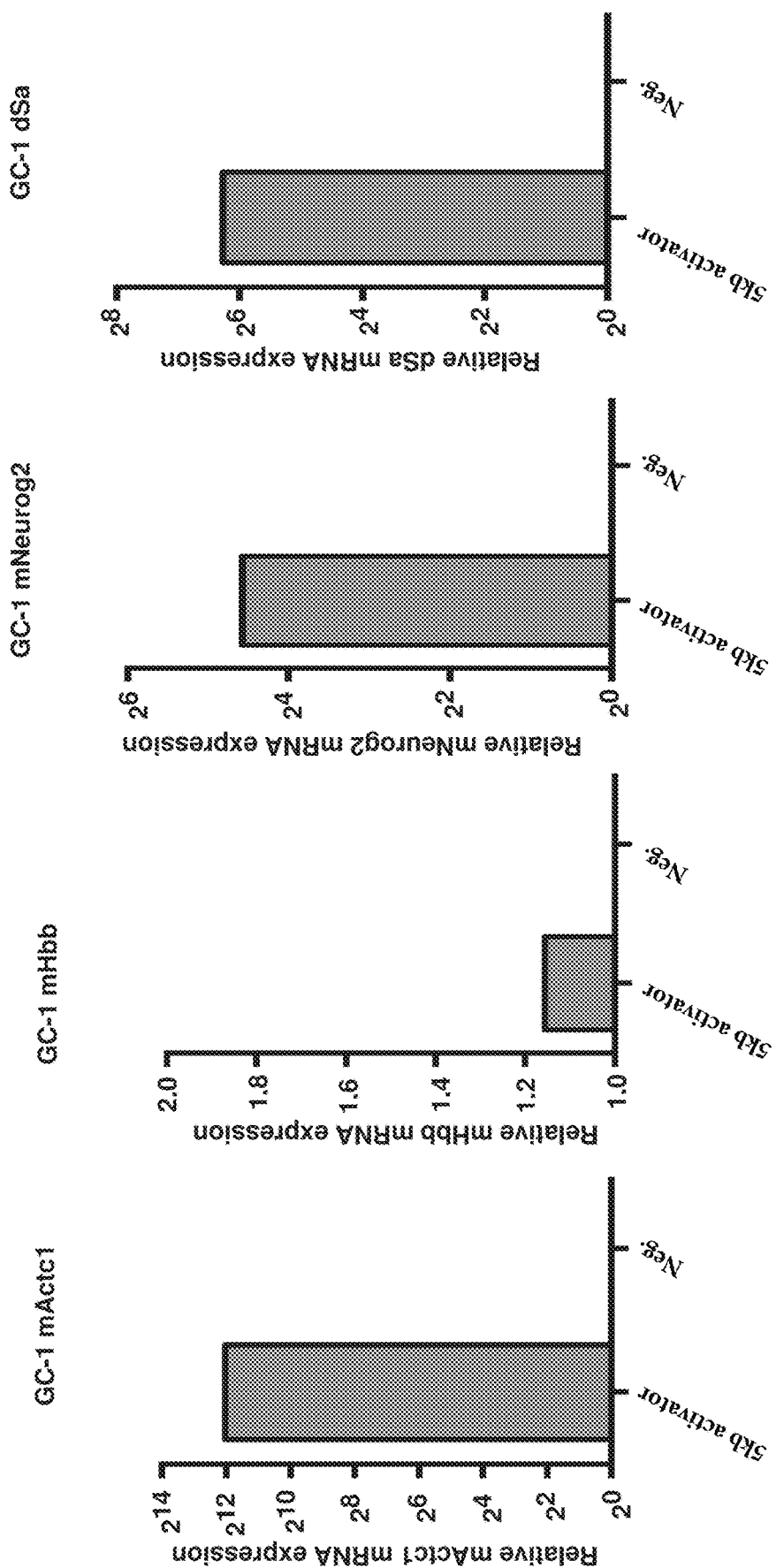
Figure 13C:
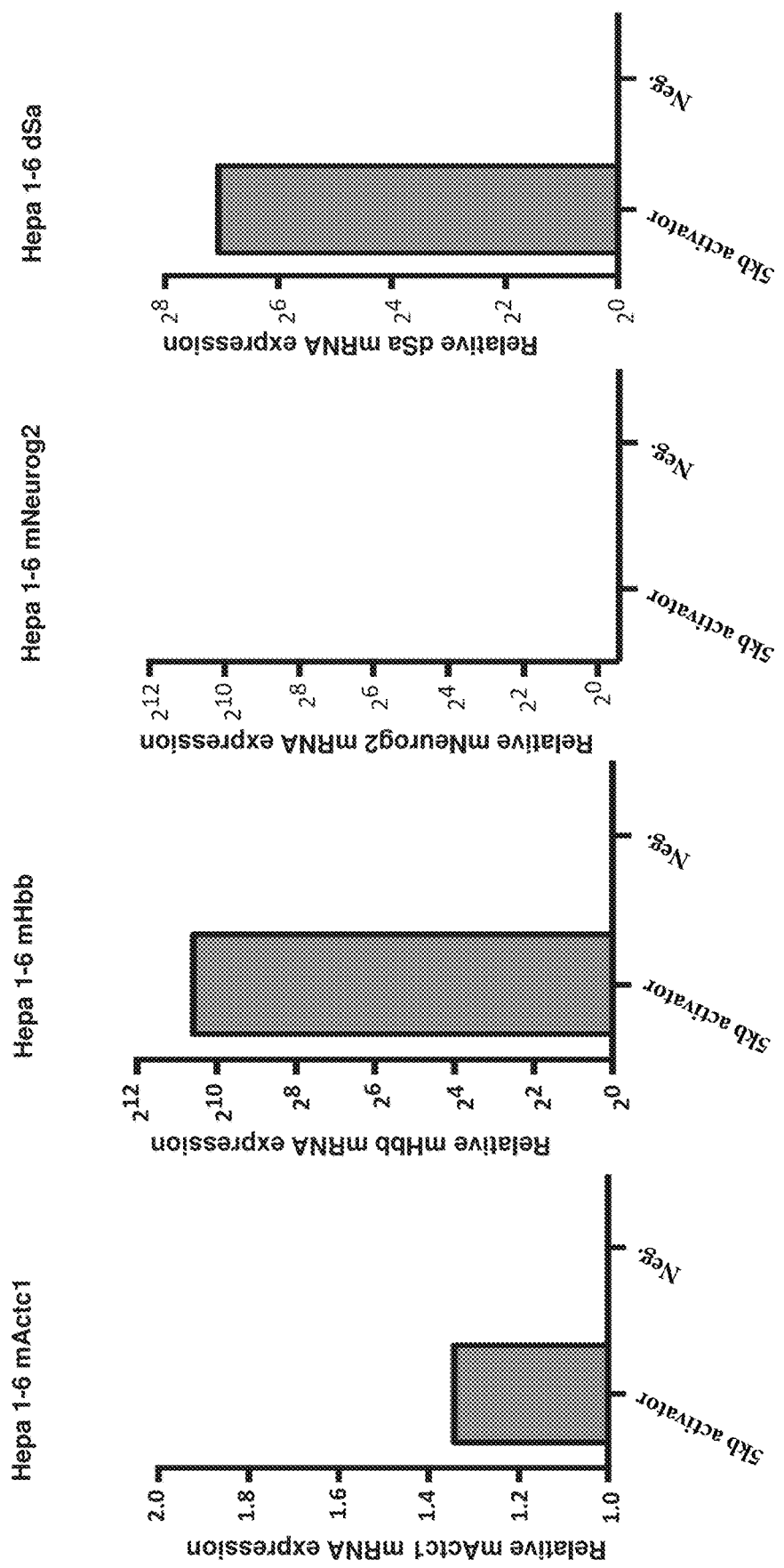
Figure 13D:
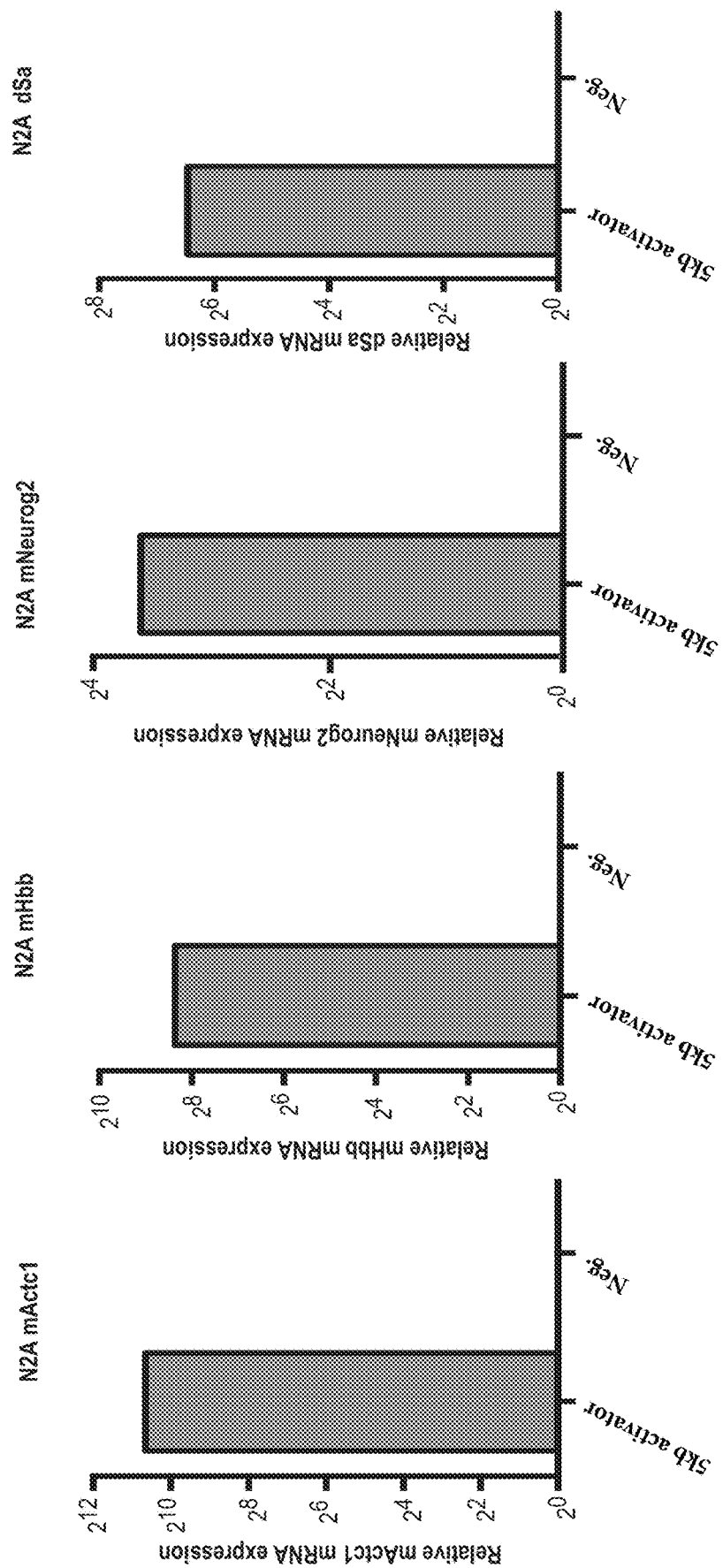

Beyond single gene activation, a primary advantage of the Cas9 system is the ability to target several loci in tandem. Cas9 enables multiplexed activation through the simple introduction of a collection of guide RNAs against a desired set of genes. To determine the efficiency of multi-gene targeting, a pooled activation experiment was performed simultaneously inducing four of our initially characterized genes MIAT, NEUROD1, ASCL1, and RHOXF2. VPR allowed for robust multi-locus activation, exhibiting severalfold higher expression levels than VP64 across the panel of genes. Despite the general performance decrease resulting from multiplex transcriptional modulation, our system still directed the induction of all targets to greater than 450-fold over their basal expression levels in the control cells (FIG. 4).

1.5 Activation on Multiple Programmable DNA-Binding Platforms

Given the activation efficiency of our SP-dCas9-VPR fusion, it was investigated whether the VPR construct would exhibit similar potency when fused to other DNA-binding scaffolds. Fusion of VPR to a nuclease-null *Streptococcus thermophilus* (ST1)-dCas9, a designer transcription activator like effector (TALE), or a zinc-finger protein allowed for a respective ~6x, ~4x, and ~2x increase in activation relative to VP64, as determined by a reporter assay[45,46]. (Data not shown.)

1.6 Cross-Organismal Activation

Given the activation efficiency of our SP-dCas9-VPR fusion in the human HEK 293T cell line, it was investigated whether the VPR construct would exhibit similar potency when targeted to genes in fly, yeast, and mouse cell lines. Targeting to *Drosophila melongaster* Schneider 2 (S2) cells allowed for 3300-fold up-regulation of the Cecal gene and 32,600-fold up-regulation of the Mtk gene, corresponding to a respective 300-fold and 120-fold improvement upon dCas9-VP64 activation of the same loci. Targeting to *Saccharomyces cervisae* enabled 96-fold up-regulation of Gal7 and 39-fold up-regulation of Hed1, corresponding to a respective 9-fold and 5-fold improvement upon dCas9-VP64 activation. Targeting to *Mus musculus* Neuro-2a cell (N2A) allowed for 1200-fold up-regulation above background expression level of Actc1, corresponding to a 67-fold improvement upon dCas9-VP64. Remarkably, the ultimate cardiac actin expression level induced by dCas9-VPR was 11-fold higher than mouse B-actin as measured by qPCR—an unprecedented result. (FIGS. 5A-5C).

1.7 iPSC Reprogramming to Neurons as Proof of Principle

The ability to regulate gene expression levels through transcriptional activation provides a powerful means to reprogram cellular identity for regenerative medicine and basic research purposes. Previous work has shown that the ectopic expression of several cDNAs enables cellular reprogramming of terminally differentiated cells to a pluripotent state, and can similarly induce differentiation of stem cells into multiple cell types[25]. While such studies typically require multiple factors, it was recently shown that exogenous expression of single transcription factors, Neurogenin2 (NGN2) or Neurogenic differentiation factor 1 (NEUROD1), is sufficient to induce differentiation of human iPS cells into induced neurons (iNeurons)[47]. It was previously attempted to recapitulate this same differentiation paradigm using dCas9-VP64 based activators and observed minimal differentiation activity (data not shown). It was hypothesized this was due to insufficient activation and therefore postulated that VPR might overcome this barrier and enable differentiation of iPS cells to iNeurons by more potently activating either NGN2 or NEUROD1.

Stable PGP1 iPS doxycycline-inducible dCas9-VP64 and dCas9-VPR cell lines were generated and transduced with lentiviral vectors containing a mixed pool of 30 gRNAs directed against either NGN2 or NEUROD1. To determine differentiation efficiency, gRNA containing dCas9-AD iPS cell lines were cultured in the presence of doxycycline for four days and monitored for phenotypic changes. It was observed that VPR, in contrast to VP64, enabled rapid and robust differentiation of iPS cells into a neuronal phenotype consistent with previously published reports. Additionally, these cells stained positively for the neuronal markers Beta III tubulin and neurofilament 200[48]. Quantification of Beta III tubulin staining revealed that dCas9-VPR cell lines showed either ~22.5× or ~10× improvement in the amount of iNeurons observed through activation of NGN2 or NEUROD1, respectively. Similar results were observed with neurofilament 200 staining. Analysis by qRT-PCR four days after doxycycline-induction revealed a ~10-fold and ~18-fold increase in mRNA expression levels for NGN2 and NEUROD1, respectively, within dCas9-VPR cells over their dCas9-VP64 counterparts (data not shown.)

Example II

Single Vector Delivery of Cas9 Activators In Vivo 2.1 Repurpose Tool with Small *Staphylococcus aureus* Cas9

While SpCas9 is most commonly employed for genome editing and transcriptional regulation applications, the St1 and Sa Cas9 orthologs are more suitable to in vivo applications due to their minimal size[46,49]. While the SpCas9 is 4.2 kb, barely able to fit in an AAV vector, the St1 ortholog is 3.4 kb, and the SaCas9 is 3.2 kb—both of which are able to comfortably fit within the size limit of AAV.

2.2. Minimize Activator Domains to Create Novel Small Activator

Even with the 1 kb gain in sequence space from replacing dSpCas9 with dSaCas9, the entire dSaCas9-VPR tool stands at 4.9 kb to express the activator gene alone. With the packaging limit of AAV being 4.7 kb, this tool is impossible to package, let alone with the necessary constitutive promoter (the standard is a 600 bp CMV promoter), poly adenylation signal (the signal used to express SaCas9 for in vivo editing is the bGHR signal of 250 bp), and sgRNA expression cassette consisting of the 250 bp RNA pol II U6 promoter and 100 bp sgRNA sequence. As such, all elements required minimization. It was hypothesized that the activation domains (p65 and RTA, originally identified to build the VPR activator) could be truncated to isolate only necessary elements for activator domain function. Sliding window truncations were performed on p65 and RTA to identify several minimal domains that retained activity. Furthermore, it was hypothesized that the truncated domains might retain their ability to induce high levels of gene expression, comparable to the full length VPR activator, when fused together as a synergistic unit.

2.3 Validate Mini Activator Against Mini Activator Control

The size of the Cas9 activator was able to be reduced from the original dSpCas9-VPR tool, standing at 5.9 kb, down to a miniature yet potent dSaCas9-VPR employing the p65 (100-261aa) truncation and the RTA (125-190aa) truncation, leading to a small yet effective tool of 4.2 kb—well below the packaging limit of AAV. While the dSa-VPR miniature activator is below the packaging limit of AAV, one other activator has been identified in the literature that is below the packaging limit of AAV, and that is the dSa-VP64 activator. To confirm the relative superiority of the dSa-VPR miniature activator over the dSa-VP64 tool, both tools were targeted to a set of 4 genes and compared relative levels of induction.

2.4 Identify Constitutive Small Promoters

While the activator tool is below the packaging limit of AAV, other elements must be incorporated into the final design. As such, several short promoters were screened, and identified two small constitutive promoters that would allow for high levels of dSa-VPR miniature expression, without compromising the tools ability to activate genes as compared to when expressed off of the gold-standard CMV promoter. The two promoters, SCP1 and EFS, are 80 and 200 bp long respectively, compared to CMV which is 600 bp in length.

2.5 Identify Effective Minimal Terminators

Similarly, several poly adenylation signals were screened, and identified an extremely short dual function polyadenlyation (pA) signal/stop codon that is efficient for termination of gene transcription and translation.[50,51] The short 17nt terminator was previously shown to work efficiently in vivo, and a dual repeat (34nt) version was shown to work comparatively efficiently to several other polyadenlyation signals including the popular SV40 polyA sequence. The single repeat sNRP-1 polyA signal, dual repeat version, the synthetic polyA signal, and the commonly used bGHR polyA signal were compared for ability to stabilize activator transcripts and therefore enable downstream activation of targeted genes.

2.6 Activate Endogenous Genes with Single Vector System

With a small 3.2 kb *Staphylococcus aureus* Cas9, a 1 kb miniature yet potent VPR activator, constitutive yet unprecedentedly small 80 bp SCP1 promoter, and a novel extremely short dual function transcription and translation 34 bp 2× sNRP1 terminator, a theoretical activator expression cassette totaling just above 4.3 kb was reached—well below the packaging limit of AAV. In order to create a single vector system, all elements were combined, alongside a 350 bp sgRNA expression cassette, to create a 4.7 kb tool ready for packaging in to AAV. The new single vector cassette for the ability of all elements to efficiently work together were validated by comparing the design to the only other activator that will currently fit within the packaging limit of AAV—the dSa-VP64 tool. Due to the smaller size of the dSa-VP64 tool, full-length CMV promoter and bGHR signals, along with the sgRNA expression cassette were able to be included, making the most of the space available when using the smaller activator. Then the two single vector tools were compared for ability to activate several target genes via transfection, to validate the enhanced potency of our novel single vector activator expression system, relative to the only other small activator available using gold standard expression elements.

2.7 Validate Single Vector Activator in Several Additional Mouse Cell Lines

The new tool performs far better than the alternative standard activator tool that would be available for packaging in to an AAV expression cassette. While many applications of in vivo transcriptional regulation will undoubtedly occur in neuronal cell types, it was wished to validate the efficacy of the SCP1 promoter, the novel miniature Cas9 activator, the compact sNRP-1 terminator, and guide RNA expression system in a variety of cell lines, to confirm the relevance of the tool for use in other tissue types. Thus, our novel activator was targeted to a panel of genes in 3 additional cell lines, C2C12 mouse myocytes, GC-1 mouse spermatogonial cells, and Hepa 1-6 mouse hepatocarcinoma cells, as well as Neuro-2A cells. Since the target genes will be present in a variety of epigenetic states when targeted in different cell types, and it is possible that genomic rearrangements in immortalized cell lines might even lead to a loss of the targeted locus in a new cell line, it was not expected that all targets to be activated in every cell line. However, at least one target was activated extremely well in each cell line, validating that each element is working in all four lines, albeit at different efficiencies depending on the locus.

2.8 Package Single Vector Activator in AAV

With the tool validated in 4 separate mouse cell lines in vitro, the new Cas9 activator expression system was packaged in to high titer AAV. AAV has 12 serotypes available for packaging, with a variety of tropisms specific to targeting a variety of tissue types including neuronal cells, muscle, liver, retinal cells, etc. However, an alternative serotype AAV-DJ has been developed, which allows for relatively efficient delivery to in vitro cell lines. In order to more rapidly validate that the tool packaged efficiently, could be delivered via AAV, and could mediate activation of target genes when packaged in AAV, it was chosen to initially package a tool targeting the mouse Actc1 gene in to AAV-DJ. To validate the packaging efficiency, the vector was titered by running qPCR on the packaged virus alongside qPCR of linearized vector standards, with defined copy numbers. Additionally, the AAV virus was denatured, and ran the packaged genomes on a 1% agarose e-gel with SYBR Gold stain, which visualizes single stranded DNA, alongside cut vector standards. a titer of roughly $10^{12}$ total viral particles isolated for the mActc1 targeting activator tool was detected, and it was observed a roughly 5 kb clean band on the electrophoresis gel, indicating that the vector has been correctly packaged.

2.9 Deliver Single Vector Activator via AAV to Activate Target Genes In Vitro

To validate the packaged Actc1 targeting activator tool, packaged in AAV-DJ, the virus was delivered to C2C12, Hepa 1-6, GC-1, and Neuro-2A cells, and assayed for expression of the targeted gene.

2.10 Deliver Single Vector Activator Via AAV to Activate Target Genes In Vivo

Figure 16A:
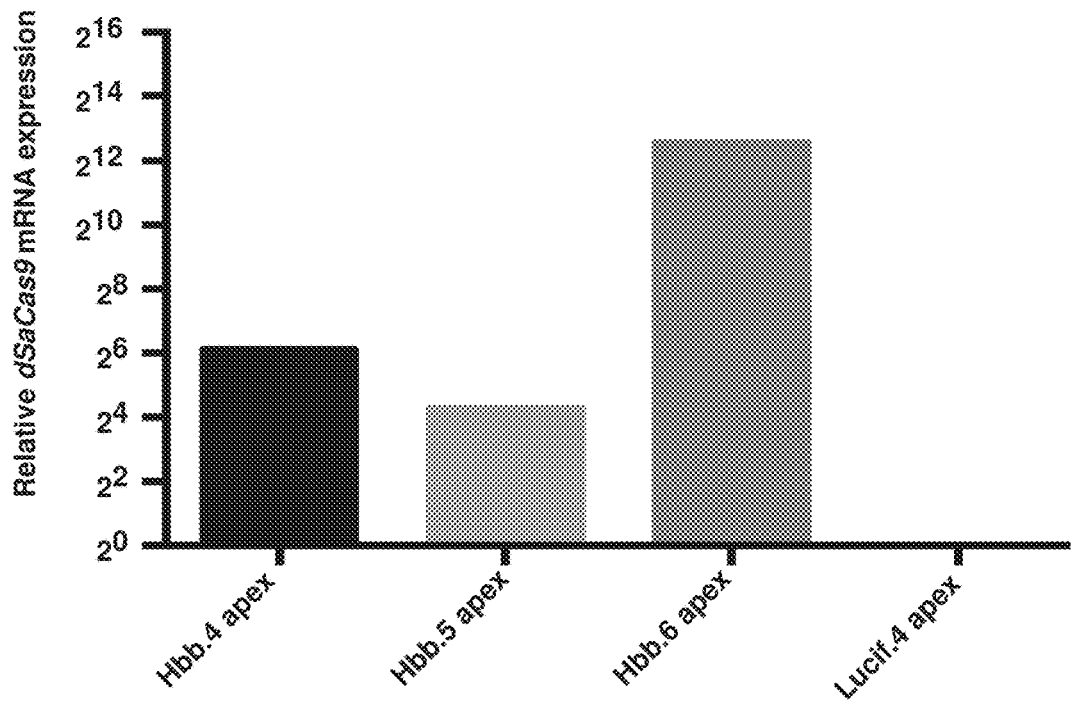
FIGS. 16A-16B depict results of target gene expression with AAV9 packaged tool. Roughly 1e10 viral particles were injected intraperitoneally in mouse pups on postnatal day 1. After 1 week, the pups were sacrificed; apex cardiac tissue was dissected for downstream analysis. Three pups were injected with AAV9 containing the mHbb targeting vector, and a control pup was injected with a negative control AAV9 prep. containing the gene for luciferase.
Figure 16B:
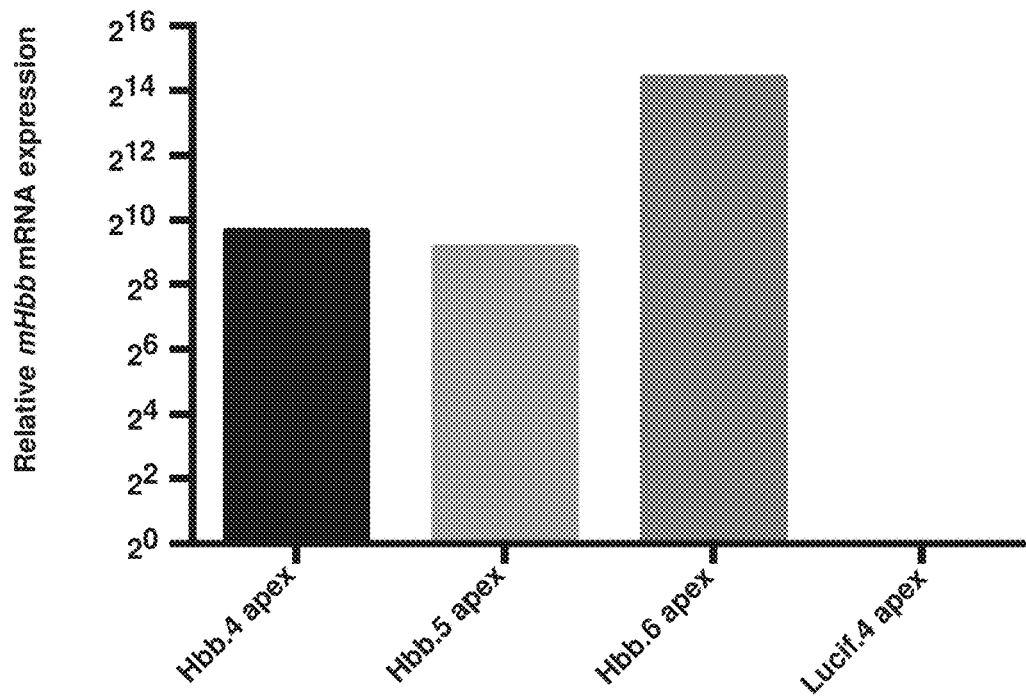

Following in vitro activation of target genes, it was aimed to validate the tool for activation of targeted genes in vivo. A batch of AAV-9 was produced, which targets cardiac tissue, with the mHbb targeting activator. The viral yield was $2 \times 10^{11}$, which is roughly 1 order of magnitude lower than typical viral prep. The pups were injected with the AAV preps, and collected heart, liver, and additional tissues a week post injection, to assay for Hbb expression. The results of this pilot experiment are shown in FIGS. 16A-16B below. All three targeting activation vectors will then be delivered (for Actc1, Neurog2, and Hbb) via systemic and potentially local injections of AAV-9, to assay for the efficacy of the tool for in vivo activation.

Example III

Activation of Therapeutic Genes In Vivo for Treatment of Monogenetic Muscle Wasting Diseases 3.1 Identify gRNAs for Activation of Targets with Single Vector Activator In Vitro Aspects of the present disclosure provides methods and systems that can be used for treating diseases such as monogenetic muscle wasting diseases. In exemplary embodiments, the present disclosure provides methods and systems for activating three target genes, Cardiac actin, Utrophin, and Brain Glycogen Phosphorylase for the treatment of monogenetic muscle wasting diseases in mouse models (Nemaline Myopathy, Duchenne Muscular Dystrophy, and McArdle's Disease, respectively.) Each of these diseases is caused by a mutation in a single gene coding for either a structural or enzymatic protein; the mutations lead to non-functional alleles and loss of muscle cell integrity. However, all three genes have alternative fetal isoforms, located in distal positions within the genome that are expressed throughout gestation. In to adulthood, the fetal isoforms are silenced, and the adult isoforms are induced—if the adult isoform contains debilitating mutations, the individual begins suffering from symptoms of the muscle wasting disease. However, there is good evidence that overexpression of the original fetal isoform may be a viable therapeutic avenue, as the fetal isoform is functionally equivalent to the adult isoform—and perfectly intact (as mutations in the fetal isoform would have been lethal during gestation.) In the case of Duchenne Muscular Dystrophy, it is not possible to deliver either a fully intact copy of either DMD cDNA (a corrected version of the diseased gene) or Utrophin cDNA (the alternative isoform of the disease gene) due to the sheer size of the two genes. Thus, attempts at activating endogenous Utrophin gene expression have begun—and a small molecule aimed at inducing Utrophin in adults suffering from Duchenne Muscular Dystrophy are currently in progress. However, the levels of gene activation are suboptimal. The methods and the miniature CRISPR Cas9 activator AAV system can be developed to target each of these three genes, as a proof of principle for application in transcriptional activation based gene therapy.

A single potent gRNA for targeting of Actc1 (Cardiac Actin) was identified. Further, appropriate gRNAs for Utrn (Utrophin), or Pygb (Brain glycogen phosphorylase) will be identified. Data for Actc1 using the isolated gRNA is shown in FIGS. 8A, 9C, 10D, 11B, 12C, 13, and 15A (all experiments targeting mouse Actc1.)

3.2 Package Single Vector Tools in AAV

Figure 14A:
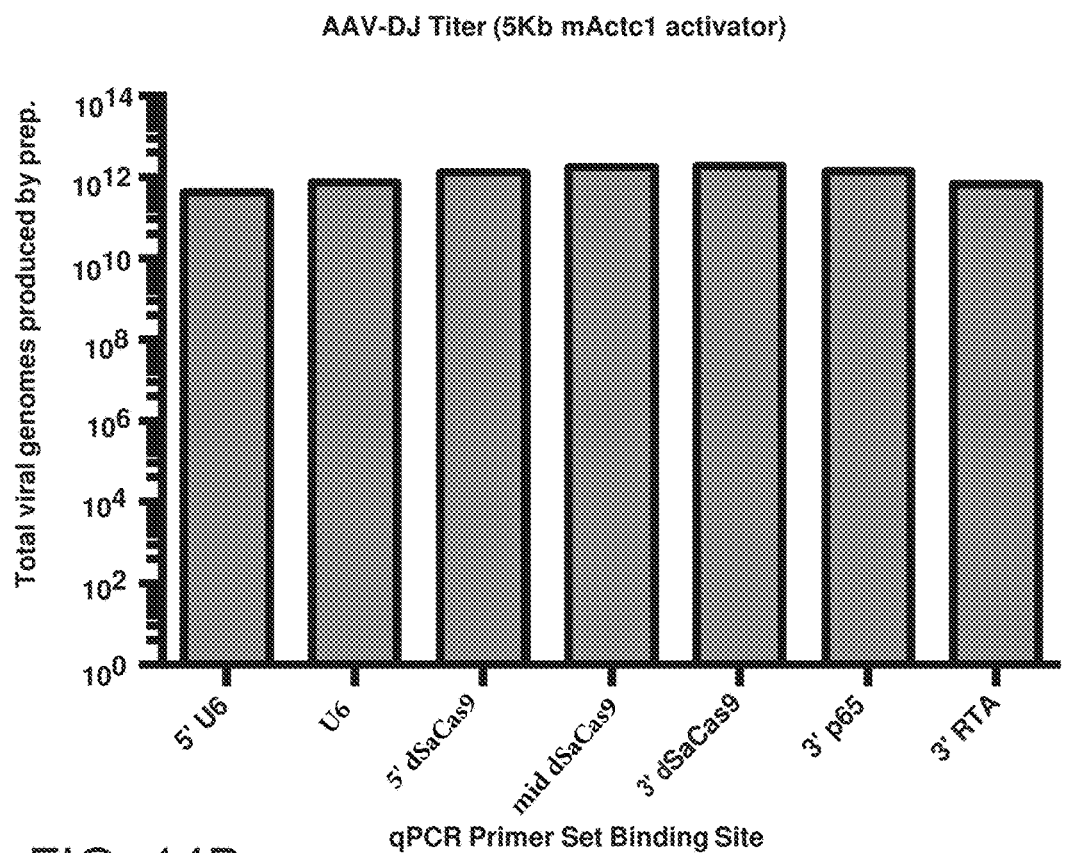
FIGS. 14A-14B depict results of validation of mActc1 targeting tool AAV-DJ packaging.
Figure 14B:
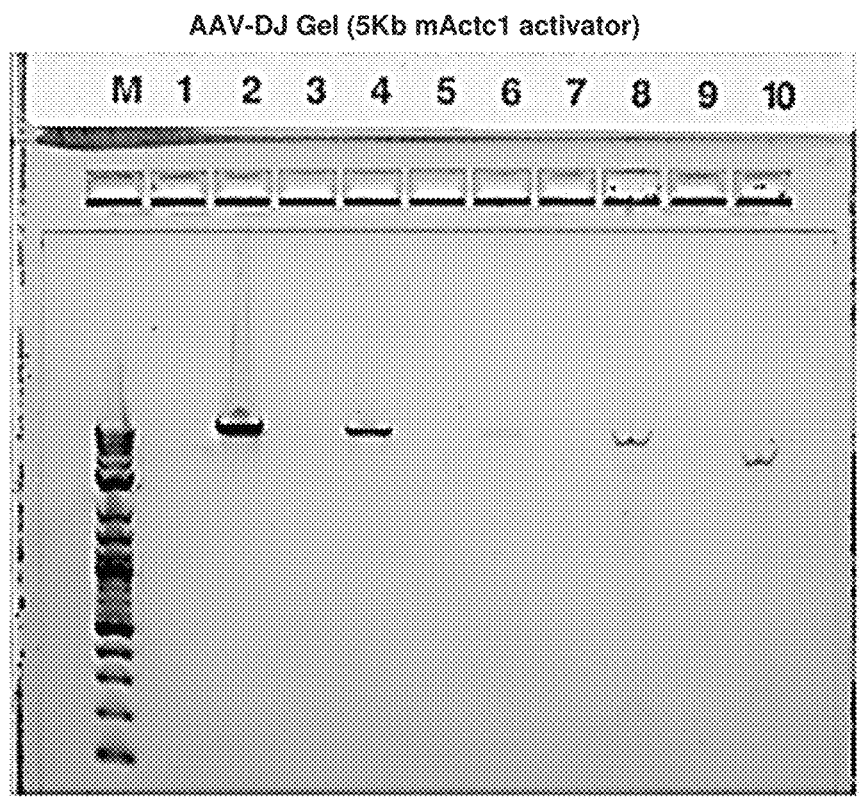
Figure 15:
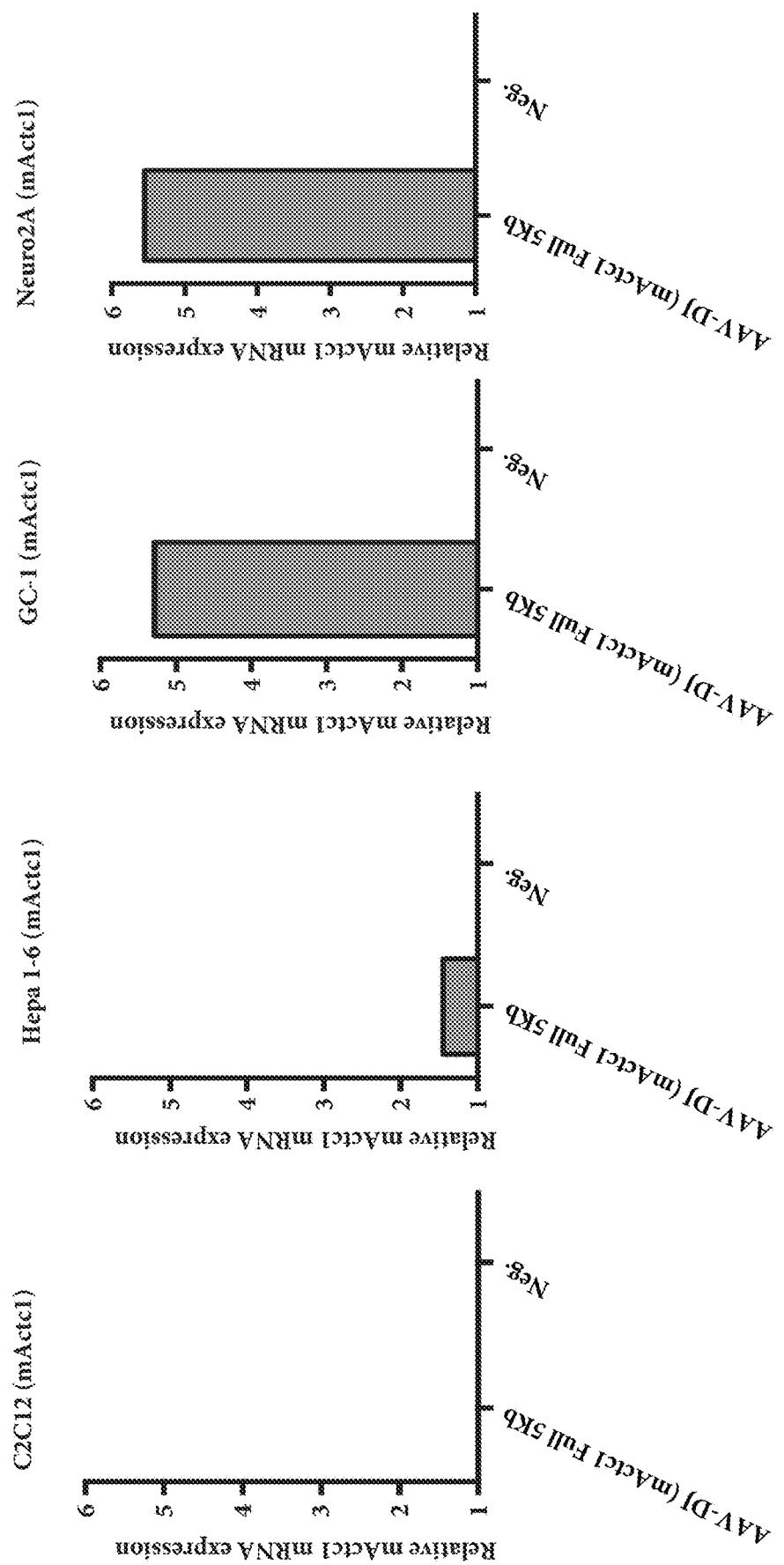
FIGS. 15A-15D depict results of delivery of AAV-DJ with Actc1 activator tool to 4 cell lines in vitro.
Figure 15B:
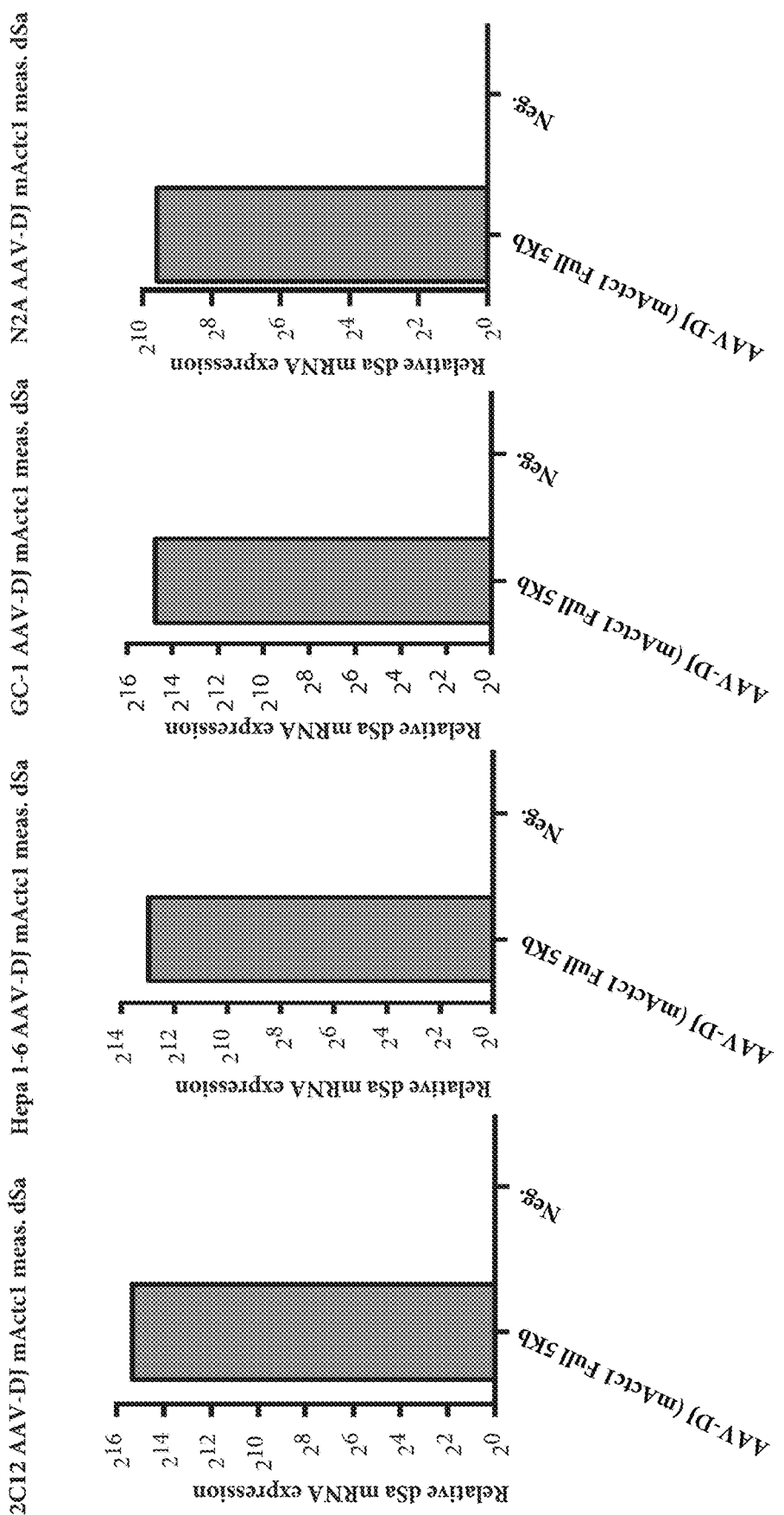
Figure 15C:
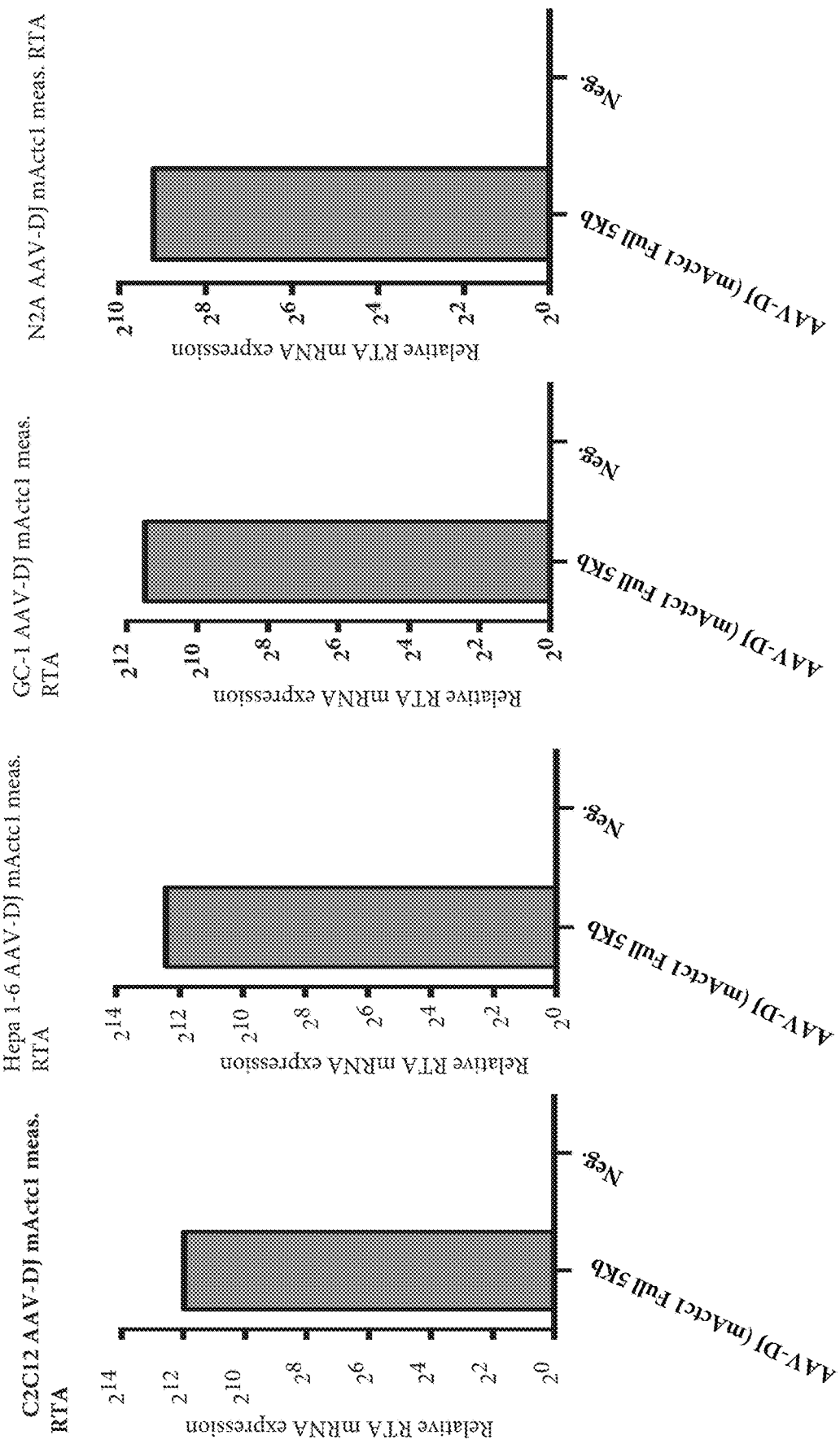
Figure 15D:
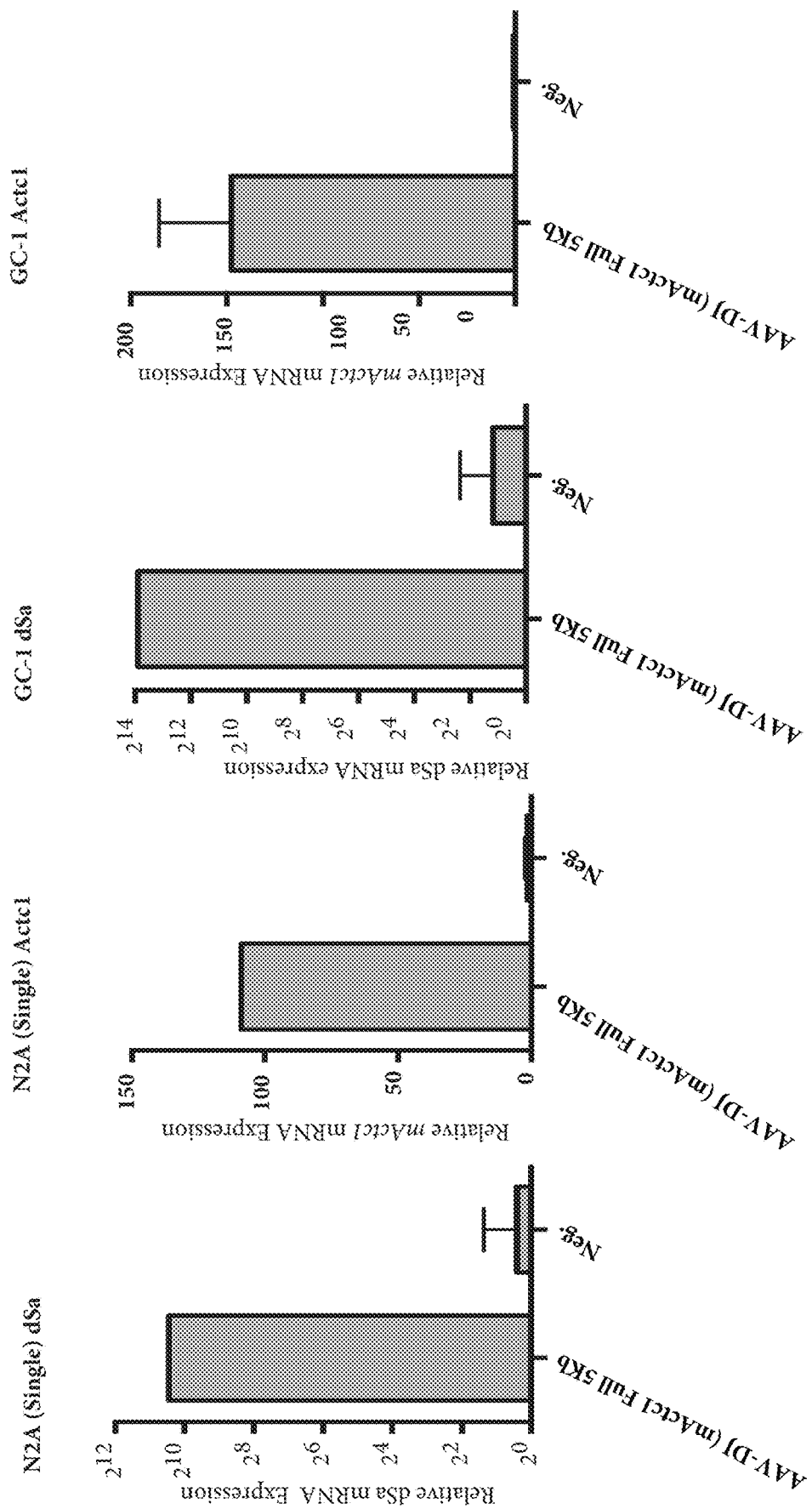

The single vector activator targeting Actc1 construct was packaged in AAV-DJ, as shown in FIGS. 14A-14B. For muscle delivery, the construct will be packaged in AAV6 using materials and methods that are or will become apparent to one of skill based on the present disclosure. Once gRNAs are identified for Utrn and Pygb, these constructs will be packaged in AAV-DJ and AAV6 as well, for delivery in vitro and to muscle tissue.

3.3 Validate AAV for Activation of Targets and Protein Production In Vitro

As shown in FIGS. 15A-15D, the AAV-DJ packaged with the Actc1 activation construct have been validated. This validation data will be replicated, and repeat the assay at various time points. The same will be done with Utrn and Pygb targeting AAV-DJ, once it is produced.

3.4 Deliver High Titer AAV In Vivo Locally to Determine Ability to Activate Targets Once the AAV6 is packaged with the activator tool targeting Actc1, it will be delivered both locally to hind limb muscle, and systemically. Mice will be assayed for over expression of the Actc1 gene in adult muscle tissue, liver, and additional organs. The same will be done with the Utrn and Pygb targeting viruses, once they are produced.

3.5 Deliver High Titer AAV to Mouse Models of Disease Phenotype to Assess Therapeutic Potential Once activation of the therapeutic target genes is validated in wild type mice in vivo, these AAV packaged constructs will be used in respective mouse disease models. The AAV packaged constructs will be delivered systemically and locally to hind limb muscle in both wild type mice as well as Acta1 knockout mice (which recapitulate the Nemaline Myopathy phenotype, and can be rescued via transgenic over expression of the Actc1 gene.) Additionally, AAV6 packaged constructs that target Utrn will be delivered to the MDX mice (knockout of the Dmd, which recapitulates the Duchenne Muscular Dystrophy phenotype) and AAV packaged with constructs targeting Pygb will be delivered to muscle glygogen phosphorylase knockout mice (recapitulates the McArdle's Disease phenotype.) The expression of the target genes will be detected in the mouse models and assessed for efficacy of disease treatment.

Applications:

Aspects of the present disclosure provides methods of using the single vector CRISPR AAV based system for modulating target gene expression. CRISPR Cas9 based genetic and epigenetic regulators are known for ease of use and has broad applications. Cas9 transcriptional regulators have been used to tackle several previously challenging biological applications. These regulators have been used to deconstruct genetic networks that confer resistance phenotypes, mediate cellular differentiation by activating endogenous genes, activate latent HIV genomes to improve efficacy of antiretroviral therapy, and induce a morphological phenotype in vivo. The present disclosure thus provides for applications to genome wide screening of poorly understood classes of genes, as well as transcriptional and epigenetic paradigms for human gene therapy using the single vector CRISPR AAV based system.

According to some aspects, the present disclosure contemplates treating diseases based on the single vector CRISPR AAV based system such as using Cas9 transcriptional regulators. Diseases such as Prader-Willi and Angelman Syndrome are caused by a pathogenic deletion in one parental allele, while the other fully functional allele is silenced due to genomic imprinting (the process by which certain alleles are silenced, depending on which parent it was inherited from). In such cases, the present disclosure provides methods of Cas9 based activators in the single vector CRISPR AAV based system which can activate expression from the silenced allele, providing expression of a fully intact copy of the missing gene.

According to other aspects, the present disclosure contemplates treating monogenetic diseases based on the single vector CRISPR AAV based system such as using Cas9 transcriptional regulators. The Cas9 transcriptional regulators can mediate modest overexpression of compensatory genes for disease treatment. For example, Duchenne Muscular Dystrophy (DMD) is an X-linked disease caused by mutations in the protein Dystrophin. Pathogenic mutations disrupt the protein Dystrophin, which is responsible for anchoring a cell's actin cytoskeleton to the extracellular matrix in muscle. Since Dystrophin is located on the X chromosome, male patients only have a single copy of Dystrophin; when that copy is mutated, no functional Dystrophin is available, and muscle tissue loses its integrity causing muscle weakness and wasting. As a result, patients have difficulty with walking, respiration, and other daily activities. Currently, there are no commercialized therapies for DMD. The present disclosure provides the single vector CRISPR AAV based system for treating DMD via direct editing of genomic mutations in Dystrophin to correct the faulty sequence[38,39].

An alternative approach, which has already been applied in clinical trials, is the up-regulation of a Dystrophin paralog, Utrophin, which can complement the function of mutated Dystrophin[40]. In clinical trials, small molecule mediated activation of expression is modest in its efficacy; direct activation of endogenous Utrophin expression with the single vector CRISPR AAV based system such as using Cas9 transcriptional activators based on the present disclosure may solve this issue in a straightforward manner. Activators may be delivered episomally via Adeno-associated virus (AAV) to muscle tissue, such as is the case with Glybera (the only approved gene therapy in the Western world, used to deliver a therapeutic gene to treat lipoprotein lipase deficiency)[41]. While such a method may not be a permanent cure, as the activator would not be stably integrated in to the genome of target cells, it is safer than Cas9 based genome-editing approaches that suffer from greater off-target effects, which are irreversible. Akin to Glybera, such a therapeutic may be delivered via local injection of gene therapy virus, and benefit from relatively long term expression in muscle tissue without the risk of permanent integration[41].

Expanding upon this paradigm, the present disclosure contemplates applications of the single vector CRISPR AAV based system such as using Cas9 transcriptional regulators for treating many monogenetic diseases that have genes having compensatory genetic paralogs that may be activated in a similar therapeutic approach. The highly programmable nature of Cas9 regulatory tools will allow for therapies developed for a single disease to be easily repurposed for other diseases that can be treated via activation or suppression of naturally encoded beneficial genes based on the present disclosure.

Sequences for the various activation domains, promoters and terminators used herein are summarized in Tables 1 and 2.

TABLE 1

Nucleic Acid and Protein Sequences for the Various Activation Domains

| Nucleic Acid | | Protein |
|---|---|---|
| VP64-SV40 | GAGGCCAGCGGTTCCGGACGGGCTGACGCATTGGA CGATTTTGATCTGGATATGCTGGGAAGTGACGCCCT CGATGATTTTGACCTTGACATGCTTGGTTCGGATGCC CTTGATGACTTTGACCTCGACATGCTCGGCAGTGAC GCCCTTGATGATTTCGACCTGGACATGCTGATTAACT CTAGAAGTTCCGGATCTCCGAAAAAGAAACGCAAA GTTGGT (SEQ ID NO: 1) | EASGSGRADALDDFDLD MLGSDALDDFDLDMLGS DALDDFDLDMLGSDALD DFDLDMLINSRSSGSPKKK RKVG (SEQ ID NO: 17) |
| p65 full TAD (transcription activation domain) | AGCCAGTACCTGCCCGACACCGACGACCGGCACCG GATCGAGGAAAAGCGGAAGCGGACCTACGAGACAT TCAAGAGCATCATGAAGAAGTCCCCCTTCAGCGGCC CCACCGACCCTAGACCTCCACCTAGAAGAATCGCCG TGCCCAGCAGATCCAGCGCCAGCGTGCCAAAACCTG CCCCCCAGCCTTACCCCTTCACCAGCAGCCTGAGCAC CATCAACTACGACGAGTTCCCTACCATGGTGTTCCCC AGCGGCCAGATCTCTCAGGCCTCTGCTCTGGCTCCA GCCCCTCCTCAGGTGCTGCCTCAGGCTCCTGCTCCTG CACCAGCTCCAGCCATGGTGTCTGCACTGGCTCAGG CACCAGCACCCGTGCCTGTGCTGGCTCCTGGACCTC CACAGGCTGTGGCTCCACCAGCCCCTAAACCTACAC AGGCCGGCGAGGGCACACTGTCTGAAGCTCTGCTG CAGCTGCAGTTCGACGACGAGGATCTGGGAGCCCT GCTGGGAAACAGCACCGATCCTGCCGTGTTCACCGA CCTGGCCAGCGTGGACAACAGCGAGTTCCAGCAGC TGCTGAACCAGGGCATCCCTGTGGCCCCTCACACCA CCGAGCCCATGCTGATGGAATACCCCGAGGCCATCA CCCGGCTCGTGACAGGCGCTCAGAGGCCTCCTGATC CAGCTCCTGCCCCTCTGGGAGCACCAGGCCTGCCTA ATGGACTGCTGTCTGGCGACGAGGACTTCAGCTCTA TCGCCGATATGGATTTCTCAGCCTTGCTG (SEQ ID NO: 2) | SQYLPDTDDRHRIEEKRKR TYETFKSIMKKSPFSGPTD PRPPPPRRIAVPSRSSASVP KPAPQPYPPFTSSLSTINYDE FPTMVFPSGQISQASALA PAPPQVLPQAPAPAPAPA MVSALAQAPAPVPVLAP GPPQAVAPPAPKPTQAGE GTLSEALLQLQFDDEDLG ALLGNSTDPAVFTDLASV DNSEFQQLLNQGIPVAPH TTEPMLMEYPEAITRLVTG AQRPPDPAPAPLGAPGLP NGLLSGDEDFSSIADMDF SALL (SEQ ID NO: 18) |
| RTA full TAD | CGGGATTCCAGGGAAGGGATGTTTTTGCCGAAGCCT GAGGCCGGCTCCGCTATTAGTGACGTGTTTGAGGGC CGCGAGGTGTGCCAGCCAAAACGAATCCGGCCATTT CATCCTCCAGGAAGTCCATGGGCCAACCGCCCACTC CCCGCCAGCCTCGCACCAACACCAACCGGTCCAGTA CATGAGCCAGTCGGGTCACTGACCCCGGCACCAGTC CCTCAGCCACTGGATCCAGCGCCCGCAGTGACTCCC GAGGCCAGTCACCTGTTGGAGGATCCCGATGAAGA GACGAGCCAGGCTGTCAAAGCCCTTCGGGAGATGG CCGATACTGTGATTCCCCAGAAGGAAGAGGCTGCAA TCTGTGGCCAAATGGACCTTTCCCATCCGCCCCCAAG GGGCCATCTGGATGAGCTGACAACCACACTTGAGTC CATGACCGAGGATCTGAACCTGGACTCACCCCTGAC CCCGGAATTGAACGAGATTCTGGATACCTTCCTGAA CGACGAGTGCCTCTTGCATGCCATGCATATCAGCAC AGGACTGTCCATCTTCGACACATCTCTGTTT (SEQ ID NO: 3) | RDSREGMFLPKPEAGSAIS DVFEGREVCQPKRIRPFHP PGSPWANRPLPASLAPTP TGPVHEPVGSLTPAPVPQ PLDPAPAVTPEASHLLEDP DEETSQAVKALREMADTV IPQKEEAAICGQMDLSHP PPRGHLDELTTTLESMTED LNLDSPLTPELNEILDTFLN DECLLHAMHISTGLSIFDT SLF (SEQ ID NO: 19) |
| p65 (aa100-aa261) | GTGCTGCCTCAGGCTCCTGCTCCTGCACCAGCTCCA GCCATGGTGTCTGCACTGGCTCAGGCACCAGCACCC GTGCCTGTGCTGGCTCCTGGACCTCCACAGGCTGTG GCTCCACCAGCCCCTAAACCTACACAGGCCGGCGAG GGCACACTGTCTGAAGCTCTGCTGCAGCTGCAGTTC GACGACGAGGATCTGGGAGCCCTGCTGGGAAACAG CACCGATCCTGCCGTGTTCACCGACCTGGCCAGCGT GGACAACAGCGAGTTCCAGCAGCTGCTGAACCAGG GCATCCCTGTGGCCCCTCACACCACCGAGCCCATGC TGATGGAATACCCCGAGGCCATCACCCGGCTCGTGA CAGGCGCTCAGAGGCCTCCTGATCCAGCTCCTGCCC CTCTGGGAGCACCAGGCCTGCCTAATGGACTGCTGT CTGGCGACGAGGACTTCAGCTCTATCGCCGATATGG ATTTCTCAGCCTTGCTG (SEQ ID NO: 4) | VLPQAPAPAPAPAMVSAL AQAPAPVPVLAPGPPQA VAPPAPKPTQAGEGTLSE ALLQLQFDDEDLGALLGN STDPAVFTDLASVDNSEF QQLLNQGIPVAPHTTEPM LMEYPEAITRLVTGAQRPP DPAPAPLGAPGLPNGLLS GDEDFSSIADMDFSALL (SEQ ID NO: 20) |
| p65 (aa150-aa261) | CTGTCTGAAGCTCTGCTGCAGCTGCAGTTCGACGAC GAGGATCTGGGAGCCCTGCTGGGAAACAGCACCGA TCCTGCCGTGTTCACCGACCTGGCCAGCGTGGACAA CAGCGAGTTCCAGCAGCTGCTGAACCAGGGCATCCC TGTGGCCCCTCACACCACCGAGCCCATGCTGATGGA | MSEALLQLQFDDEDLGAL LGNSTDPAVFTDLASVDN SEFQQLLNQGIPVAPHTTE PMLMEYPEAITRLVTGAQ RPPDPAPAPLGAPGLPNG |

TABLE 1-continued

Nucleic Acid and Protein Sequences for the Various Activation Domains

| Nucleic Acid | Protein |
|---|---|
| ATACCCCGAGGCCATCACCCGGCTCGTGACAGGCGC<br>TCAGAGGCCTCCTGATCCAGCTCCTGCCCCTCTGGG<br>AGCACCAGGCCTGCCTAATGGACTGCTGTCTGGCGA<br>CGAGGACTTCAGCTCTATCGCCGATATGGATTTCTCA<br>GCCTTGCTG<br>(SEQ ID NO: 5) | LLSGDEDFSSIADMDFSAL<br>L<br>(SEQ ID NO: 21) |
| p65 (aa200-aa261)<br>GCCCCTCACACCACCGAGCCCATGCTGATGGAATAC<br>CCCGAGGCCATCACCCGGCTCGTGACAGGCGCTCAG<br>AGGCCTCCTGATCCAGCTCCTGCCCCTCTGGGAGCA<br>CCAGGCCTGCCTAATGGACTGCTGTCTGGCGACGAG<br>GACTTCAGCTCTATCGCCGATATGGATTTCTCAGCCT<br>TGCTG<br>(SEQ ID NO: 6) | APHTTEPMLMEYPEAITRL<br>VTGAQRPPDPAPAPLGAP<br>GLPNGLLSGDEDFSSIAD<br>MDFSALL<br>(SEQ ID NO: 22) |
| p65 (aa1-aa200)<br>AGCCAGTACCTGCCCGACACCGACGACCGGCACCG<br>GATCGAGGAAAAGCGGAAGCGGACCTACGAGACAT<br>TCAAGAGCATCATGAAGAAGTCCCCCTTCAGCGGCC<br>CCACCGACCCTAGACCTCCACCTAGAAGAATCGCCG<br>TGCCCAGCAGATCCAGCGCCAGCGTGCCAAAACCTG<br>CCCCCCAGCCTTACCCCTTCACCAGCAGCCTGAGCAC<br>CATCAACTACGACGAGTTCCCTACCATGGTGTTCCCC<br>AGCGGCCAGATCTCTCAGGCCTCTGCTCTGGCTCCA<br>GCCCCTCCTCAGGTGCTGCCTCAGGCTCCTGCTCCTG<br>CACCAGCTCCAGCCATGGTGTCTGCACTGGCTCAGG<br>CACCAGCACCCGTGCCTGTGCTGGCTCCTGGACCTC<br>CACAGGCTGTGGCTCCACCAGCCCCTAAACCTACAC<br>AGGCCGGCGAGGGCACACTGTCTGAAGCTCTGCTG<br>CAGCTGCAGTTCGACGACGAGGATCTGGGAGCCCT<br>GCTGGGAAACAGCACCGATCCTGCCGTGTTCACCGA<br>CCTGGCCAGCGTGGACAACAGCGAGTTCCAGCAGC<br>TGCTGAACCAGGGCATCCCTGTGGCC (SEQ ID NO: 7) | SQYLPDTDDRHRIEEKRKR<br>TYETFKSIMKKSPFSGPTD<br>PRPPPRRIAVPSRSSASVP<br>KPAPQPYPFTSSLSTINYDE<br>FPTMVFPSGQISQASALA<br>PAPPQVLPQAPAPAPAPA<br>MVSALAQAPAPVPVLAP<br>GPPQAVAPPAPKPTQAGE<br>GTLSEALLQLQFDDEDLG<br>ALLGNSTDPAVFTDLASV<br>DNSEFQQLLNQGIPVA<br>(SEQ ID NO: 23) |
| p65 (aa1-aa150)<br>AGCCAGTACCTGCCCGACACCGACGACCGGCACCG<br>GATCGAGGAAAAGCGGAAGCGGACCTACGAGACAT<br>TCAAGAGCATCATGAAGAAGTCCCCCTTCAGCGGCC<br>CCACCGACCCTAGACCTCCACCTAGAAGAATCGCCG<br>TGCCCAGCAGATCCAGCGCCAGCGTGCCAAAACCTG<br>CCCCCCAGCCTTACCCCTTCACCAGCAGCCTGAGCAC<br>CATCAACTACGACGAGTTCCCTACCATGGTGTTCCCC<br>AGCGGCCAGATCTCTCAGGCCTCTGCTCTGGCTCCA<br>GCCCCTCCTCAGGTGCTGCCTCAGGCTCCTGCTCCTG<br>CACCAGCTCCAGCCATGGTGTCTGCACTGGCTCAGG<br>CACCAGCACCCGTGCCTGTGCTGGCTCCTGGACCTC<br>CACAGGCTGTGGCTCCACCAGCCCCTAAACCTACAC<br>AGGCCGGCGAGGGCACA (SEQ ID NO: 8) | SQYLPDTDDRHRIEEKRKR<br>TYETFKSIMKKSPFSGPTD<br>PRPPPRRIAVPSRSSASVP<br>KPAPQPYPFTSSLSTINYDE<br>FPTMVFPSGQISQASALA<br>PAPPQVLPQAPAPAPAPA<br>MVSALAQAPAPVPVLAP<br>GPPQAVAPPAPKPTQAGE<br>GT<br>(SEQ ID NO: 24) |
| p65 (aa1-aa100)<br>AGCCAGTACCTGCCCGACACCGACGACCGGCACCG<br>GATCGAGGAAAAGCGGAAGCGGACCTACGAGACAT<br>TCAAGAGCATCATGAAGAAGTCCCCCTTCAGCGGCC<br>CCACCGACCCTAGACCTCCACCTAGAAGAATCGCCG<br>TGCCCAGCAGATCCAGCGCCAGCGTGCCAAAACCTG<br>CCCCCCAGCCTTACCCCTTCACCAGCAGCCTGAGCAC<br>CATCAACTACGACGAGTTCCCTACCATGGTGTTCCCC<br>AGCGGCCAGATCTCTCAGGCCTCTGCTCTGGCTCCA<br>GCCCCTCCTCAG<br>(SEQ ID NO: 9) | SQYLPDTDDRHRIEEKRKR<br>TYETFKSIMKKSPFSGPTD<br>PRPPPRRIAVPSRSSASVP<br>KPAPQPYPFTSSLSTINYDE<br>FPTMVFPSGQISQASALA<br>PAPPQ<br>(SEQ ID NO: 25) |
| p65 (aa50-aa150)<br>AGATCCAGCGCCAGCGTGCCAAAACCTGCCCCCCAG<br>CCTTACCCCTTCACCAGCAGCCTGAGCACCATCAACT<br>ACGACGAGTTCCCTACCATGGTGTTCCCCAGCGGCC<br>AGATCTCTCAGGCCTCTGCTCTGGCTCCAGCCCCTCC<br>TCAGGTGCTGCCTCAGGCTCCTGCTCCTGCACCAGCT<br>CCAGCCATGGTGTCTGCACTGGCTCAGGCACCAGCA<br>CCCGTGCCTGTGCTGGCTCCTGGACCTCCACAGGCT<br>GTGGCTCCACCAGCCCCTAAACCTACACAGGCCGGC<br>GAGGGCACA<br>(SEQ ID NO: 10) | RSSASVPKPAPQPYPFTSS<br>LSTINYDEFPTMVFPSGQI<br>SQASALAPAPPQVLPQAP<br>APAPAPAMVSALAQAPA<br>PVPVLAPGPPQAVAPPAP<br>KPTQAGEGT<br>(SEQ ID NO: 26) |
| RTA (aa75-aa190)<br>CCACTGGATCCAGCGCCCGCAGTGACTCCCGAGGCC<br>AGTCACCTGTTGGAGGATCCCGATGAAGAGACGAG<br>CCAGGCTGTCAAAGCCCTTCGGGAGATGGCCGATAC<br>TGTGATTCCCCAGAAGGAAGAGGCTGCAATCTGTG<br>GCCAAATGGACCTTTCCCATCCGCCCCCAAGGGGCC<br>ATCTGGATGAGCTGACAACCACACTTGAGTCCATGA | PLDPAPAVTPEASHLLEDP<br>DEETSQAVKALREMADTV<br>IPQKEEAAICGQMDLSHP<br>PPRGHLDELTTTLESMTED<br>LNLDSPLTPELNEILDTFLN<br>DECLLHAMHISTGLSIFDT |

TABLE 1-continued

Nucleic Acid and Protein Sequences for the Various Activation Domains

| Nucleic Acid | | Protein |
|---|---|---|
| | CCGAGGATCTGAACCTGGACTCACCCCTGACCCCGG<br>AATTGAACGAGATTCTGGATACCTTCCTGAACGACG<br>AGTGCCTCTTGCATGCCATGCATATCAGCACAGGAC<br>TGTCCATCTTCGACACATCTCTGTTT<br>(SEQ ID NO: 11) | SLF<br>(SEQ ID NO: 27) |
| RTA<br>(aa125-<br>aa190) | GACCTTTCCCATCCGCCCCAAGGGGCCATCTGGAT<br>GAGCTGACAACCACACTTGAGTCCATGACCGAGGAT<br>CTGAACCTGGACTCACCCCTGACCCCGGAATTGAAC<br>GAGATTCTGGATACCTTCCTGAACGACGAGTGCCTC<br>TTGCATGCCATGCATATCAGCACAGGACTGTCCATCT<br>TCGACACATCTCTGTTT (SEQ ID NO: 12) | DLSHPPPRGHLDELTTTLE<br>SMTEDLNLDSPLTPELNE1<br>LDTFLNDECLLHAMHISTG<br>LSIFDTSLF<br>(SEQ ID NO: 28) |
| RTA (aa50-<br>aa175) | AGCCTCGCACCAACACCAACCGGTCCAGTACATGAG<br>CCAGTCGGGTCACTGACCCCGGCACCAGTCCCTCAG<br>CCACTGGATCCAGCGCCCGCAGTGACTCCCGAGGCC<br>AGTCACCTGTTGGAGGATCCCGATGAAGAGACGCAG<br>CCAGGCTGTCAAAGCCCTTCGGGAGATGGCCGATAC<br>TGTGATTCCCCAGAAGGAAGAGGCTGCAATCTGTG<br>GCCAAATGGACCTTTCCCATCCGCCCCAAGGGGCC<br>ATCTGGATGAGCTGACAACCACACTTGAGTCCATGA<br>CCGAGGATCTGAACCTGGACTCACCCCTGACCCCGG<br>AATTGAACGAGATTCTGGATACCTTCCTGAACGACG<br>AGTGCCTCTTGCATGCC (SEQ ID NO: 13) | SLAPTPTGPVHEPVGSLTP<br>APVPQPLDPAPAVTPEAS<br>HLLEDPDEETSQAVKALRE<br>MADTVIPQKEEAAICGQ<br>MDLSHPPPRGHLDELTTT<br>LESMTEDLNLDSPLTPELN<br>EILDTFLNDECLLHA<br>(SEQ ID NO: 29) |
| RTA (aa75-<br>aa175) | CCACTGGATCCAGCGCCCGCAGTGACTCCCGAGGCC<br>AGTCACCTGTTGGAGGATCCCGATGAAGAGACGAG<br>CCAGGCTGTCAAAGCCCTTCGGGAGATGGCCGATAC<br>TGTGATTCCCCAGAAGGAAGAGGCTGCAATCTGTG<br>GCCAAATGGACCTTTCCCATCCGCCCCAAGGGGCC<br>ATCTGGATGAGCTGACAACCACACTTGAGTCCATGA<br>CCGAGGATCTGAACCTGGACTCACCCCTGACCCCGG<br>AATTGAACGAGATTCTGGATACCTTCCTGAACGACG<br>AGTGCCTCTTGCATGCC<br>(SEQ ID NO: 14) | PLDPAPAVTPEASHLLEDP<br>DEETSQAVKALREMADTV<br>IPQKEEAAICGQMDLSHP<br>PPRGHLDELTTTLESMTED<br>LNLDSPLTPELNEILDTFLN<br>DECLLHA<br>(SEQ ID NO: 30) |
| RTA<br>(aa100-<br>aa175) | GCTGTCAAAGCCCTTCGGGAGATGGCCGATACTGTG<br>ATTCCCCAGAAGGAAGAGGCTGCAATCTGTGGCCAA<br>ATGGACCTTTCCCATCCGCCCCAAGGGGCCATCTG<br>GATGAGCTGACAACCACACTTGAGTCCATGACCGAG<br>GATCTGAACCTGGACTCACCCCTGACCCCGGAATTG<br>AACGAGATTCTGGATACCTTCCTGAACGACGAGTGC<br>CTCTTGCATGCC (SEQ ID NO: 15) | AVKALREMADTVIPQKEE<br>AAICGQMDLSHPPPRGHL<br>DELTTTLESMTEDLNLDSP<br>LTPELNEILDTFLNDECLLH<br>A<br>(SEQ ID NO: 31) |
| RTA<br>(aa125-<br>aa175) | GACCTTTCCCATCCGCCCCAAGGGGCCATCTGGAT<br>GAGCTGACAACCACACTTGAGTCCATGACCGAGGAT<br>CTGAACCTGGACTCACCCCTGACCCCGGAATTGAAC<br>GAGATTCTGGATACCTTCCTGAACGACGAGTGCCTC<br>TTGCATGCC (SEQ ID NO: 16) | DLSHPPPRGHLDELTTTLE<br>SMTEDLNLDSPLTPELNEI<br>LDTFLNDECLLHA<br>(SEQ ID NO: 32) |

TABLE 2

Promoter and Terminator Sequences

| SCP1<br>promoter | TACTTATATAAGGGGGTGGGGGCGCGTTCGTCCTCAGTCGCGATCGAACACTCGAGC<br>CGAGCAGACGTGCCTACGGACCG (SEQ ID NO: 33) |
|---|---|
| EFS<br>promoter | TAGGTCTTGAAAGGAGTGGGAATTGGCTCCGGTGCCCGTCAGTGGGCAGAGCGCAC<br>ATCGCCCACAGTCCCCGAGAAGTTGGGGGGAGGGGTCGGCAATTGATCCGGTGCCT<br>AGAGAAGGTGGCGCGGGGTAAACTGGGAAAGTGATGTCGTGTACTGGCTCCGCCTT<br>TTTCCCGAGGGTGGGGGAGAACCGTATATAAGTGCAGTAGTCGCCGTGAACGTTCTT<br>TTTCGCAACGGGTTTGCCGCCAGAACACAGG (SEQ ID NO: 34) |
| 1X-sNRP1<br>terminator | AAATAAAATACGAAATG (SEQ ID NO: 35) |
| 2X-sNRP1<br>terminator | AAATAAAATACGAAATGAAATAAAATACGAAATG (SEQ ID NO: 36) |
| Syn pA<br>terminator | AATAAAATATCTTTATTTTCATTACATCTGTGTGTTGGTTTTTTGTGTG (SEQ ID NO: 37) |

REFERENCES

The disclosure of each reference cited is expressly incorporated herein.
1. Gilbert, L. A. et al. CRISPR-Mediated Modular RNA-Guided Regulation of Transcription in Eukaryotes. *Cell* 154, 442-451 (2013).
2. Mali, P. et al. CAS9 transcriptional activators for target specificity screening and paired nickases for cooperative genome engineering. *Nat. Biotechnol.* 31, 833-838 (2013).
3. Maeder, M. L. et al. CRISPR RNA-guided activation of endogenous human genes. *Nat. Methods* 10, 977-979 (2013).
4. Cheng, A. W. et al. Multiplexed activation of endogenous genes by CRISPR-on, an RNA-guided transcriptional activator system. *Cell Res.* 23, 1163-1171 (2013).
5. Perez-Pinera, P. et al. RNA-guided gene activation by CRISPR-Cas9-based transcription factors. *Nat. Methods* 10, 973-976 (2013).
6. Mali, P., Esvelt, K. M. & Church, G. M. Cas9 as a versatile tool for engineering biology. *Nat. Methods* 10, 957-963 (2013).
7. Hsu, P. D., Lander, E. S. & Zhang, F. Development and Applications of CRISPR-Cas9 for Genome Engineering. *Cell* 157, 1262-1278 (2014).
8. Chavez, A. et al. Highly efficient Cas9-mediated transcriptional programming. *Nat. Methods* 12, 326-328 (2015).
9. Rivenbark, A. G. et al. Epigenetic reprogramming of cancer cells via targeted DNA methylation. *Epigenetics* 7, 350-360 (2012).
10. Snowden, A. W., Gregory, P. D., Case, C. C. & Pabo, C. O. Gene-Specific Targeting of H3K9 Methylation Is Sufficient for Initiating Repression In Vivo. *Curr. Biol.* 12, 2159-2166 (2002).
11. Mendenhall, E. M. et al. Locus-specific editing of histone modifications at endogenous enhancers. *Nat. Biotechnol.* 31, 1133-1136 (2013).
12. Konermann, S. et al. Optical control of mammalian endogenous transcription and epigenetic states. *Nature* advance online publication, (2013).
13. Maeder, M. L. et al. Robust, synergistic regulation of human gene expression using TALE activators. *Nat. Methods* 10, 243-245 (2013).
14. Perez-Pinera, P. et al. Synergistic and tunable human gene activation by combinations of synthetic transcription factors. *Nat. Methods* 10, 239-242 (2013).
15. Bernstein, D. L., Le Lay, J. E., Ruano, E. G. & Kaestner, K. H. TALE-mediated epigenetic suppression of CDKN2A increases replication in human fibroblasts. *J. Clin. Invest.* 125, 1998-2006 (2015).
16. Maeder, M. L. et al. Targeted DNA demethylation and activation of endogenous genes using programmable TALE-TET1 fusion proteins. *Nat. Biotechnol.* 31, 1137-1142 (2013).
17. Dhanasekaran, M., Negi, S. & Sugiura, Y. Designer Zinc Finger Proteins: Tools for Creating Artificial DNA-Binding Functional Proteins. *Acc. Chem. Res.* 39, 45-52 (2006).
18. Maeder, M. L. et al. Rapid 'Open-Source' Engineering of Customized Zinc-Finger Nucleases for Highly Efficient Gene Modification. *Mol. Cell* 31, 294-301 (2008).
19. Reyon, D. et al. FLASH assembly of TALENs for high-throughput genome editing. *Nat. Biotechnol.* 30, 460-465 (2012).
20. Bolotin, A., Quinquis, B., Sorokin, A. & Ehrlich, S. D. Clustered regularly interspaced short palindrome repeats (CRISPRs) have spacers of extrachromosomal origin. *Microbiology* 151, 2551-2561 (2005).
21. Mojica, F. J. M., Díez-Villaseñor, C., García-Martínez, J. & Soria, E. Intervening sequences of regularly spaced prokaryotic repeats derive from foreign genetic elements. *J. Mol. Evol.* 60, 174-182 (2005).
22. Pourcel, C., Salvignol, G. & Vergnaud, G. CRISPR elements in *Yersinia pestis* acquire new repeats by preferential uptake of bacteriophage DNA, and provide additional tools for evolutionary studies. *Microbiology* 151, 653-663 (2005).
23. Barrangou, R. et al. CRISPR Provides Acquired Resistance Against Viruses in Prokaryotes. *Science* 315, 1709-1712 (2007).
24. Tang, T.-H. et al. Identification of 86 candidates for small non-messenger RNAs from the archaeon *Archaeoglobus fulgidus*. *Proc. Natl. Acad. Sci.* 99, 7536-7541 (2002).
25. Brouns, S. J. J. et al. Small CRISPR RNAs Guide Antiviral Defense in Prokaryotes. *Science* 321, 960-964 (2008).
26. Makarova, K. S. et al. An updated evolutionary classification of CRISPR-Cas systems. *Nat. Rev. Microbiol.* 13, 722-736 (2015).
27. Jinek, M. et al. A Programmable Dual-RNA-Guided DNA Endonuclease in Adaptive Bacterial Immunity. *Science* 337, 816-821 (2012).
28. Cong, L. et al. Multiplex Genome Engineering Using CRISPR/Cas Systems. *Science* 339, 819-823 (2013).
29. Mali, P. et al. RNA-Guided Human Genome Engineering via Cas9. *Science* 339, 823-826 (2013).
30. Jinek, M. et al. RNA-programmed genome editing in human cells. *eLife* 2, e00471 (2013).
31. Deveau, H. et al. Phage Response to CRISPR-Encoded Resistance in *Streptococcus thermophilus*. *J. Bacteriol.* 190, 1390-1400 (2008).
32. Mojica, F. J. M., Díez-Villaseñor, C., García-Martínez, J. & Almendros, C. Short motif sequences determine the targets of the prokaryotic CRISPR defence system. *Microbiology* 155, 733-740 (2009).
33. Ran, F. A. et al. Genome engineering using the CRISPR-Cas9 system. *Nat. Protoc.* 8, 2281-2308 (2013).
34. Kosuri, S. & Church, G. M. Large-scale de novo DNA synthesis: technologies and applications. *Nat. Methods* 11, 499-507 (2014).
35. CustomArray, Inc.—maker of custom microarrays, oligo pools and instrumentation. Available at: http://customarrayinc.com/oligos_main.htm. (Accessed: 27th January 2016)
36. Sander, J. D. & Joung, J. K. CRISPR-Cas systems for editing, regulating and targeting genomes. *Nat. Biotechnol.* 32, 347-355 (2014).
37. Weeks, D. P., Spalding, M. H. & Yang, B. Use of designer nucleases for targeted gene and genome editing in plants. *Plant Biotechnol. J.* 14, 483-495 (2015).
38. Nelson, C. E. et al. In vivo genome editing improves muscle function in a mouse model of Duchenne muscular dystrophy. *Science* 351, 403-407 (2016).
39. Tabebordbar, M. et al. In vivo gene editing in dystrophic mouse muscle and muscle stem cells. *Science* 351, 407-411 (2016).
40. Wojtal, D. et al. Spell Checking Nature: Versatility of CRISPR/Cas9 for Developing Treatments for Inherited Disorders. *Am. J. Hum. Genet.* 98, 90-101 (2016).
41. Glybera, INN-alipogene tiparvovec. Annex I. Summary of Product Characteristics. Available at: http:// www.ema.europa.eu/docs/en_GB/document_library/EPAR_-_Public_assessment_report/human/002145/WC500135476.pdf. (Accessed: 11th April 2016)

42. Poss, Z. C., Ebmeier, C. C. & Taatjes, D. J. The Mediator complex and transcription regulation. *Crit. Rev. Biochem. Mol. Biol.* 48, 575-608 (2013).

43. Chen, L.-W. et al. Two phenylalanines in the C-terminus of Epsteinn-Barr virus Rta protein reciprocally modulate its DNA binding and transactivation function. *Virology* 386, 448-461 (2009).

44. Spitz, F. & Furlong, E. E. M. Transcription factors: from enhancer binding to developmental control. *Nat. Rev. Genet.* 13, 613-626 (2012).

45. Gersbach, C. A. & Perez-Pinera, P. Activating human genes with zinc finger proteins, transcription activator-like effectors and CRISPR/Cas9 for gene therapy and regenerative medicine. *Expert Opin. Ther. Targets* 18, 835-839 (2014).

46. Esvelt, K. M. et al. Orthogonal Cas9 proteins for RNA-guided gene regulation and editing. *Nat. Methods* 10, 1116-1121 (2013).

47. Zhang, Y. et al. Rapid Single-Step Induction of Functional Neurons from Human Pluripotent Stem Cells. *Neuron* 78, 785-798 (2013).

48. Gingras, M., Champigny, M.-F. & Berthod, F. Differentiation of human adult skin-derived neuronal precursors into mature neurons. *J. Cell. Physiol.* 210, 498-506 (2007).

49. Ran, F. A. et al. In vivo genome editing using *Staphylococcus aureus* Cas9. *Nature* 520, 186-191 (2015).

50. McFarland, T. J. et al. Evaluation of a novel short polyadenylation signal as an alternative to the SV40 polyadenylation signal. *Plasmid* 56, 62-67 (2006).

51. Martinez-Lopez, A. et al. Improving the safety of viral DNA vaccines: development of vectors containing both 5' and 3' homologous regulatory sequences from non-viral origin. *Appl. Microbiol. Biotechnol.* 97, 3007-3016 (2012).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of activating expression of a target nucleic acid sequence in a eukaryotic cell comprising:
introducing into the cell a nucleic acid sequence encoding a Cas9 fusion protein and a guide RNA, wherein the Cas9 fusion protein comprises a nuclease-null Cas9 (dCas9) fused with an activation domain of VP64, an activation domain of p65, and an activation domain of RTA, wherein the activation domain of p65 comprises a protein sequence of SEQ ID NO: 18, SEQ ID NO: 20, SEQ ID NO: 21, SEQ ID NO: 22, SEQ ID NO: 23, SEQ ID NO: 24, SEQ ID NO: 25, or SEQ ID NO: 26, wherein the Cas9 fusion protein and the guide RNA are expressed and co-localize at a target site and activate the expression of the target nucleic acid sequence.

2. The method of claim 1 wherein the activation domains of VP64, p65 and RTA comprises a tripartite VP64-p65-RTA (VPR) fusion wherein each of the activation domains of VP64, p65 and RTA is truncated.

3. The method of claim 1 wherein a sequence encoding the Cas9 fusion protein is flanked by a promoter sequence at its 5' end and a terminator sequence at its 3' end wherein the promoter sequence is truncated.

4. The method of claim 3 wherein the terminator sequence is truncated.

5. The method of claim 4 wherein the terminator sequence comprises a short 17nt sNRP-1 (SEQ ID NO: 35), a 34nt dual sNRP-1 (SEQ ID NO: 36), a 50nt synthetic (SEQ ID NO: 37), or a 250 nt bGHR terminator.

6. The method of claim 1 wherein the activation domain of VP64 is a modified activation domain comprising protein sequence of SEQ ID NO: 17.

7. The method of claim 6 wherein the protein sequence is encoded by nucleic acid sequence of SEQ ID NO: 1.

8. The method of claim 1 wherein the activation domain of p65 is encoded by nucleic acid sequence of SEQ ID NO: 2, SEQ ID NO: 4, SEQ ID NO: 5, SEQ ID NO: 6, SEQ ID NO: 7, SEQ ID NO: 8, SEQ ID NO: 9, or SEQ ID NO: 10, respectively.

9. The method of claim 1 wherein the activation domain of RTA is a modified activation domain comprising RTA deletion protein.

10. The method of claim 9 wherein the RTA deletion protein comprises protein sequence of SEQ ID NO: 19, SEQ ID NO: 27, SEQ ID NO: 28, SEQ ID NO: 29, SEQ ID NO: 30, SEQ ID NO: 31, or SEQ ID NO: 32.

11. The method of claim 10 wherein the protein sequence is encoded by nucleic acid sequence of SEQ ID NO: 3, SEQ ID NO: 11, SEQ ID NO: 12, SEQ ID NO: 13, SEQ ID NO: 14, SEQ ID NO: 15, or SEQ ID NO: 16, respectively.

12. The method of claim 1 wherein the activation domain of VP64 is a modified activation domain comprising protein sequence of SEQ ID NO: 17 and the activation domain of RTA is a modified activation domain comprising SEQ ID NO: 19, SEQ ID NO: 27, SEQ ID NO: 28, SEQ ID NO: 29, SEQ ID NO: 30, SEQ ID NO: 31, or SEQ ID NO: 32.

13. A method of activating expression of a target nucleic acid sequence in a eukaryotic cell comprising:
introducing into the cell a nucleic acid sequence encoding a Cas9 fusion protein and a guide RNA, wherein the Cas9 fusion protein comprises a nuclease-null Cas9 (dCas9) fused with an activation domain of VP64, an activation domain of p65, and an activation domain of RTA, wherein the activation domain of RTA comprises a protein sequence of SEQ ID NO: 19, SEQ ID NO: 27, SEQ ID NO: 28, SEQ ID NO: 29, SEQ ID NO: 30, SEQ ID NO: 31, or SEQ ID NO: 32,
wherein the Cas9 fusion protein and the guide RNA are expressed and co-localize at a target site and activate the expression of the target nucleic acid sequence.

14. The method of claim 13 wherein the protein sequence is encoded by nucleic acid sequence of SEQ ID NO: 3, SEQ ID NO: 11, SEQ ID NO: 12, SEQ ID NO: 13, SEQ ID NO: 14, SEQ ID NO: 15, or SEQ ID NO: 16, respectively.

15. The method of claim 13 wherein the activation domains of VP64, p65 and RTA comprises a tripartite VP64-p65-RTA (VPR) fusion wherein each of the activation domains of VP64, p65 and RTA is truncated.

16. The method of claim 13 wherein a sequence encoding the Cas9 fusion protein is flanked by a promoter sequence at its 5' end and a terminator sequence at its 3' end wherein the promoter sequence is truncated.

17. The method of claim 16 wherein the terminator sequence is truncated.

18. The method of claim 16 wherein the terminator sequence comprises a short 17nt sNRP-1 (SEQ ID NO: 35), a 34nt dual sNRP-1 (SEQ ID NO: 36), a 50nt synthetic (SEQ ID NO: 37), or a 250 nt bGHR terminator.

19. The method of claim 13 wherein the activation domain of VP64 is a modified activation domain comprising protein sequence of SEQ ID NO: 17.

20. The method of claim 19 wherein the protein sequence is encoded by nucleic acid sequence of SEQ ID NO: 1.

21. The method of claim 13 wherein the activation domain of p65 is a modified activation domain comprising p65 deletion protein.

22. The method of claim 21 wherein the p65 deletion protein comprises protein sequence of SEQ ID NO: 18, SEQ ID NO: 20, SEQ ID NO: 21, SEQ ID NO: 22, SEQ ID NO: 23, SEQ ID NO: 24, SEQ ID NO: 25, or SEQ ID NO: 26.

23. The method of claim 13 wherein the activation domain of p65 is encoded by nucleic acid sequence of SEQ ID NO: 2, SEQ ID NO: 4, SEQ ID NO: 5, SEQ ID NO: 6, SEQ ID NO: 7, SEQ ID NO: 8, SEQ ID NO: 9, or SEQ ID NO: 10, respectively.

24. The method of claim 13 wherein the activation domain of VP64 is a modified activation domain comprising protein sequence of SEQ ID NO: 17 and wherein the activation domain of p65 is a modified activation domain comprising protein sequence of SEQ ID NO: 18, SEQ ID NO: 20, SEQ ID NO: 21, SEQ ID NO: 22, SEQ ID NO: 23, SEQ ID NO: 24, SEQ ID NO: 25, or SEQ ID NO: 26.

25. The method of claim 1 wherein the nucleic acid sequence encoding a Cas9 fusion protein and a guide RNA is within an AAV which is introduce into the eukaryotic cell.

26. The method of claim 15 wherein the nucleic acid sequence encoding a Cas9 fusion protein and a guide RNA is within an AAV which is introduce into the eukaryotic cell.

27. The method of claim 1 wherein the Cas9 is spCas9, St1Cas9 or SaCas9.

28. The method of claim 13 wherein the Cas9 is spCas9, St1Cas9 or SaCas9.

* * * * *